(12) United States Patent
Marliere et al.

(10) Patent No.: US 9,850,504 B2
(45) Date of Patent: Dec. 26, 2017

(54) METHOD FOR THE ENZYMATIC PRODUCTION OF 3-BUTEN-2-ONE

(71) Applicants: Scientist of Fortune S.A., Luxembourg (LU); Global Bioenergies, Evry (FR)

(72) Inventors: Philippe Marliere, Tournai (BE); Maria Anissimova, Nozay (FR); Mathieu Allard, Saint-Vrain (FR)

(73) Assignees: Scientist of Fortune, S.A., Luxembourg (LU); Global Bioenergies, Evry (FR)

( * ) Notice: Subject to any disclaimer, the term of this patent is extended or adjusted under 35 U.S.C. 154(b) by 0 days.

(21) Appl. No.: 14/902,565

(22) PCT Filed: Jul. 2, 2014

(86) PCT No.: PCT/EP2014/064102
§ 371 (c)(1),
(2) Date: Jan. 2, 2016

(87) PCT Pub. No.: WO2015/000981
PCT Pub. Date: Jan. 8, 2015

(65) Prior Publication Data
US 2016/0369306 A1    Dec. 22, 2016

(30) Foreign Application Priority Data
Jul. 3, 2013 (EP) .................................. 13174973

(51) Int. Cl.
| | | |
|---|---|---|
| *C12N 9/88* | (2006.01) | |
| *C12P 7/16* | (2006.01) | |
| *C12N 1/00* | (2006.01) | |
| *C12P 5/02* | (2006.01) | |
| *C12P 7/26* | (2006.01) | |
| *C12N 9/04* | (2006.01) | |
| *C12N 9/02* | (2006.01) | |
| *C12N 15/52* | (2006.01) | |
| *C12P 7/04* | (2006.01) | |
| *C12N 15/70* | (2006.01) | |
| *C12P 19/32* | (2006.01) | |

(52) U.S. Cl.
CPC ............... *C12P 7/16* (2013.01); *C12N 1/00* (2013.01); *C12N 9/001* (2013.01); *C12N 9/0006* (2013.01); *C12N 9/0008* (2013.01); *C12N 9/88* (2013.01); *C12N 15/52* (2013.01); *C12N 15/70* (2013.01); *C12P 5/026* (2013.01); *C12P 7/04* (2013.01); *C12P 7/26* (2013.01); *C12P 19/32* (2013.01); *C12Y 101/0103* (2013.01); *C12Y 101/01034* (2013.01); *C12Y 101/01184* (2013.01); *C12Y 102/0105* (2013.01); *C12Y 103/08001* (2013.01); *C12Y 402/01017* (2013.01); *C12Y 402/01018* (2013.01); *C12Y 402/01055* (2013.01); *C12Y 402/01059* (2013.01); *C12Y 402/01074* (2013.01); *C12Y 402/01116* (2013.01); *C12Y 402/01127* (2013.01); *Y02E 50/10* (2013.01)

(58) Field of Classification Search
CPC ........ C12P 7/16; C12Y 402/01116; C12N 9/88
USPC .................................................. 435/232, 160
See application file for complete search history.

(56) References Cited

U.S. PATENT DOCUMENTS

| | | | |
|---|---|---|---|
| 9,284,581 B2 * | 3/2016 | Burgard ................. | C12N 15/52 |
| 2013/0109064 A1 | 5/2013 | Osterhout et al. | |
| 2014/0141482 A1 * | 5/2014 | Pearlman ................ | C12P 5/026 |
| | | | 435/167 |
| 2016/0186161 A1 * | 6/2016 | Marliere ................. | C12N 9/88 |
| | | | 435/166 |

FOREIGN PATENT DOCUMENTS

| | | |
|---|---|---|
| WO | 2008074794 A1 | 6/2008 |
| WO | 2012174439 A2 | 12/2012 |
| WO | 2013082542 A2 | 6/2013 |

OTHER PUBLICATIONS

Brenda Enzyme Database. Reaction catalyzed by 3-hydroxypropoinyl-CoA dehydratase (4.2.1.116), downloaded from www.brenda-enzymes.info/structure.php?show=reaction&id=49125&type=l&displayType=marvin on Mar. 9, 2017.*
Teufel et al. 3-Hydroxypropionyl-Coenzyme A Dehydratase and Acryloyl-Coenzyme A Reductase, Enzymes of the Autotrophic 3-Hydroxypropionate/4-Hydroxybutyrate Cycle in the Sulfolobales; Journal of Bacteriology, vol. 191, No. 14 (2009) pp. 4572-4581.*
Han et al. Identification of the Polyhydroxyalkanoate (PHA)-Specific Acetoacetyl Coenzyme A Reductase Among Multiple FABG Paralogs in Haloarcula Hispanica and Reconstruction of the PHA Biosynthetic Pathway in Haloferax Volcanii; Applied and Environmental Microbiology, vol. 75, No. 19 (2009) pp. 6168-6175.*
European Search Report received in EP 13 17 4973 dated Mar. 31, 2014.

(Continued)

*Primary Examiner* — Scott Long
*Assistant Examiner* — Paul Martin
(74) *Attorney, Agent, or Firm* — Michele M. Wales; InHouse Patent Counsel, LLC

(57) ABSTRACT

Described is a method for the production of 3-buten-2-one comprising the enzymatic conversion of 4-hydroxy-2-butanone into 3-buten-2-one by making use of an enzyme catalyzing 4-hydroxy-2-butanone dehydration, wherein said enzyme catalyzing 4-hydroxy-2-butanone dehydration is (a) a 3-hydroxypropiony-CoA dehydratase (EC 4.2.1.116), (b) a 3-hydroxybutyryl-CoA dehydratase (EC 4.2.1.55), (c) an enoyl-CoA hydratase (EC 4.2.1.17), (d) a 3-hydroxyoctanoyl-[acyl-carrier-protein] dehydratase (EC 4.2.1.59), (e) a crotonyl-[acyl-carrier-protein] hydratase (EC 4.2.1.58), (f) a 3-hydroxydecanoyl-[acyl-carrier-protein] dehydratase (EC 4.2.1.60), (g) a 3-hydroxypalmitoyl-[acyl-carrier-protein] dehydratase (EC 4.2.1.61), (h) a long-chain-enoyl-CoA hydratase (EC 4.2.1.74), or (i) a 3-methylglutaconyl-CoA hydratase (EC 4.2.1.18). The produced 3-buten-2-one can be further converted into 3-buten-2-ol and finally into 1,3-butadiene.

11 Claims, 6 Drawing Sheets

(56) References Cited

OTHER PUBLICATIONS

Figure 1:
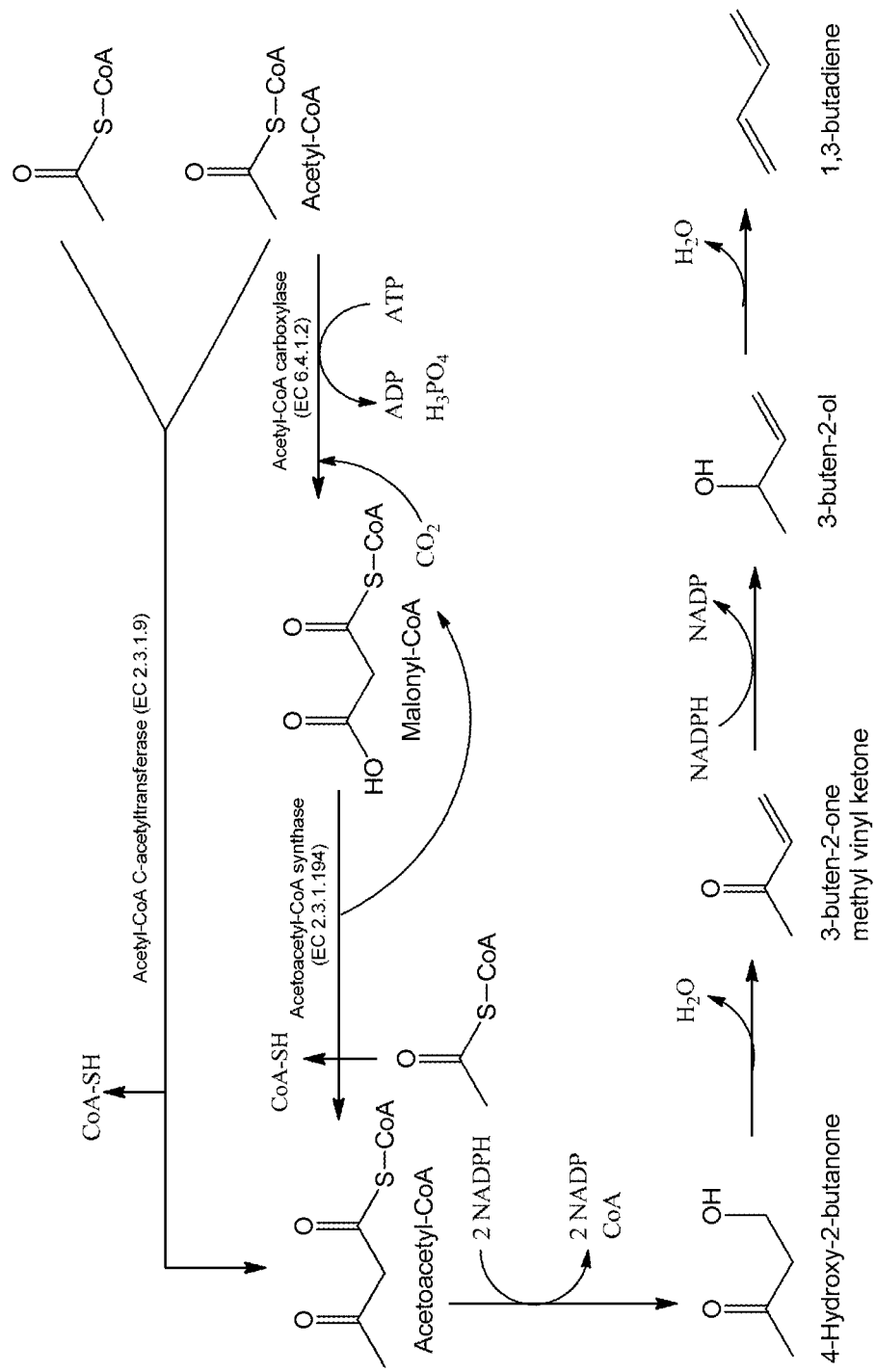

International Search Report received in PCT/EP2014/064102 dated Jan. 7, 2015.
Ichikawa et al., "Synthesis of 3-buten-2-one from 4-hydroxy-2-butanone over anatase-TiO2 catalyst", Elsevier Science, Catalysis Communications, Amsterdam, NL, vol. 6, No. 1, Jan. 1, 2005, XP027680125, pp. 19-22.
International Preliminary Report on Patentability and Written Opinion from corresponding PCT/EP2014/064102, dated Jan. 14, 2016.

* cited by examiner

METHOD FOR THE ENZYMATIC PRODUCTION OF 3-BUTEN-2-ONE

This Application is a 371 National Phase filing of PCT/EP2014/064102 filed Jul. 2, 2014, which claims foreign priority of 13174973.1, filed Jul. 3, 2013, which are all incorporated by reference in their entirety.

The present invention relates to a method for the production of 3-buten-2-one comprising the enzymatic conversion of 4-hydroxy-2-butanone into 3-buten-2-one by making use of an enzyme catalyzing 4-hydroxy-2-butanone dehydration, wherein said enzyme catalyzing 4-hydroxy-2-butanone dehydration is (a) a 3-hydroxypropiony-CoA dehydratase (EC 4.2.1.116), (b) a 3-hydroxybutyryl-CoA dehydratase (EC 4.2.1.55), (c) an enoyl-CoA hydratase (EC 4.2.1.17), (d) a 3-hydroxyoctanoyl-[acyl-carrier-protein] dehydratase (EC 4.2.1.59), (e) a crotonyl-[acyl-carrier-protein] hydratase (EC 4.2.1.58), (f) a 3-hydroxydecanoyl-[acyl-carrier-protein] dehydratase (EC 4.2.1.60), (g) a 3-hydroxypalmitoyl-[acyl-carrier-protein] dehydratase (EC 4.2.1.61), (h) a long-chain-enoyl-CoA hydratase (EC 4.2.1.74), or (i) a 3-methyl-glutaconyl-CoA hydratase (EC 4.2.1.18). The produced 3-buten-2-one can, e.g., be further converted in 3-buten-2-ol and finally into 1,3-butadiene.

Butadiene (1,3-butadiene) is a conjugated diene with the formula $C_4H_6$. It is an important industrial chemical used as a monomer in the production of synthetic rubber. There exist different possibilities to produce butadiene. Butadiene is, for example, produced as a by product of the steam cracking process used to produce ethylene and other olefins. In this process butadiene occurs in the C4 stream and is normally isolated from other by-products by extraction into a polar aprotic solvent, such as acetonitrile, from which it is then stripped. Butadiene can also be produced by the catalytic dehydrogenation of normal butane or it can be produced from ethanol. In the latter case, two different processes are in use. In a single-step process, ethanol is converted to butadiene, hydrogen and water at 400-450° C. over a metal oxide catalyst (Kirshenbaum, I. (1978), Butadiene. In M. Grayson (Ed.), Encyclopedia of Chemical Technology, 3rd ed., Vol. 4, pp. 313-337. New York: John Wiley & Sons). In a two-step process, ethanol is oxidized to acetaldehyde which reacts with additional ethanol over a tantalum-promoted porous silica catalyst at 325-350° C. to yield butadiene (Kirshenbaum, I. (1978), loc cit.). Butadiene can also be produced by catalytic dehydrogenation of normal butenes.

For the past two decades, genetic engineering technologies have made possible the modification of the metabolism of microorganisms, and hence their use to produce key substances which they would otherwise produce at a low yield. By enhancing naturally occurring metabolic pathways, these technologies open up new ways to bio-produce numerous compounds of industrial relevance. Several industrial compounds such as amino acids for animal feed, biodegradable plastics or textile fibres are now routinely produced using genetically modified organisms. There are presently attempts to provide also bio-processes using genetically modified microorganisms for the large-scale production of the major petrochemically derived molecules, in particular butadiene, since no microorganisms are known as natural producers of butadiene even in small quantities. Given the large amounts of rubber produced worldwide and the increasing environmental concerns and the limited resources for producing 1,3-butadiene using chemical processes, there is a need to provide alternative, environmentally-friendly and sustainable processes for the production of 1,3-butadiene and its precursor molecules acetoacetyl-CoA, 4-hydroxy-2-butanone, 3-buten-2-ol and, in particular, 3-buten-2-one. WO 2012/174439 describes methods for producing butadiene from butanols by enzymes which are able to catalyze the conversion of butanols to butadiene. Moreover, WO 2010/144746 describes non-naturally occurring microbial organism having an exogenous nucleic acid encoding a 3-oxobutanol dehydratase which is capable of dehydrating 1,3-oxobutanol to form butanone. However, given the importance of being able to produce compounds such as 1,3-butadiene by microorganisms, there is still a need to identify alternative routes or mechanisms for producing such compounds from renewable resources.

The present invention addresses this need and provides a process by which 3-buten-2-one (also referred to as methyl vinyl ketone) can be produced enzymatically starting from 4-hydroxy-2-butanone by employing certain enzymes. 3-buten-2-one can then further be converted enzymatically to 3-buten-2-ol which can then be further enzymatically converted to 1,3-butadiene. 4-hydroxy-2-butanone can be produced enzymatically from acetoacetyl-CoA while acetoacetyl-CoA can be provided starting from the metabolic intermediate acetyl-Coenzyme A (in the following also referred to as acetyl-CoA) as described herein. The corresponding reactions are schematically shown in FIG. 1.

Thus, the present invention relates to a method for the production of 3-buten-2-one comprising the enzymatic conversion of 4-hydroxy-2-butanone into 3-buten-2-one by making use of an enzyme catalyzing 4-hydroxy-2-butanone dehydration. Enzymes catalyzing 4-hydroxy-2-butanone dehydration which can be employed in this reaction are the following enzymes which are all classified as E.C. 4.2.1._ (i.e., hydro-lyases). Enzymes catalyzing 4-hydroxy-2-butanone dehydration are enzymes which catalyze the following reaction:

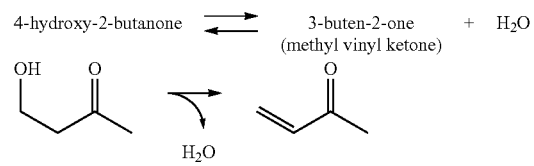

The term "dehydration" is generally referred to a reaction involving the removal of $H_2O$.

According to the present invention an enzyme catalyzing 4-hydroxy-2-butanone dehydration is selected from the group consisting of the following enzymes (a) to (i):
(a) a 3-hydroxypropionyl-CoA dehydratase (EC 4.2.1.116),
(b) a 3-hydroxybutyryl-CoA dehydratase (EC 4.2.1.55),
(c) an enoyl-CoA hydratase (EC 4.2.1.17),
(d) a 3-hydroxyoctanoyl-[acyl-carrier-protein] dehydratase (EC 4.2.1.59),
(e) a crotonyl-[acyl-carrier-protein] hydratase (EC 4.2.1.58),
(f) a 3-hydroxydecanoyl-[acyl-carrier-protein] dehydratase (EC 4.2.1.60),
(g) a 3-hydroxypalmitoyl-[acyl-carrier-protein] dehydratase (EC 4.2.1.61),
(h) a long-chain-enoyl-CoA hydratase (EC 4.2.1.74), and
(i) a 3-methylglutaconyl-CoA hydratase (EC 4.2.1.18).

All these enzymes which are capable of catalyzing 4-hydroxy-2-butanone dehydration have in common that they use a natural substrate having the following minimal structural motif:

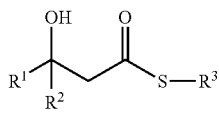

wherein
R¹ is a hydrogen atom or an alkyl group or $CH_2COO^-$,
R² is a hydrogen atom or a methyl group; and
R³ is coenzyme A or acyl-carrier protein.

Thus, the above mentioned enzymes which can catalyze the dehydration of 4-hydroxy-2-butanone can be divided into two groups as follows:

I. $R_3$ in the above shown formula is acyl-carrier protein
  This group includes EC 4.2.1.58, EC 4.2.1.59, EC 4.2.1.60 and EC 4.2.1.61.
  The enzymes of this group have in common that they catalyze a reaction of the following type:

3-hydroxyacyl-[acyl-carrier protein] ⇌ 2-enoyl-[acyl-carrier protein]+$H_2O$

The enzymes of this group share a common structural motif which is referenced in the InterPro as InterPro IPR013114 (http://www.ebi.ac.uk/interpro/entry/IPR013114). The accession number for these enzymes in the Pfam database is PF 07977 (http://pfam.sanger.ac.uk/family/PF07977).

II. $R_3$ in the above shown formula is coenzyme A
  This group includes EC 4.2.1.116, EC 4.2.1.55, EC 4.2.1.17, EC 4.2.1.74 and EC 4.2.1.18
  The enzymes of this group share a common structural motif which is referenced in the InterPRO database as InterPro IPR001753 (http://www.ebi.ac.uk/interpro/entry/IPR001753) and IPR018376 (http://www.ebi.ac.uk/interpro/entry/IPR018376). The accession number for these enzymes in the Pfam database is PF00378 (http://pfam.sanger.ac.uk/family/PF00378).

In one embodiment of the method according to the invention the conversion of 4-hydroxy-2-butanone into 3-buten-2-one is achieved by the use of a 3-hydroxypropionyl-CoA dehydratase (EC 4.2.1.116). 3-hydroxypropionyl-CoA dehydratases (EC 4.2.1.116) catalyze the following reaction:

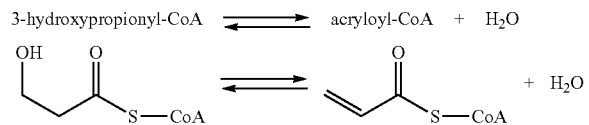

The enzyme is known from various bacteria and archae. Thus, in a preferred embodiment of the invention a bacterial 3-hydroxypropionyl-CoA dehydratase (EC 4.2.1.116) is used, preferably a 3-hydroxypropionyl-CoA dehydratase from a bacterium or an archaebacterium of a genus selected from the group consisting of *Metallosphaera*, *Sulfolobus* and *Brevibacillus* and most preferably from a species selected from the group consisting of *Metallosphaera cuprina*, *Metallosphaera sedula*, *Sulfolobus tokodaii* and *Brevibacillus laterosporus*. Examples for such bacterial 3-hydroxypropionyl-CoA dehydratases are the enzymes from *Metallosphaera cuprina* (Uniprot F4FZ85), *Metallosphaera sedula* (Uniprot A4Y189, Teufel et al., J. Bacteriol. 191 (2009), 4572-4581), *Sulfolobus tokodaii* (Uniprot F9VNG3) and *Brevibacillus laterosporus* (Uniprot F7TTZ1). Amino acid and nucleotide sequences for these enzymes are available. Examples for corresponding amino acid sequences are provided in SEQ ID NOs: 1 to 4 wherein SEQ ID NO:1 is the amino acid sequence of 3-hydroxypropionyl-CoA dehydratase of *M. cuprina*, SEQ ID NO:2 is the amino acid sequence of 3-hydroxypropionyl-CoA dehydratase of *M. sedula*, SEQ ID NO:3 is the amino acid sequence of a 3-hydroxypropionyl-CoA dehydratase of *S. tokodaii* and SEQ ID NO:4 is the amino acid sequence of a 3-hydroxypropionyl-CoA dehydratase of *Brevibacillus laterosporus*.

In a preferred embodiment, the 3-hydroxypropionyl-CoA dehydratase employed in the method of the invention has an amino acid sequence as shown in any one of SEQ ID NOs: 1 to 4 or shows an amino acid sequence which is at least x % homologous to any of SEQ ID NOs: 1 to 4 and has the activity of catalyzing the conversion of 4-hydroxy-2-butanone into 3-buten-2-one, with x being an integer between 30 and 100, preferably 35, 40, 45, 50, 55, 60, 65, 70, 75, 80, 85, 90, 91, 92, 93, 94, 95, 96, 97, 98 or 99.

As shown in the appended Examples, it was found that different tested 3-hydroxypropionyl-CoA dehydratases from different organisms are capable of using 4-hydroxy-2-butanone as a substrate and converting it into 3-buten-2-one. Thus, in principle any 3-hydroxypropionyl-CoA dehydratase can be employed in the method according to the invention. However, it is not only possible to employ in the method of the invention a 3-hydroxypropionyl-CoA dehydratase for converting 4-hydroxy-2-butanone into 3-buten-2-one but also enzymes which show the structural and functional similarities as described above, i.e. enzymes as listed in items (b) to (f), above.

Thus, in another embodiment of the method according to the invention the conversion of 4-hydroxy-2-butanone into 3-buten-2-one is achieved by the use of a 3-hydroxybutyryl-CoA dehydratase (EC 4.2.1.55). 3-hydroxybutyryl-CoA dehydratases (EC 4.2.1.55) catalyze the following reaction:

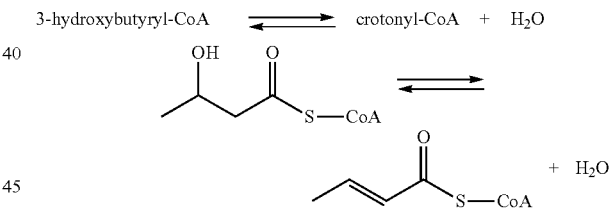

This reaction corresponds to a Michael elimination. 3-hydroxybutyryl-CoA dehydratase belongs to the family of lyases, specifically the hydro-lyases, which cleave carbon-oxygen bonds. The systematic name of this enzyme class is (3R)-3-hydroxybutanoyl-CoA hydro-lyase (crotonoyl-CoA-forming). Other names in common use include D-3-hydroxybutyryl coenzyme A dehydratase, D-3-hydroxybutyryl-CoA dehydratase, enoyl coenzyme A hydratase, and (3R)-3-hydroxybutanoyl-CoA hydro-lyase. This enzyme participates in the butanoate metabolism. Enzymes belonging to this class and catalyzing the above shown conversion of 3-hydroxybutyryl-Coenzyme A into crotonyl-Coenzyme A have been described to occur, e.g. in rat (*Rattus norvegicus*), in *Rhodospirillum rubrum*, in *Sulfolobus acidocaldarius* and in *Acidianus hospitalis*. Nucleotide and/or amino acid sequences for such enzymes have been determined, e.g. for *Aeropyrum pernix*. In principle, any 3-hydroxybutyryl-CoA dehydratase (EC 4.2.1.55) which can catalyze the conversion of 4-hydroxy-2-butanone into 3-buten-2-one can be used in the context of the present invention. In a preferred embodiment of the invention a 3-hydroxybutyryl-CoA dehydratase from an archaebacterium is used, preferably a 3-hydroxybutyryl-CoA dehydratase from an archaebacterium of a genus selected from the group consisting of *Sulfolobus* and *Acidianus* and most preferably from a species selected from the group consisting of *S. acidocaldarius* and *Acidianus hospitalis*. Examples for such bacterial 3-hydroxybutyryl-CoA dehydratases are the enzymes from *Sulfolobus acidocaldarius* (Uniprot Q4J8D5) and from *Acidianus hospitalis* ((Uniprot F4B9R3). Examples for corresponding amino acid sequences are provided in SEQ ID NOs: 5 and 6 wherein SEQ ID NO:5 is the amino acid sequence of 3-hydroxybutyryl-CoA dehydratase of *Sulfolobus acidocaldarius* and SEQ ID NO:6 is the amino acid sequence of 3-hydroxybutyryl-CoA dehydratase of *Acidianus hospitalis*.

In a preferred embodiment, the 3-hydroxybutyryl-CoA dehydratase employed in the method of the invention has an amino acid sequence as shown in SEQ ID NO: 5 or 6 or shows an amino acid sequence which is at least x % homologous to SEQ ID NO: 5 or 6 and has the activity of catalyzing the conversion of 4-hydroxy-2-butanone into 3-buten-2-one, with x being an integer between 30 and 100, preferably 35, 40, 45, 50, 55, 60, 65, 70, 75, 80, 85, 90, 91, 92, 93, 94, 95, 96, 97, 98 or 99.

In another embodiment of the method according to the invention the conversion of 4-hydroxy-2-butanone into 3-buten-2-one is achieved by the use of an enoyl-CoA hydratase (EC 4.2.1.17). Enoyl-CoA hydratases (EC 4.2.1.17) catalyze the following reaction:

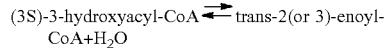

(3S)-3-hydroxyacyl-CoA ⇌ trans-2(or 3)-enoyl-CoA+H$_2$O

Enoyl-CoA hydratase is an enzyme that normally hydrates the double bond between the second and third carbons on acyl-CoA. However, it can also be employed to catalyze the reaction in the reverse direction. This enzyme, also known as crotonase, is naturally involved in metabolizing fatty acids to produce both acetyl-CoA and energy. Enzymes belonging to this class have been described to occur, e.g. in rat (*Rattus norvegicus*), humans (*Homo sapiens*), mouse (*Mus musculus*), wild boar (*Sus scrofa*), *Bos taurus*, *E. coli*, *Clostridium acetobutylicum* and *Clostridium aminobutyricum*. Nucleotide and/or amino acid sequences for such enzymes have been determined, e.g. for rat, humans and *Bacillus subtilis*. In principle, any enoyl-CoA hydratase (EC 4.2.1.17) which can catalyze the conversion of 4-hydroxy-2-butanone into 3-buten-2-one can be used in the context of the present invention.

In another embodiment of the method according to the invention the conversion of 4-hydroxy-2-butanone into 3-buten-2-one is achieved by the use of a 3-hydroxyoctanoyl-[acyl-carrier-protein] dehydratase (EC 4.2.1.59). 3-hydroxyoctanoyl-[acyl-carrier-protein] dehydratases (EC 4.2.1.59) catalyze the following reaction:

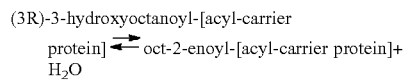

(3R)-3-hydroxyoctanoyl-[acyl-carrier protein] ⇌ oct-2-enoyl-[acyl-carrier protein]+H$_2$O This enzyme belongs to the family of lyases, specifically the hydro-lyases, which cleave carbon-oxygen bonds. The systematic name of this enzyme class is (3R)-3-hydroxyoctanoyl-[acyl-carrier-protein] hydro-lyase (oct-2-enoyl-[acyl-carrier protein]-forming). Other names in common use include D-3-hydroxyoctanoyl-[acyl carrier protein] dehydratase, D-3-hydroxyoctanoyl-acyl carrier protein dehydratase, beta-hydroxyoctanoyl-acyl carrier protein dehydrase, beta-hydroxyoctanoyl thioester dehydratase, beta-hydroxyoctanoyl-ACP-dehydrase, and (3R)-3-hydroxyoctanoyl-[acyl-carrier-protein] hydro-lyase. 3-hydroxyoctanoyl-[acyl-carrier-protein] dehydratases has been described to exist, e.g., in *E. coli* (Mizugaki et al., Biochem. Biophys. Res. Commun. 33 (1968), 520-527). In principle, any 3-hydroxyoctanoyl-[acyl-carrier-protein] dehydratase which can catalyze the conversion of 4-hydroxy-2-butanone into 3-buten-2-one can be used in the context of the present invention. In a preferred embodiment the enzyme from *E. coli* is used in a method according to the present invention.

In another embodiment of the method according to the invention the conversion of 4-hydroxy-2-butanone into 3-buten-2-one is achieved by the use of a crotonoyl-[acyl-carrier-protein] hydratase (EC 4.2.1.58). Crotonoyl-[acyl-carrier-protein] hydratases (EC 4.2.1.58) catalyze the following reaction:

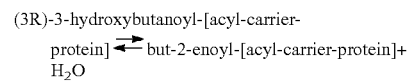

(3R)-3-hydroxybutanoyl-[acyl-carrier-protein] ⇌ but-2-enoyl-[acyl-carrier-protein]+H$_2$O This enzyme belongs to the family of lyases, specifically the hydro-lyases, which cleave carbon-oxygen bonds.

Other names in common use include (3R)-3-hydroxybutanoyl-[acyl-carrier-protein] hydro-lyase, beta-hydroxybutyryl acyl carrier protein dehydratase, beta-hydroxybutyryl acyl carrier protein (ACP) dehydratase, beta-hydroxybutyryl acyl carrier protein dehydratase, enoyl acyl carrier protein hydratase, crotonyl acyl carrier protein hydratase, 3-hydroxybutyryl acyl carrier protein dehydratase, beta-hydroxybutyryl acyl carrier, and protein dehydratase. This enzyme participates in fatty acid biosynthesis. Crotonoyl-[acyl-carrier-protein] hydratase has been described to exist, e.g., in *E. coli* and *Arabidopsis thaliana*. In principle, any crotonoyl-[acyl-carrier-protein] hydratase which can catalyze the conversion of 4-hydroxy-2-butanone into 3-buten-2-one can be used in the context of the present invention. In a preferred embodiment the enzyme from *E. coli* is used in a method according to the present invention.

In another embodiment of the method according to the invention the conversion of 4-hydroxy-2-butanone into 3-buten-2-one is achieved by the use of a 3-hydroxydecanoyl-[acyl-carrier-protein] dehydratase (EC 4.2.1.60). 3-hydroxydecanoyl-[acyl-carrier-protein] dehydratases (EC 4.2.1.60) catalyze the following reactions:

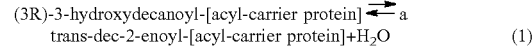

(3R)-3-hydroxydecanoyl-[acyl-carrier protein] ⇌ a trans-dec-2-enoyl-[acyl-carrier protein]+H$_2$O   (1)

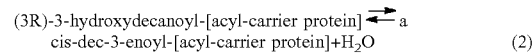

(3R)-3-hydroxydecanoyl-[acyl-carrier protein] ⇌ a cis-dec-3-enoyl-[acyl-carrier protein]+H$_2$O   (2)

The enzyme has been described to exist, e.g., in *Pseudomonas aeruginosa*, *Pseudomonas fluorescens*, *Toxoplasma gondii*, *Plasmodium falciparum*, *Helicobacter pylori*, *Corynebacterium ammoniagenes*, *Enterobacter aerogenes*, *E. coli*, *Proteus vulgaris* and *Salmonella enterica*. In principle, any 3-hydroxydecanoyl-[acyl-carrier-protein] dehydratase which can catalyze the conversion of 4-hydroxy-2-butanone into 3-buten-2-one can be used in the context of the present invention. In a preferred embodiment the enzyme from *E. coli* is used in a method according to the present invention.

In another embodiment of the method according to the invention the conversion of 4-hydroxy-2-butanone into 3-buten-2-one is achieved by the use of a 3-hydroxypalmitoyl-[acyl-carrier-protein] dehydratase (EC 4.2.1.61). 3-hy droxypalmitoyl-[acyl-carrier-protein] dehydratases (EC 4.2.1.61) catalyze the following reaction:

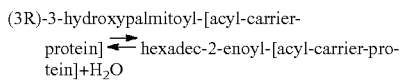

(3R)-3-hydroxypalmitoyl-[acyl-carrier-protein] ⇌ hexadec-2-enoyl-[acyl-carrier-protein]+H₂O This enzyme belongs to the family of lyases, specifically the hydro-lyases, which cleave carbon-oxygen bonds.

Other names in common use include D-3-hydroxypalmitoyl-[acyl-carrier-protein] dehydratase, beta-hydroxypalmitoyl-acyl carrier protein dehydratase, beta-hydroxypalmitoyl thioester dehydratase, beta-hydroxypalmityl-ACP dehydratase, and (3R)-3-hydroxypalmitoyl-[acyl-carrier-protein] hydro-lyase. 3-hydroxypalmitoyl-[acyl-carrier-protein] dehydratase has been described to exist, e.g., in *Candida albicans, Yarrowia lipolytica, S. cerevisiae, s. pombe, Cochliobolus carbonum, Mus musculus, Rattus norvegicus, Bos taurus, Gallus gallus* and *Homo sapiens*. In principle, any 3-hydroxypalmitoyl-[acyl-carrier-protein] dehydratase which can catalyze the conversion of 4-hydroxy-2-butanone into 3-buten-2-one can be used in the context of the present invention.

In another embodiment of the method according to the invention the conversion of 4-hydroxy-2-butanone into 3-buten-2-one is achieved by the use of a long-chain-enoyl-CoA hydratase (EC 4.2.1.74). Long-chain-enoyl-CoA hydratases (EC 4.2.1.74) catalyze the following reaction:

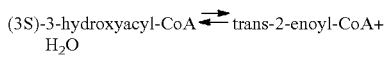

(3S)-3-hydroxyacyl-CoA ⇌ trans-2-enoyl-CoA+H₂O

This enzyme belongs to the family of lyases, specifically the hydro-lyases, which cleave carbon-oxygen bonds. The systematic name of this enzyme class is long-chain-(3S)-3-hydroxyacyl-CoA hydro-lyase. This enzyme is also called long-chain enoyl coenzyme A hydratase and it participates in fatty acid elongation in mitochondria and fatty acid metabolism. This enzyme occurs in a number of organisms, e.g., in *Rattus norvegicus* (Wu et al., Org. Lett. 10 (2008), 2235-2238), *Sus scrofa* and *Cavia porcellus* (Fong and Schulz, J. Biol. Chem. 252 (1977), 542-547; Schulz, Biol. Chem. 249 (1974), 2704-2709) and in principle any long-chain-enoyl-CoA hydratase which can catalyze the conversion of 4-hydroxy-2-butanone into 3-buten-2-one can be employed in the method of the invention.

In another embodiment of the method according to the invention the conversion of 4-hydroxy-2-butanone into 3-buten-2-one is achieved by the use of a 3-methylglutaconyl-CoA hydratase (EC 4.2.1.18). 3-methylglutaconyl-CoA hydratases (EC 4.2.1.18) catalyze the following reaction:

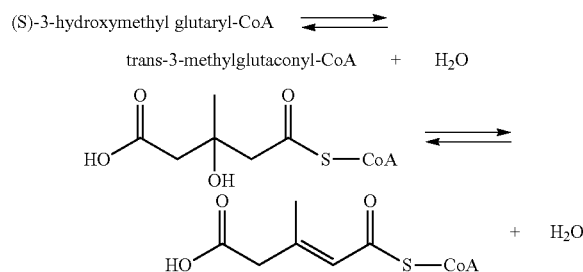

This enzyme occurs in a number of organisms in particular in bacteria, plants and animals. The enzyme has been described, e.g., for *Pseudomonas putida, Acinetobacter* sp. (SwissProt accession number Q3HW12), *Catharanthus roseus, Homo sapiens* (SwissProt accession number Q13825), *Bos taurus* and *Ovis aries* and in principle any 3-methylglutaconyl-CoA hydratase which can catalyze the conversion of 4-hydroxy-2-butanone into 3-buten-2-one can be employed in the method of the invention. The term "3-methylglutaconyl-CoA hydratase" also covers the enzyme encoded by the gene LiuC (Li et al., Angew. Chem. Int. Ed. 52 (2013), p. 1304-1308; Uniprot number Q1 D5Y4) from *Myxococcus xanthus*, preferably from strain DK 1622. The amino acid sequence of this enzyme is shown in SEQ ID NO:25. Although this gene was annotated as a 3-hydroxybutyryl-CoA dehydratase, Li et al. (loc. cit.) showed that its natural substrate is 3-hydroxymethylglutaryl-CoA. In a particularly preferred embodiment any protein can be employed in a method according to the present invention which comprises an amino acid as shown in SEQ ID NO:25 or an amino acid sequence which is at least x % homologous SEQ ID NO: 25 and which has the activity of a 3-methylglutaconyl-CoA hydratase/3-hydromethylglutaryl-CoA dehydratase and which shows the activity of converting 4-hydroxy-2-butanone into 3-buten-2-one, with x being an integer between 30 and 100, preferably 35, 40, 45, 50, 55, 60, 65, 70, 75, 80, 85, 90, 91, 92, 93, 94, 95, 96, 97, 98 or 99.

As described above, the 4-hydroxy-2-butanone to be converted into 3-buten-2-one can be provided by the enzymatic conversion of acetoacetyl-CoA into 4-hydroxy-2-butanone. Thus, the present invention also relates to a method for the production of 3-buten-2-one comprising the enzymatic conversion of 4-hydroxy-2-butanone into 3-buten-2-one by making use of an enzyme catalyzing 4-hydroxy-2-butanone dehydration as described above wherein said method further comprises the enzymatic conversion of acetoacetyl-CoA into said 4-hydroxy-2-butanone by making use of an acetoacetyl-CoA reductase.

The enzymatic conversion of acetoacetyl-CoA into 4-hydroxy-2-butanone by making use of an acetoacetyl-CoA reductase may be accomplished by a two step conversion which comprises (1) the enzymatic conversion of acetoacetyl-CoA into acetoacetaldehyde and (2) the subsequent enzymatic conversion of acetoacetaldehyde into 4-hydroxy-2-butanone.

The first step may occur according to the following scheme:

Acetoacetyl-CoA+NADH+H⁺ ⇌ Acetoacetaldehyde+NAD⁺ or

Acetoacetyl-CoA+NADPH+H⁺ ⇌ Acetoacetaldehyde+NADP⁺

The second step may occur according to the following scheme:

Acetoacetaldehyde+NADH+H⁺ ⇌ 4-Hydroxy-2-butanone+NAD⁺ or

Acetoacetaldehyde+NADPH+H⁺ ⇌ 4-Hydroxy-2-butanone+NADP⁺

In principle any enzyme which can catalyze such a conversion can be employed. Examples for corresponding enzymes are hydroxymethylglutaryl-CoA reductase (EC 1.1.1.34) or short-chain dehydrogenases/fatty acyl-CoA reductase.

Thus, in one embodiment of the method according to the invention the conversion of acetoacetyl-CoA into 4-hydroxy-2-butanone is achieved by employing a hydroxymethylglutaryl-CoA reductase (EC 1.1.1.34). This enzyme normally catalyzes the following reaction

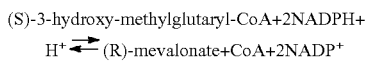

(S)-3-hydroxy-methylglutaryl-CoA+2NADPH+
H⁺ ⇌ (R)-mevalonate+CoA+2NADP⁺

Enzymes belonging to this class and catalyzing the above shown conversion occur in organisms of all kingdoms, i.e. plants, animals, fungi, bacteria etc. and have extensively been described in the literature. Nucleotide and/or amino acid sequences for such enzymes have been determined for numerous organisms, in particular bacterial organisms. In principle, any hydroxymethylglutaryl-CoA reductase (EC 1.1.1.34) which can catalyze the conversion of acetoacetyl-CoA into 4-hydroxy-2-butanone can be used in the context of the present invention.

Alternatively or in addition, the above described conversion of acetoacetyl-CoA into 4-hydroxy-2-butanone can also be achieved by using an enzyme referred to as a short-chain dehydrogenases/fatty acyl-CoA reductase. The term "short-chain dehydrogenase/fatty acyl-CoA reductase" or "short-chain dehydrogenases/reductase (SDR)" in the context of the present invention refers to enzymes which are characterized by the following features:

1. They catalyze a two-step reaction in which fatty acyl-CoA is reduced to fatty alcohol.
2. They show a substrate specificity for acyl-CoA containing an aliphatic chain from 8 to 20 carbon atoms.

Preferably such enzymes are furthermore characterized by the feature that they show a specific motif in their primary structure, i.e. amino acid sequence, namely they show two specific glycine motifs for NADP(H) binding.

The short-chain dehydrogenase/fatty acyl-CoA reductase or short-chain dehydrogenases/reductases (SDR) enzymes constitute a family of enzymes, most of which are known to be NAD- or NADP-dependent oxidoreductase (Jornvall H. et al., Biochemistry 34 (1995), 6003-6013). Recently, a novel bacterial NADP-dependent reductase from *Marinobacter aquaeolei* VT8 was characterized (Willis et al., Biochemistry 50 (2011), 10550-10558). This enzyme catalyzes the four-electron reduction of fatty acyl-CoA substrates to the corresponding fatty alcohols.

The enzymatic conversion of fatty acyl-CoA into fatty alcohol occurs through an aldehyde intermediate according to the following scheme:

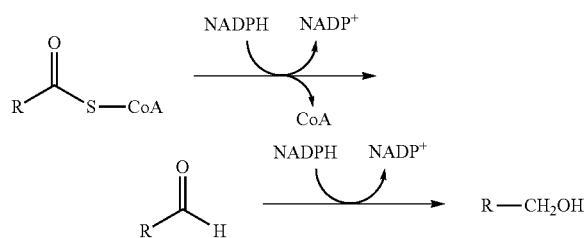

The enzyme displays activity on fatty acyl-CoA substrates ranging from 8 to 20 carbons in length (both saturated and unsaturated) as well as on fatty aldehyde substrates. Characteristically, proteins of this family possess two NAD(P)(H)-binding motifs, which have the conserved sequence GXGX(1-2X)G (Willis et al., Biochemistry 50 (2011), 10550-10558; Jornvall H. et al., Biochemistry 34 (1995), 6003-6013). The first pattern, GTGFIG, is identified near the N-terminus and the second signature sequence, GXXXGXG, is located between residues 384-390.

In principle any "short-chain dehydrogenase/fatty acyl-CoA reductase" or "short-chain dehydrogenases/reductases (SDR)" can be applied in the method according to the invention.

Preferably, the short-chain dehydrogenase/fatty acyl-CoA reductase is a short-chain dehydrogenase/fatty acyl-CoA reductase from a marine bacterium, preferably from the genus *Marinobacter* or *Hahella*, even more preferably from the species *Marinobacter aquaeolei*, more preferably *Marinobacter aquaeolei* VT8, *Marinobacter manganoxydans*, *Marinobacter algicola*, *Marinobacter* sp. ELB17 or *Hahella chejuensis*. Examples of such enzymes are the short-chain dehydrogenase/fatty acyl-CoA reductase from *Marinobacter aquaeolei* VT8 (Uniprot accession number A1U3L3, Willis et al., Biochemistry 50 (2011), 10550-10558), the short-chain dehydrogenase from *Marinobacter manganoxydans* (Uniprot accession number G6YQS9), the short-chain dehydrogenase from *Marinobacter algicola* (Uniprot accession number A6EUH6), the short-chain dehydrogenase from *Marinobacter* sp. ELB17 (Uniprot accession number A3JCC5) and the short-chain dehydrogenase from *Hahella chejuensis* (Uniprot accession number Q2SCE0).

The sequence of the short-chain dehydrogenase/fatty acyl-CoA reductase from *Marinobacter aquaeolei* VT8 is shown in SEQ ID NO: 7. The sequence of the short-chain dehydrogenase/fatty acyl-CoA reductase from *Marinobacter manganoxydans* is shown in SEQ ID NO: 8. The sequence of the short-chain dehydrogenase/fatty acyl-CoA reductase from *Marinobacter* sp. ELB17 is shown in SEQ ID NO: 9. The sequence of the short-chain dehydrogenase/fatty acyl-CoA reductase from *Marinobacter algicola* is shown in SEQ ID NO: 10. The sequence of the short-chain dehydrogenase/fatty acyl-CoA reductase from *Hahella chejuensis* is shown in SEQ ID NO: 11. The sequence of the short-chain dehydrogenase/fatty acyl-CoA reductase from *Marinobacter* sp. Bss20148 is shown in SEQ ID NO: 20. The sequence of the short-chain dehydrogenase/fatty acyl-CoA reductase from *Marinobacter adhaerens* (strain HP15) is shown in SEQ ID NO: 21. The sequence of the short-chain dehydrogenase/fatty acyl-CoA reductase from *Marinobacter santoriniensis* NKSG1 is shown in SEQ ID NO: 22. The sequence of the short-chain dehydrogenase/fatty acyl-CoA reductase from *Marinobacter lipolyticus* SM19 is shown in SEQ ID NO: 23. The sequence of the short-chain dehydrogenase/fatty acyl-CoA reductase from *Marinobacter hydrocarbonoclasticus* ATCC 49840 is shown in SEQ ID NO: 24. In a particularly preferred embodiment any protein can be employed in a method according to the present invention which shows an amino acid sequence as shown in any one of SEQ ID NOs: 7 to 11 and SEQ ID NOs: 20 to 24 or an amino acid sequence which is at least x % homologous to any of SEQ ID NOs: 7 to 11 and SEQ NOs: 20 to 24 and which has the activity of a short-chain dehydrogenase/fatty acyl-CoA reductase, i.e., an activity of converting acetoacetyl-CoA into 4-hydroxy-2-butanone, with x being an integer between 30 and 100, preferably 35, 40, 45, 50, 55, 60, 65, 70, 75, 80, 85, 90, 91, 92, 93, 94, 95, 96, 97, 98 or 99.

As is evident from the appended Examples, it was found that different tested short-chain dehydrogenase/reductase proteins from different organisms are capable of using acetoacetyl-CoA as a substrate and converting it into 4-hydroxy-2-butanone.

The present invention also relates to a method as described herein above, in which acetoacetyl-CoA is converted into 4-hydroxy-2-butanone which is then further converted into 3-buten-2-one and which further comprises the step of enzymatically providing the acetoacetyl-CoA. This can be achieved by the enzymatic conversion of two molecules acetyl-CoA into one molecule of acetoacetyl-CoA. Such methods have already been described, e.g., in WO 2013/057194. Thus, according to the present invention, acetyl-CoA can, for example, be converted into acetoacetyl-CoA by the following reaction:

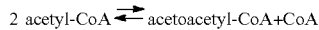
2 acetyl-CoA ⇌ acetoacetyl-CoA+CoA

This reaction is catalyzed by enzymes called acetyl-CoA C-acetyltransferases which are classified as EC 2.3.1.9. Enzymes belonging to this class and catalyzing the above shown conversion of two molecules of acetyl-CoA into acetoacetyl-CoA and CoA occur in organisms of all kingdoms, i.e. plants, animals, fungi, bacteria etc. and have extensively been described in the literature. Nucleotide and/or amino acid sequences for such enzymes have been determined for a variety of organisms, like *Homo sapiens, Arabidopsis thaliana, E. coli, Bacillus subtilis* and *Candida*, to name just some examples. In principle, any acetyl-CoA C-acetyltransferase (EC 2.3.1.9) can be used in the context of the present invention.

Alternatively, the provision of acetoacetyl-CoA may also be achieved by the enzymatic conversion of acetyl-CoA and malonyl-CoA into acetoacetyl-CoA according to the following reaction.

acetyl-CoA+malonyl-CoA→acetoacetyl-CoA+CoA+ CO$_2$

This reaction is catalyzed by an enzyme called acetoacetyl-CoA synthase (EC 2.3.1.194). The gene encoding this enzyme was identified in the mevalonate pathway gene cluster for terpenoid production in a soil-isolated Gram-positive *Streptomyces* sp. Strain CL190 (Okamura et al., PNAS USA 107 (2010), 11265-11270, 2010). Moreover a biosynthetic pathway using this enzyme for acetoacetyl-CoA production was recently developed in *E. coli* (Matsumoto K et al., Biosci. Biotechnol. Biochem, 75 (2011), 364-366).

Accordingly, in a preferred embodiment, in the methods of the invention further comprising the enzymatic conversion of acetyl-CoA into acetoacetyl-CoA, the enzymatic conversion of acetyl-CoA into said acetoacetyl-CoA consists of a single enzymatic reaction in which acetyl-CoA is directly converted into acetoacetyl-CoA. Preferably, the enzymatic conversion of acetyl-CoA into acetoacetyl-CoA is achieved by making use of an acetyl-CoA acetyltransferase (EC 2.3.1.9) as described above.

In another preferred embodiment, in the methods of the invention further comprising the enzymatic conversion of acetyl-CoA into acetoacetyl-CoA, the enzymatic conversion of acetyl-CoA into said acetoacetyl-CoA comprises two enzymatic steps of
(i) enzymatically converting acetyl-CoA into malonyl-CoA; and
(ii) enzymatically converting malonyl-CoA and acetyl-CoA into acetoacetyl-CoA.

Preferably, the enzymatic conversion of acetyl-CoA into malonyl-CoA is achieved by the use of an acetyl-CoA carboxylase (EC 6.4.1.2). This enzyme catalyzes the following reaction:

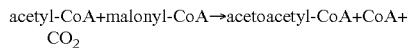
Acetyl-CoA+ATP+CO$_2$→Malonyl-CoA+ADP

Preferably, the enzymatic conversion of malonyl-CoA and acetyl-CoA into acetoacetyl-CoA is achieved by the use of an acetoacetyl-CoA synthase (EC 2.3.1.194).

In principle, any acetyl-CoA acetyltransferase (EC 2.3.1.9), acetyl-CoA carboxylase (EC 6.4.1.2) and/or acetoacetyl-CoA synthase (EC 2.3.1.194) can be applied in the method according to the invention.

The 3-buten-2-one produced according to any method as described herein can be further converted into 3-buten-2-ol, which in itself may serve as a substrate for the production of 1,3-butadiene as described further below. Thus, a method according to the present invention as described above may further include the step of the enzymatic conversion of the produced 3-buten-2-one into 3-buten-2-ol by making use of a 3-buten-2-one reductase. Enzymes which can act as a 3-buten-2-one reductase, are, e.g., enzymes which are classified as EC 1.1.1 or enzymes which can be classified into E.C. 1.1.1 due to their characteristics, such as short-chain dehydrogenases/fatty acyl-CoA reductases, in particular those from marine bacteria.

In principle any possible enzyme classified in EC 1.1.1 which can catalyze the conversion of 3-buten-2-one into 3-buten-2-ol can be employed in a method according to the invention. Examples of preferred enzymes are alcohol dehydrogenases, such as alcohol dehydrogenases classified as EC 1.1.1.1, alcohol dehydrogenase (NADP$^+$) classified as EC 1.1.1.2 and allyl alcohol dehydrogenases classified as EC 1.1.1.54, as well as carbonyl reductases (EC 1.1.1.184).

Alcohol dehydrogenases are enzymes which are a group of dehydrogenase enzymes that occur in many organisms and facilitate the interconversion between alcohols and aldehydes or ketones. In one preferred embodiment, the 3-buten-2-one reductase catalyzing the enzymatic conversion of 3-buten-2-one into 3-buten-2-ol is an alcohol dehydrogenase (EC 1.1.1.1). In principle, any alcohol dehydrogenase classified as EC 1.1.1.1 which can catalyze the conversion of 3-buten-2-one into 3-buten-2-ol can be employed in a method according to the present invention. Alcohol dehydrogenases (EC 1.1.1.1) are a group of dehydrogenase enzymes that occur in many organisms and facilitate the interconversion between alcohols and aldehydes or ketones with the reduction of nicotinamide adenine dinucleotide (NAD$^+$ to NADH). In humans and many other animals, they serve to break down alcohols that otherwise are toxic, and they also participate in generation of useful aldehyde, ketone, or alcohol groups during biosynthesis of various metabolites. In yeast, plants, and many bacteria, some alcohol dehydrogenases catalyze the opposite reaction as part of fermentation to ensure a constant supply of NAD$^+$. Enzymes belonging to this class and catalyzing the above shown conversion occur in organisms of all kingdoms, i.e. plants, animals, fungi, bacteria etc. and have extensively been described in the literature. For example, enzymes from *Homo sapiens, Mus musculus, Drosophila melanogaster, Sacharomyces cerevisiae, Schizosasccharomyces pombe, Rhodobacter ruber, Pseudomonas aeruginosa*, and *Brassica napus* have been identified and characterized. Nucleotide and/or amino acid sequences for such enzymes have been determined for numerous organisms, in particular bacterial organisms. In principle, any alcohol dehydrogenase (EC 1.1.1.1) which can catalyze the conversion of 3-buten-2-one into 3-buten-2-ol can be used in the context of the present invention. Indeed, as exemplified in the examples, it was found that different tested alcohol dehydrogenases from different organisms are capable of using 3-buten-2-one as a substrate and converting it into 3-buten-2-ol.

In another embodiment, the 3-buten-2-one reductase catalyzing the enzymatic conversion of 3-buten-2-one into 3-buten-2-ol is an alcohol dehydrogenase (NADP$^+$) (EC 1.1.1.2). In principle, any alcohol dehydrogenase (NADP$^+$)

classified as EC 1.1.1.2 which can catalyze the conversion of 3-buten-2-one into 3-buten-2-ol can be employed in a method according to the present invention.

Alcohol dehydrogenases (NADP$^+$) (EC 1.1.1.2) are a group of dehydrogenase enzymes that occur in many organisms and facilitate the interconversion between alcohols and aldehydes or ketones with the reduction of nicotinamide adenine dinucleotide (NADP$^+$ to NADPH). Enzymes belonging to this class and catalyzing the above shown conversion occur in organisms of all kingdoms, i.e. plants, animals, fungi, bacteria etc. and have extensively been described in the literature. For example, enzymes from *Bos taurus, Mus musculus, Homo sapiens, Lactobacillus brevis, Escherichia coli, Sacharomyces cerevisiae*, and *Drosophila melanogaster* have been identified and characterized. Nucleotide and/or amino acid sequences for such enzymes have been determined for numerous organisms. In principle, any alcohol dehydrogenase (NADP$^+$) (EC 1.1.1.2) which can catalyze the conversion of 3-buten-2-one into 3-buten-2-ol can be used in the context of the present invention. As shown in the Examples, it was found that an alcohol dehydrogenase (NADP$^+$) is capable of using 3-buten-2-one as a substrate and converting it into 3-buten-2-ol.

In a preferred embodiment, an alcohol dehydrogenase employed in a method according to the invention is of bacterial origin. More preferably it is an alcohol dehydrogenase from a bacterium of the genus *Rhodococcus, Thermoanaerobium* or *Lactobacillus*, even more preferably from the species *Rhodococcus ruber, Thermoanaerobium brockii, Lactobacillus brevis* or *Lactobacillus kefiri*.

In particularly preferred embodiments the alcohol dehydrogenase is a secondary alcohol dehydrogenase derived from *Rhodococcus ruber* (Uniprot Q8KLT9; Karabec et al., Chem. Commun. 46 (2010), 6314-6316), an alcohol dehydrogenase derived from *Thermoanaerobacter brockii* (*Thermoanaerobium brockii*) (Uniprot P14941; Keinan et al., J. Am. Chem. Soc. 108 (1986), 162-169), an R-specific alcohol dehydrogenase derived from *Lactobacillus brevis* (Uniprot Q84EX5; Schlieben et al., J. Mol. Biol. 349 (2005), 801-813), an NADH-dependent (S)-specific alcohol dehydrogenase derived from *Lactobacillus kefiri* (Uniprot B5AXN9; Chen et al., Appl. Biochem. Biotechnol. 160 (2010), 19-29) or an NADH-dependent (S)-specific alcohol dehydrogenase derived from *Lactobacillus brevis* (Uniprot C2D0H5).

Also preferred is an NADPH dependent R-specific alcohol dehydrogenase derived from *Lactobacillus kefiri* (Uniprot Q6WVP7, Bradshaw et al., J. Org. Chem. 57 (1992), 1532-1536).

Amino acid and nucleotide sequences for the above-mentioned enzymes are available. Examples for corresponding amino acid sequences are provided in SEQ ID NOs: 12 to 17 wherein SEQ ID NO:12 is the amino acid sequence of a secondary alcohol dehydrogenase derived from *Rhodococcus ruber*, SEQ ID NO:13 is the amino acid sequence of an alcohol dehydrogenase derived from *Thermoanaerobacter brockii* (*Thermoanaerobium brockii*) (Uniprot P14941), SEQ ID NO:14 is the amino acid sequence of an R-specific alcohol dehydrogenase derived from *Lactobacillus brevis* (Uniprot Q84EX5), SEQ ID NO:15 is the amino acid sequence of an NADH-dependent (S)-specific alcohol dehydrogenase derived from *Lactobacillus kefiri* (Uniprot B5AXN9) and SEQ ID NO:16 is the amino acid sequence of an NADH-dependent (S)-specific alcohol dehydrogenase derived from *Lactobacillus brevis* (Uniprot C2D0H5).

SEQ ID NO:17 is the amino acid sequence of an NADPH dependent R-specific alcohol dehydrogenase derived from *Lactobacillus kefiri* (Uniprot Q6WVP7).

In a particularly preferred embodiment any protein can be employed in a method according to the present invention which shows an amino acid sequence as shown in any one of SEQ ID NOs: 12 to 17 or an amino acid sequence which is at least x % homologous to any of SEQ ID NOs: 12 to 17 and which has the activity of converting 3-buten-2-one into 3-buten-2-ol, with x being an integer between 30 and 100, preferably 35, 40, 45, 50, 55, 60, 65, 70, 75, 80, 85, 90, 91, 92, 93, 94, 95, 96, 97, 98 or 99.

In another preferred embodiment, the conversion of 3-buten-2-one into 3-buten-2-ol is achieved by employing an allyl alcohol dehydrogenase (EC 1.1.1.54). Allyl alcohol dehydrogenases (EC 1.1.1.54) catalyze the following reaction:

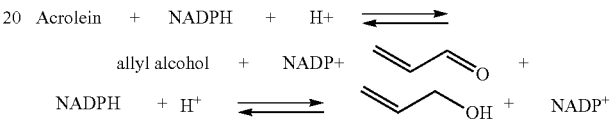

In principle, any allyl alcohol dehydrogenase classified as EC 1.1.1.54 which can catalyze the conversion of 3-buten-2-one into 3-buten-2-ol can be employed in a method according to the present invention. This enzyme belongs to the family of oxidoreductases, specifically those acting on the CH—OH group of donor with NAD$^+$ or NADP$^+$ as acceptor. The systematic name of this enzyme class is often referred to as allyl-alcohol:NADP$^+$ oxidoreductase. Enzymes belonging to this class and catalyzing the above shown conversion have been described to occur in various organisms and have been described in the literature. For example, enzymes from *Pseudomonas putida* and *Escherichia coli* have been identified and characterized. In principle, any allyl alcohol dehydrogenase (EC 1.1.1.54) which can catalyze the conversion of 3-buten-2-one into 3-buten-2-ol can be used in the context of the present invention.

In another preferred embodiment, the 3-buten-2-one reductase catalyzing the enzymatic conversion of 3-buten-2-one into 3-buten-2-ol is a carbonyl reductase (EC 1.1.1.184).

A carbonyl reductase (EC 1.1.1.184) catalyzes the following reaction:

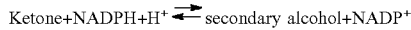

This enzyme belongs to the family of oxidoreductases, specifically those acting on the CH—OH group of donor with NAD$^+$ or NADP$_+$ as acceptor. The systematic name of this enzyme class is secondary-alcohol:NADP$^+$ oxidoreductase. Other names in common use include aldehyde reductase 1, prostaglandin 9-ketoreductase, xenobiotic ketone reductase, NADPH-dependent carbonyl reductase, ALR3, carbonyl reductase, nonspecific NADPH-dependent carbonyl reductase, aldehyde reductase 1, and carbonyl reductase (NADPH). This enzyme participates in arachidonic acid metabolism, and has been shown to catabolize S-Nitrosoglutathione, as a means to degrade NO in an NADPH dependent manner. Enzymes belonging to this class and catalyzing the above shown conversion have been described to occur in many organisms and have extensively been described in the literature. For example, enzymes from *Rattus norvegicus, Homo sapiens, Drosophila melanogaster, Saccharomyces cerevisiae* and *Candida magnoliae* have been identified and characterized. In principle, any carbonyl reductase which can catalyze the enzymatic conversion of 3-buten-2-one into 3-buten-2-ol can be used in the context of the present invention. As is evident from the appended examples, it was found that a carbonyl reductase showed the reduction activity towards 3-buten-2-one in the presence of NADPH as co-factor.

In a preferred embodiment the carbonyl reductase employed in a method according to the invention is derived from a mammal, preferably from a rodent, even more preferably from a rodent of the genus Rattus and most preferably from Rattus norvegicus. An example for such an enzyme is the carbonyl reductase from Rattus norvegicus (Uniprot B2GV72; Okamoto et al., IUBMB Life 48 (1999), 543-547). Amino acid and nucleotide sequences for carbonyl reductases are available. SEQ ID NO:18 is the amino acid sequence of a carbonyl reductase derived from Rattus norvegicus (Uniprot B2GV72).

In a particularly preferred embodiment any protein can be employed in a method according to the present invention which shows an amino acid sequence as shown in SEQ ID NO: 18 or an amino acid sequence which is at least x % homologous to any of SEQ ID NOs: 18 and which has the activity of catalyzing the conversion of 3-buten-2-one into 3-buten-2-ol, with x being an integer between 30 and 100, preferably 35, 40, 45, 50, 55, 60, 65, 70, 75, 80, 85, 90, 91, 92, 93, 94, 95, 96, 97, 98 or 99.

Alternatively, in another aspect, the 3-buten-2-one reductase catalyzing the enzymatic conversion of 3-buten-2-one into 3-buten-2-ol, may be a short chain dehydrogenase/fatty acyl-CoA reductase. These enzymes, i.e., the short-chain dehydrogenases/fatty acyl-CoA reductase, in particular fatty acyl-CoA reductases derived from marine bacteria, have already been described above and the same as has been set forth above also applies here, in particular as regards the preferred embodiments.

In the Examples it is shown that short-chain dehydrogenases/fatty acyl-CoA reductases can be employed for converting 3-buten-2-one into 3-buten-2-ol. In preferred embodiments of the method according to the invention an enzyme originating from a bacterium is employed, preferably from a marine bacterium, preferably from the genus Marinobacter or Hahella, most preferably from the species Hahella chejuensis. In a particularly preferred embodiment, the enzyme employed is the one showing the amino acid sequence as reflected in Uniprot Q2SCEO.

The 3-buten-2-ol produced by a method as described herein-above may be further converted into 1,3-butadiene, in particular via an enzymatic conversion, i.e. by making use of an alkenol dehydratase. Thus, the present invention also relates to a method for the production of 1,3-butadiene comprising:
(a) producing 3-buten-2-ol according to a method of the invention as described herein-above, and
(b) the step of enzymatically converting the thus produced 3-buten-2-ol into 1,3-butadiene.

An enzyme which is capable of converting 3-buten-2-ol into 1,3-butadiene is referred to in this context as an alkenol dehydratase.

An example of an alkenol dehydratase to be employed in a method according to the present invention is the enzyme which has been designated "linalool dehydratase-isomerase" and which has been identified in Castellaniella defragrans (formerly Alcaligenes defragrans) strain 65Phen (Brodkorb et al., J. Biol. Chem. 285 (2010), 30436-30442). Linalool dehydratase-isomerase is a bifunctional enzyme which is involved in the anaerobic degradation of monoterpenes. The native enzyme has been found to have a molecular mass of 160 kDa and is assumed to be a homotetramer of 40 kDa subunits. The enzyme catalyzes in vitro two reactions in both directions depending on the thermodynamic driving forces. On the one hand, the enzyme catalyzes the isomerisation of the primary allyl alcohol geraniol into its stereoisomer linalool which bears a tertiary allyl alcohol motif. On the other hand, the enzyme catalyzes the water secession (dehydration) from the tertiary alcohol linalool to the corresponding acyclic monoterpene beta-myrcene, a molecule bearing a conjugated diene motif. In Castellaniella defragrans the protein is expressed as a precursor protein with a signal peptide for a periplasmatic location which is cleaved after transport through the membrane. The enzyme is classified as EC 4.2.1.127. A linalool dehydratase-isomerase has the capacity to catalyze the following reaction under anaerobic conditions:

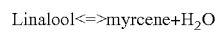

Linalool<=>myrcene+H$_2$O

This activity can, e.g., be measured with an assay as described in Brodkorb et al. (loc. cit.). In such an assay, vials are prewarmed at 35° C., anoxic protein solution is transferred into the vials and DTT is added to 2 mM. The reaction mixtures are sealed with a butyl septum and the headspace is flushed with CO$_2$/N$_2$ (10/90 (v/v)). The reaction is started by adding a distinct concentration of linalool and incubated at 35° C. The conversion of linalool into myrcene is assessed by investigating the production of myrcene, e.g. by gas chromatography.

In a preferred embodiment, a linalool dehydratase-isomerase also has the capacity to catalyze the isomerisation of geraniol into linalool under anaerobic conditions:

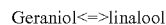

Geraniol<=>linalool

This activity can, e.g., be measured with an assay as described in Brodkorb et al. (loc. cit.). In such an assay, vials are prewarmed at 35° C., anoxic protein solution is transferred into the vials and DTT is added to 2 mM. The reaction mixtures are sealed with a butyl septum and the headspace is flushed with CO$_2$/N$_2$ (10/90 (v/v)). The reaction is started by adding a distinct concentration of geraniol and incubated at 35° C. The conversion of geraniol into linalool is assessed by investigating the production of myrcene, i.e. the product of the second reaction catalyzed by the enzyme, e.g. by gas chromatography.

Geraniol, linalool and myrcene are acyclic C$_{10}$-terpenoids produced by plants, belonging to the class of allyl alcohols and hydrocarbons, respectively. Lüddecke and Harder (Z. Naturforsch. 66c (2011), 409-412) reported on a high substrate specificity of linalool dehydratase-isomerase. It has been shown that linalool dehydratase-isomerase can act on but-3-en-2-ol and convert it into butadiene.

An example of a sequence of an alkenol dehydratase which can be employed in the method according to the present invention is given in SEQ ID NO: 19. A sequence for an alkenol dehydratase is also accessible in the UniProtKB/TrEMBL database under accession number E1XUJ2. These sequences represent an alkenol dehydratase which is classified as a linalool dehydratase-isomerase. In a preferred embodiment the method according to the present invention makes use of an alkenol dehydratase comprising the amino acid sequence shown in SEQ ID NO: 19 or a sequence which is at least x % identical to SEQ ID NO: 19 and which is able to catalyze the conversion of 3-buten-2-ol into 1,3-butadiene, with x being an integer between 30 and 100, preferably 35, 40, 45, 50, 55, 60, 65, 70, 75, 80, 85, 90, 91, 92, 93, 94, 95, 96, 97, 98 or 99.

The term "an alkenol dehydratase" as used in the present invention therefore in particular refers to an enzyme which shows the above indicated degree of sequence identity with SEQ ID NO: 19 and which can catalyze the conversion of 3-buten-2-ol into 1,3-butadiene. By using the sequence of SEQ ID NO: 19 or corresponding encoding nucleotide sequences, it is possible for the skilled person to identify further alkenol dehydratases which can catalyze the above indicated conversion.

Finally, the present invention also relates to a method for the production of 3-buten-2-ol comprising the enzymatic conversion of 4-hydroxy-2-butanone into 3-buten-2-one by making use of an enzyme catalyzing 4-hydroxy-2-butanone dehydration and the enzymatic conversion of 3-buten-2-one into 3-buten-2-ol by making use of a 3-buten-2-one reductase. The enzyme catalyzing 4-hydroxy-2-butanone dehydration is not particularly limited to a specific enzyme as described herein above but can be any possible enzyme which can catalyze this conversion. In a preferred embodiment, the enzyme catalyzing 4-hydroxy-2-butanone dehydration is an enzyme as described above. Moreover, the enzyme converting 3-buten-2-one into 3-buten-2-ol by making use of a 3-buten-2-one reductase is not particularly limited to a specific enzyme but may, in a preferred embodiment, be an enzyme as described above in the context of the fourth aspect of the present invention.

When referring to "homology" in connection with amino acid or nucleotide sequences, reference is preferably made to sequence identity. The degree of sequence identity can be determined according to methods well known in the art using preferably suitable computer algorithms such as CLUSTAL.

When using the Clustal analysis method to determine whether a particular sequence is, for instance, at least 60% identical to a reference sequence default settings may be used or the settings are preferably as follows: Matrix: blosum 30; Open gap penalty: 10.0; Extend gap penalty: 0.05; Delay divergent: 40; Gap separation distance: 8 for comparisons of amino acid sequences. For nucleotide sequence comparisons, the Extend gap penalty is preferably set to 5.0.

In a preferred embodiment ClustalW2 is used for the comparison of amino acid sequences. In the case of pairwise comparisons/alignments, the following settings are preferably chosen: Protein weight matrix: BLOSUM 62; gap open: 10; gap extension: 0.1. In the case of multiple comparisons/alignments, the following settings are preferably chosen: Protein weight matrix: BLOSUM 62; gap open: 10; gap extension: 0.2; gap distance: 5; no end gap.

Preferably, the degree of identity is calculated over the complete length of the sequence. When the sequences which are compared do not have the same length, the degree of identity either refers to the percentage of residues in the shorter sequence which are identical to residues in the longer sequence or to the percentage of residues in the longer sequence which are identical to residues in the shorter sequence. Preferably, it refers to the percentage of residues in the shorter sequence which are identical to residues in the longer sequence The methods according to the present invention may be carried out in vitro or in vivo. An in vitro reaction is understood to be a reaction in which no cells are employed, i.e. an acellular reaction. Thus, in vitro preferably means in a cell-free system. The term "in vitro" in one embodiment means in the presence of isolated enzymes (or enzyme systems optionally comprising possibly required cofactors). In one embodiment, the enzymes employed in the method are used in purified form.

For carrying out the method in vitro the substrates for the reaction and the enzymes are incubated under conditions (buffer, temperature, cosubstrates, cofactors etc.) allowing the enzymes to be active and the enzymatic conversion to occur. The reaction is allowed to proceed for a time sufficient to produce the respective product. The production of the respective products can be measured by methods known in the art, such as gas chromatography possibly linked to mass spectrometry detection.

The enzymes may be in any suitable form allowing the enzymatic reaction to take place. They may be purified or partially purified or in the form of crude cellular extracts or partially purified extracts. It is also possible that the enzymes are immobilized on a suitable carrier. In a preferred embodiment, at least one of the enzymes employed in such an in vitro reaction according to the present invention is a non-naturally occurring enzyme, e.g., a variant of an enzyme which does not as such occur in nature. Such variants include, for example, mutants, in particular prepared by molecular biological methods, which show improved properties, such as a higher enzyme activity, higher substrate specificity, higher temperature resistance and the like.

In one embodiment of the method according to the invention the substrate which is used in such an in vitro method is 4-hydroxy-2-butanone which is converted by the use of the above-mentioned enzymes to 3-buten-2-one. In another embodiment, the substrate used in such an in vitro method is acetoacetyl-CoA which is first converted into 4-hydroxy-2-butanone as described above which is then in turn converted into 3-buten-2-one as described above. In another embodiment, the substrate used in such an in vitro method is acetyl-CoA which is first converted into acetoacetyl-CoA as described above which is then converted into 4-hydroxy-2-butanone as described above which is then in turn converted into 3-buten-2-one as described above.

The in vitro method according to the invention may be carried out in a one-pot-reaction, i.e. the substrate is combined in one reaction mixture with the above described enzymes necessary for the conversion into 3-buten-2-one, 3-buten-2-ol or 1,3-butadiene, respectively, and the reaction is allowed to proceed for a time sufficient to produce the respective product. Alternatively, the method may also be carried out by effecting one or more enzymatic steps in a consecutive manner, i.e. by first mixing the substrate with one or more enzymes and allowing the reaction to proceed to an intermediate and then adding one or more further enzymes to convert the intermediate further either into an intermediate or into butadiene.

The in vitro method according to the invention furthermore may comprise the step of collecting the product(s), preferably the gaseous products, in particular 1,3-butadiene, degassing out of the reaction, i.e. recovering the products from the culture or, in the case of gaseous products the products which degas, e.g., out of the culture. Thus, in one embodiment, the method is carried out in the presence of a system for collecting a gaseous product, such as butadiene, under gaseous form during the reaction.

As a matter of fact, 1,3-butadiene, adopts the gaseous state at room temperature and atmospheric pressure. The method according to the invention therefore does not necessarily require extraction of the product from the reaction mixture, a step which is always very costly when performed at industrial scale. The evacuation and storage of butadiene and its possible subsequent physical separation from other gaseous substances as well as its chemical conversion can be performed according to any method known to one of skill in the art. For example, butadiene can be separated from $CO_2$ by the condensation of $CO_2$ at low temperatures. $CO_2$ can also be removed by polar solvents, e.g. ethanolamine. Moreover, it can be isolated by adsorption on a hydrophobic membrane.

In another embodiment the method according to the invention is carried out in culture, in the presence of an organism, preferably a microorganism, producing at least one of the enzymes described above which are necessary to produce 3-buten-2-one according to one of the methods of the invention. Moreover, in another embodiment the method according to the invention is carried out in culture, in the presence of an organism, preferably a microorganism, producing at least one of the enzymes described above which are necessary to produce 3-buten-2-ol according to one of the methods of the invention. Moreover, in another embodiment the method according to the invention is carried out in culture, in the presence of an organism, preferably a microorganism, producing at least one of the enzymes described above which are necessary to produce 1,3-butadiene according to one of the method of the invention.

Thus, in such embodiments of the invention, an organism, preferably a microorganism, that produces at least one of the enzymes specified in the description, above, is used. It is possible to use a (micro)organism which naturally produces one or more of the required enzymes and to genetically modify such a (micro)organism so that it expresses also those enzymes which it does not naturally express.

If a (micro)organism is used which naturally expresses one of the required enzyme activities, it is possible to modify such a (micro)organism so that this activity is overexpressed in the (mircro)organism. This can, e.g., be achieved by effecting mutations in the promoter region of the corresponding gene so as to lead to a promoter which ensures a higher expression of the gene. Alternatively, it is also possible to mutate the gene as such so as to lead to an enzyme showing a higher activity.

By using (micro)organisms which express the enzymes which are necessary for achieving the enzymatic conversions as described above, it is possible to carry out the method according to the invention directly in the culture medium, without the need to separate or purify the enzymes.

In one embodiment the organism employed in the method according to the invention is an organism, preferably a microorganism, which has been genetically modified to contain one or more foreign nucleic acid molecules encoding one or more of the enzymes as described above. The term "foreign" in this context means that the nucleic acid molecule does not naturally occur in said organism/microorganism. This means that it does not occur in the same structure or at the same location in the organism/microorganism. In one preferred embodiment, the foreign nucleic acid molecule is a recombinant molecule comprising a promoter and a coding sequence encoding the respective enzyme in which the promoter driving expression of the coding sequence is heterologous with respect to the coding sequence. Heterologous in this context means that the promoter is not the promoter naturally driving the expression of said coding sequence but is a promoter naturally driving expression of a different coding sequence, i.e., it is derived from another gene, or is a synthetic promoter or a chimeric promoter. Preferably, the promoter is a promoter heterologous to the organism/microorganism, i.e. a promoter which does naturally not occur in the respective organism/microorganism. Even more preferably, the promoter is an inducible promoter. Promoters for driving expression in different types of organisms, in particular in microorganisms, are well known to the person skilled in the art.

In a further embodiment the nucleic acid molecule is foreign to the organism/microorganism in that the encoded enzyme is not endogenous to the organism/microorganism, i.e. is naturally not expressed by the organism/microorganism when it is not genetically modified. In other words, the encoded enzyme is heterologous with respect to the organism/microorganism. The foreign nucleic acid molecule may be present in the organism/microorganism in extrachromosomal form, e.g. as a plasmid, or stably integrated in the chromosome. A stable integration is preferred. Thus, the genetic modification can consist, e.g. in integrating the corresponding gene(s) encoding the enzyme(s) into the chromosome, or in expressing the enzyme(s) from a plasmid containing a promoter upstream of the enzyme-coding sequence, the promoter and coding sequence preferably originating from different organisms, or any other method known to one of skill in the art.

Genetically modified organisms are organisms which do not naturally occur, i.e., which cannot be found in nature, and which differ substantially from naturally occurring organisms due to the introduction of a foreign nucleic acid molecule. Such non-naturally occurring organisms are preferably employed in a method according to the present invention carried out in vivo.

The organisms used in the invention can be prokaryotes or eukaryotes, preferably, they are microorganisms such as bacteria, yeasts, fungi or molds, or plant cells or animal cells. In a particular embodiment, the microorganisms are bacteria, preferably of the genus *Escherichia* or *Bacillus* and even more preferably of the species *Escherichia coli* or *Bacillus subtilis*.

It is also possible to employ an extremophilic bacterium such as *Thermus thermophilus*, or anaerobic bacteria from the family Clostridiae.

In one embodiment the microorganism is a fungus, more preferably a fungus of the genus *Saccharomyces, Schizosaccharomyces, Aspergillus, Trichoderma, Pichia* or *Kluyveromyces* and even more preferably of the species *Saccharomyces cerevisiae, Schizosaccharomyces pombe, Aspergillus niger, Trichoderma reesei, Pichia pastoris* or of the species *Kluyveromyces lactis*.

In another embodiment, the method according to the invention makes use of a photosynthetic microorganism expressing at least the enzymes which are necessary for achieving the enzymatic conversions as described above. Preferably, the microorganism is a photosynthetic bacterium, or a microalgae. In a further embodiment the microorganism is an algae, more preferably an algae belonging to the diatomeae.

In another embodiment, it is possible to use a microorganism which belongs to the group of acetogenic bacteria which are capable of converting CO (or $CO_2+H_2$) to produce acetyl-CoA via the so-called Wood-Ljungdahl pathway (Köpke et al.; PNAS 10 (2010), 13087-13092). A fermentation process using such microorganisms is known as syngas fermentation. Strictly mesophilic anaerobes such as *C. ljungdahlii, C. aceticum, Acetobacterium woodii, C. autoethanogenum*, and *C. carboxydeviron*, are frequently being used in syngas fermentation (Munasingheet et al.; Bioresource Technology 101 (2010), 5013-5022).

It is also conceivable to use in the method according to the invention a combination of (micro)organisms wherein different (micro)organisms express different enzymes as described above.

In another embodiment the method according to the invention makes use of a multicellular organism expressing at least one of the enzymes which are necessary for achieving the enzymatic conversions as described above. Examples for such organisms are plants or animals.

In a particular embodiment, the method according to the invention involves culturing microorganisms in standard culture conditions (30-37° C. at 1 atm, in a fermenter allowing aerobic growth of the bacteria) or non-standard conditions (higher temperature to correspond to the culture conditions of thermophilic organisms, for example).

In a further embodiment the method of the invention is carried out under microaerophilic conditions. This means that the quantity of injected air is limiting so as to minimize residual oxygen concentrations in the gaseous effluents containing butadiene.

In another embodiment the method according to the invention furthermore comprises the step of collecting the product either from the culture or, in the case of a gaseous product, like, 1,3-butadiene degassing out of the reaction, from the culture off-gas. Thus in a preferred embodiment, the method is carried out in the presence of a system for collecting a product, for example, a gaseous product, such as 1,3-butadiene, under gaseous form during the reaction.

As a matter of fact, 1,3-butadiene adopts the gaseous state at room temperature and atmospheric pressure. The method according to the invention therefore does not necessarily require extraction of butadiene from the liquid culture medium, a step which is always very costly when performed at industrial scale. The evacuation and storage of butadiene and its possible subsequent physical separation and chemical conversion can be performed according to any method known to one of skill in the art and as described above.

In a particular embodiment, the method also comprises detecting a gaseous product, such as butadiene, which is present in the gaseous phase. The presence of, e.g., butadiene in an environment of air or another gas, even in small amounts, can be detected by using various techniques and in particular by using gas chromatography systems with infrared or flame ionization detection, or by coupling with mass spectrometry.

When the method according to the invention is carried out in vivo by using an organism/microorganism providing the respective enzyme activities, the organism, preferably microorganism, is cultivated under suitable culture conditions allowing the occurrence of the enzymatic reaction. The specific culture conditions depend on the specific organism/microorganism employed but are well known to the person skilled in the art. The culture conditions are generally chosen in such a manner that they allow the expression of the genes encoding the enzymes for the respective reactions. Various methods are known to the person skilled in the art in order to improve and fine-tune the expression of certain genes at certain stages of the culture such as induction of gene expression by chemical inducers or by a temperature shift.

In another embodiment, the method of the invention comprises the step of providing the organism, preferably the microorganism carrying the respective enzyme activity or activities in the form of a (cell) culture, preferably in the form of a liquid cell culture, a subsequent step of cultivating the organism, preferably the microorganism in a fermenter (often also referred to a bioreactor) under suitable conditions allowing the expression of the respective enzyme and further comprising the step of effecting an enzymatic conversion of a method of the invention as described herein above. Suitable fermenter or bioreactor devices and fermentation conditions are known to the person skilled in the art. A bioreactor or a fermenter refers to any manufactured or engineered device or system known in the art that supports a biologically active environment. Thus, a bioreactor or a fermenter may be a vessel in which a chemical/biochemical process like the method of the present invention is carried out which involves organisms, preferably microorganisms and/or biochemically active substances, i.e., the enzyme(s) described above derived from such organisms or organisms harbouring the above described enzyme(s). In a bioreactor or a fermenter, this process can either be aerobic or anaerobic. These bioreactors are commonly cylindrical, and may range in size from liters to cubic meters, and are often made of stainless steel. In this respect, without being bound by theory, the fermenter or bioreactor may be designed in a way that it is suitable to cultivate the organisms, preferably microorganisms, in, e.g., a batch-culture, feed-batch-culture, perfusion culture or chemostate-culture, all of which are generally known in the art.

The culture medium can be any culture medium suitable for cultivating the respective organism or microorganism.

As described above, such a method according to the present invention may also comprise the step of recovering the produced product from the culture medium and/or the fermentation off-gas.

In another embodiment the organism employed in the method according to the invention is a plant. In principle any possible plant can be used, i.e. a monocotyledonous plant or a dicotyledonous plant. It is preferable to use a plant which can be cultivated on an agriculturally meaningful scale and which allows to produce large amounts of biomass. Examples are grasses like *Lolium*, cereals like rye, wheat, barley, oat, millet, maize, other starch storing plants like potato or sugar storing plants like sugar cane or sugar beet. Conceivable is also the use of tobacco or of vegetable plants such as tomato, pepper, cucumber, egg plant etc. Another possibility is the use of oil storing plants such as rape seed, olives etc. Also conceivable is the use of trees, in particular fast growing trees such as *eucalyptus*, poplar or rubber tree (Hevea *brasiliensis*).

As described above, it is possible to use in the method according to the invention a (micro)organism which is genetically modified so as to contain a nucleic acid molecule encoding at least one of the which are necessary for achieving the enzymatic conversions as described above. Such a nucleic acid molecule encoding an enzyme as described above can be used alone or as part of a vector. The nucleic acid molecules can further comprise expression control sequences operably linked to the polynucleotide comprised in the nucleic acid molecule. The term "operatively linked" or "operably linked", as used throughout the present description, refers to a linkage between one or more expression control sequences and the coding region in the polynucleotide to be expressed in such a way that expression is achieved under conditions compatible with the expression control sequence.

Expression comprises transcription of the heterologous DNA sequence, preferably into a translatable mRNA. Regulatory elements ensuring expression in fungi as well as in bacteria, are well known to those skilled in the art. They encompass promoters, enhancers, termination signals, targeting signals and the like. Examples are given further below in connection with explanations concerning vectors.

Promoters for use in connection with the nucleic acid molecule may be homologous or heterologous with regard to its origin and/or with regard to the gene to be expressed. Suitable promoters are for instance promoters which lend themselves to constitutive expression. However, promoters which are only activated at a point in time determined by external influences can also be used. Artificial and/or chemically inducible promoters may be used in this context.

The vectors can further comprise expression control sequences operably linked to said polynucleotides contained in the vectors. These expression control sequences may be suited to ensure transcription and synthesis of a translatable RNA in bacteria or fungi.

In addition, it is possible to insert different mutations into the polynucleotides by methods usual in molecular biology (see for instance Sambrook and Russell (2001), Molecular Cloning: A Laboratory Manual, CSH Press, Cold Spring Harbor, N.Y., USA), leading to the synthesis of polypeptides possibly having modified biological properties. The introduction of point mutations is conceivable at positions at which a modification of the amino acid sequence for instance influences the biological activity or the regulation of the polypeptide.

Moreover, mutants possessing a modified substrate or product specificity can be prepared. Preferably, such mutants show an increased activity. Furthermore, the introduction of mutations into the polynucleotides encoding an enzyme as defined above allows the gene expression rate and/or the activity of the enzymes encoded by said polynucleotides to be optimized.

For genetically modifying bacteria or fungi, the polynucleotides encoding an enzyme as defined above or parts of these molecules can be introduced into plasmids which permit mutagenesis or sequence modification by recombination of DNA sequences. Standard methods (see Sambrook and Russell (2001), Molecular Cloning: A Laboratory Manual, CSH Press, Cold Spring Harbor, N.Y., USA) allow base exchanges to be performed or natural or synthetic sequences to be added. DNA fragments can be connected to each other by applying adapters and linkers to the fragments. Moreover, engineering measures which provide suitable restriction sites or remove surplus DNA or restriction sites can be used. In those cases, in which insertions, deletions or substitutions are possible, in vitro mutagenesis, "primer repair", restriction or ligation can be used. In general, a sequence analysis, restriction analysis and other methods of biochemistry and molecular biology are carried out as analysis methods.

The polynucleotide introduced into a (micro)organism is expressed so as to lead to the production of a polypeptide having any of the activities described above. An overview of different expression systems is for instance contained in Methods in Enzymology 153 (1987), 385-516, in Bitter et al. (Methods in Enzymology 153 (1987), 516-544) and in Sawers et al. (Applied Microbiology and Biotechnology 46 (1996), 1-9), Billman-Jacobe (Current Opinion in Biotechnology 7 (1996), 500-4), Hockney (Trends in Biotechnology 12 (1994), 456-463), Griffiths et al., (Methods in Molecular Biology 75 (1997), 427-440). An overview of yeast expression systems is for instance given by Hensing et al. (Antonie van Leuwenhoek 67 (1995), 261-279), Bussineau et al. (Developments in Biological Standardization 83 (1994), 13-19), Gellissen et al. (Antonie van Leuwenhoek 62 (1992), 79-93, Fleer (Current Opinion in Biotechnology 3 (1992), 486-496), Vedvick (Current Opinion in Biotechnology 2 (1991), 742-745) and Buckholz (Bio/Technology 9 (1991), 1067-1072).

Expression vectors have been widely described in the literature. As a rule, they contain not only a selection marker gene and a replication-origin ensuring replication in the host selected, but also a bacterial or viral promoter, and in most cases a termination signal for transcription. Between the promoter and the termination signal there is in general at least one restriction site or a polylinker which enables the insertion of a coding DNA sequence. The DNA sequence naturally controlling the transcription of the corresponding gene can be used as the promoter sequence, if it is active in the selected host organism. However, this sequence can also be exchanged for other promoter sequences. It is possible to use promoters ensuring constitutive expression of the gene and inducible promoters which permit a deliberate control of the expression of the gene. Bacterial and viral promoter sequences possessing these properties are described in detail in the literature. Regulatory sequences for the expression in microorganisms (for instance E. coli, S. cerevisiae) are sufficiently described in the literature. Promoters permitting a particularly high expression of a downstream sequence are for instance the T7 promoter (Studier et al., Methods in Enzymology 185 (1990), 60-89), lacUV5, trp, trp-lacUV5 (DeBoer et al., in Rodriguez and Chamberlin (Eds), Promoters, Structure and Function; Praeger, New York, (1982), 462-481; DeBoer et al., Proc. Natl. Acad. Sci. USA (1983), 21-25), lp1 rac (Boros et al., Gene 42 (1986), 97-100). Inducible promoters are preferably used for the synthesis of polypeptides. These promoters often lead to higher polypeptide yields than do constitutive promoters. In order to obtain an optimum amount of polypeptide, a two-stage process is often used. First, the host cells are cultured under optimum conditions up to a relatively high cell density. In the second step, transcription is induced depending on the type of promoter used. In this regard, a tac promoter is particularly suitable which can be induced by lactose or IPTG (=isopropyl-β-D-thiogalactopyranoside) (deBoer et al., Proc. Natl. Acad. Sci. USA 80 (1983), 21-25). Termination signals for transcription are also described in the literature.

The transformation of the host cell with a polynucleotide or vector according to the invention can be carried out by standard methods, as for instance described in Sambrook and Russell (2001), Molecular Cloning: A Laboratory Manual, CSH Press, Cold Spring Harbor, N.Y., USA; Methods in Yeast Genetics, A Laboratory Course Manual, Cold Spring Harbor Laboratory Press, 1990. The host cell is cultured in nutrient media meeting the requirements of the particular host cell used, in particular in respect of the pH value, temperature, salt concentration, aeration, antibiotics, vitamins, trace elements etc.

The present invention also relates to an organism, preferably a microorganism, which is able to express the above described enzymes required for the conversion of 4-hydroxy-2-butanone into 3-buten-2-one and for the conversion of 3-buten-2-one into 3-buten-2-ol. Thus, the present invention relates to an organism or microorganism which expresses (i) an enzyme catalyzing 4-hydroxy-2-butanone dehydration as defined above, and (ii) a 3-buten-2-one reductase as defined above.

In a preferred embodiment, the above organism is an organism wherein the 3-buten-2-one reductase is (a) a carbonyl reductase (EC 1.1.1.184), (b) an alcohol dehydrogenase, or (c) a short chain dehydrogenase/fatty acyl-CoA reductase as defined above.

In a further aspect, the organisms is an organism which further expresses an alkenol dehydratase enzyme as defined above.

In yet a further aspect, the organism is an organism which further expresses (i) an acetoacetyl-CoA reductase; or
(ii) an acetoacetyl-CoA reductase and enzymes capable of converting acetyl-CoA into acetoacetyl-CoA as defined above.

As regards the preferred embodiments of the enzymes which the organism expresses, the same applies as has been set forth above in connection with the method according to the invention.

In one embodiment an organism according to the present invention is a recombinant organism in the sense that it is genetically modified due to the introduction of at least one nucleic acid molecule encoding at least one of the above mentioned enzymes. Preferably such a nucleic acid molecule is heterologous with regard to the organism which means that it does not naturally occur in said organism. Accordingly, the organism according to the present invention is preferably a non-naturally occurring organism which differs from a naturally occurring organism due to the introduction of a foreign nucleic acid molecule.

The microorganism is preferably a bacterium, a yeast or a fungus. In another preferred embodiment the organism is a plant or non-human animal. As regards other preferred embodiments, the same applies as has been set forth above in connection with the method according to the invention.

The present invention also relates to a composition comprising an organism according to the invention and, optionally, acetoacetyl-CoA, 4-hydroxy-2-butanone, 3-buten-2-one and/or 3-buten-2-ol.

Thus, the present invention relates in a preferred embodiment to a composition comprising an organism, preferably a microorganism, producing at least one of the enzymes described above which are necessary to produce 3-buten-2-one according to a method of the invention. Optionally, such a composition further comprises acetoacetyl-CoA and/or 4-hydroxy-2-butanone. Moreover, in another embodiment, the present invention relates to a composition comprising an organism, preferably a microorganism, producing at least one of the enzymes described above which are necessary to produce 3-buten-2-ol according to a method of the invention. Optionally, such a composition further comprises acetoacetyl-CoA, 4-hydroxy-2-butanone and/or 3-buten-2-one. Moreover, in another embodiment, the present invention relates to a composition comprising an organism, preferably a microorganism, producing at least one of the enzymes described above which are necessary to produce 1,3-butadiene according to a method of the invention. Optionally, such a composition further comprises acetoacetyl-CoA, 4-hydroxy-2-butanone, 3-buten-2-one and/or 3-buten-2-ol.

As regards preferred embodiments of the above compositions, the same applies as has been set forth above in connection with the method according to the invention.

The present invention also relates to the use of an enzyme catalyzing 4-hydroxy-2-butanone dehydration as described herein-above for the production of 3-buten-2-one from 4-hydroxy-2-butanone.

The present invention also relates to the use of a combination of at least one enzyme catalyzing 4-hydroxy-2-butanone dehydration as described above and of at least one enzyme catalyzing the enzymatic conversion of acetoacetyl-CoA into 4-hydroxy-2-butanone as described above for the production of 3-buten-2-one from acetoacetyl-CoA.

The present invention also relates to the use of a combination of at least one enzyme catalyzing 4-hydroxy-2-butanone dehydration as described above and of at least one enzyme catalyzing the enzymatic conversion of acetoacetyl-CoA into 4-hydroxy-2-butanone as described above and of at least one enzyme catalyzing the enzymatic conversion of acetyl-CoA into acetoacetyl-CoA as described above for the production of 3-buten-2-one from acetyl-CoA.

As regards the preferred embodiments of the enzymes applied in the uses for the production of 3-buten-2-one, the same applies as has been set forth above in connection with the method according to the invention.

The present invention also relates to the use of a combination of at least one enzyme catalyzing the enzymatic conversion of 3-buten-2-one into 3-buten-2-ol as described above in combination with at least one enzyme catalyzing 4-hydroxy-2-butanone dehydration as described above for the production of 3-buten-2-ol from 4-hydroxy-2-butanone.

The present invention also relates to the use of a combination of at least one enzyme catalyzing the enzymatic conversion of 3-buten-2-one into 3-buten-2-ol as described above in combination with at least one enzyme catalyzing 4-hydroxy-2-butanone dehydration into 3-buten-2-one as described above and at least one enzyme catalyzing the enzymatic conversion of acetoacetyl-CoA into 4-hydroxy-2-butanone as described above for the production of 3-buten-2-ol from acetoacetyl-CoA.

The present invention also relates to the use of a combination of at least one enzyme catalyzing the enzymatic conversion of 3-buten-2-one into 3-buten-2-ol as described above in combination with at least one enzyme catalyzing 4-hydroxy-2-butanone dehydration into 3-buten-2-one as described above and at least one enzyme catalyzing the enzymatic conversion of acetoacetyl-CoA into 4-hydroxy-2-butanone as described above and at least one enzyme catalyzing the enzymatic conversion of acetyl-CoA into acetoacetyl-CoA as described above for the production of 3-buten-2-ol from acetyl-CoA.

As regards the preferred embodiments of the enzymes applied in the uses for the production of 3-buten-2-one, the same applies as has been set forth above in connection with the method according to the invention.

The present invention also relates to the use of a combination of at least one enzyme catalyzing the enzymatic conversion of 3-buten-2-ol into 1,3-butadiene as described and at least one enzyme catalyzing the enzymatic conversion of 3-buten-2-one into 3-buten-2-ol as described above for the production of 1,3-butadiene from 3-butene-2-one.

The present invention also relates to the use of a combination of at least one enzyme catalyzing the enzymatic conversion of 3-buten-2-ol into 1,3-butadiene as described above and at least one enzyme catalyzing the enzymatic conversion of 3-buten-2-one into 3-buten-2-ol as described above in combination with at least one enzyme catalyzing 4-hydroxy-2-butanone dehydration into 3-buten-2-one as described above for the production of 1,3-butadiene from 4-hydroxy-2-butanone.

The present invention also relates to the use of a combination of at least one enzyme catalyzing the enzymatic conversion of 3-buten-2-ol into 1,3-butadiene as described above and at least one enzyme catalyzing the enzymatic conversion of 3-buten-2-one into 3-buten-2-ol as described above in combination with at least one enzyme catalyzing 4-hydroxy-2-butanone dehydration into 3-buten-2-one as described above and at least one enzyme catalyzing the enzymatic conversion of acetoacetyl-CoA into 4-hydroxy-2-butanone as described above for the production of 1,3-butadiene from acetoacetyl-CoA.

The present invention also relates to the use of a combination of at least one enzyme catalyzing the enzymatic conversion of 3-buten-2-ol into 1,3-butadiene as described above and at least one enzyme catalyzing the enzymatic conversion of 3-buten-2-one into 3-buten-2-ol as described above in combination with at least one enzyme catalyzing 4-hydroxy-2-butanone dehydration into 3-buten-2-one as described above and at least one enzyme catalyzing the enzymatic conversion of acetoacetyl-CoA into 4-hydroxy-2-butanone as described above and at least one enzyme catalyzing the enzymatic conversion of acetyl-CoA into acetoacetyl-CoA as described above for the production of 1,3-butadiene from acetyl-CoA.

As regards the preferred embodiments of the enzymes applied in the uses for the production of 1,3-butadiene, the same applies as has been set forth above in connection with the method according to the invention.

The present invention also relates to the use of at least one enzyme catalyzing the enzymatic conversion of acetoacetyl-CoA into 4-hydroxy-2-butanone as described above for the production of 4-hydroxy-2-butanone from acetoacetyl-CoA.

The present invention also relates to the use of a combination of at least one enzyme catalyzing the enzymatic conversion of acetoacetyl-CoA into 4-hydroxy-2-butanone as described above and at least one enzyme for the enzymatic conversion of acetyl-CoA into acetoacetyl-CoA as described above for the production of 4-hydroxy-2-butanone from acetyl-CoA.

As regards the preferred embodiments of the enzymes applied in the uses for the production of 4-hydroxy-2-butanone, the same applies as has been set forth above in connection with the method according to the invention.

FIG. 1: shows an artificial metabolic pathway for 1,3-butadiene production from acetyl-CoA via 3-buten-2-ol.

Figure 2:
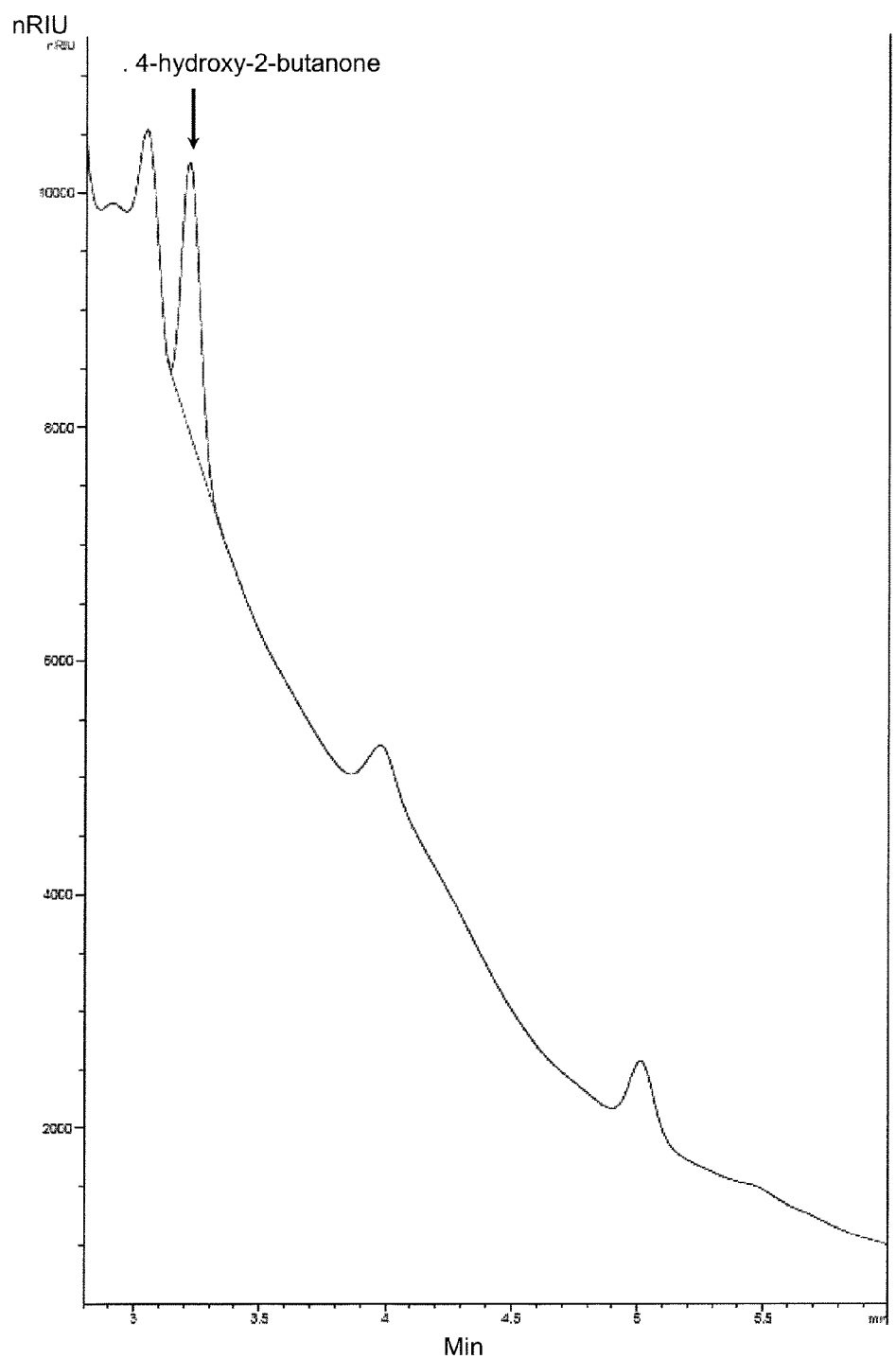

FIG. 2: shows a chromatogram obtained for the enzyme-catalyzed reduction of acetoacetyl-CoA with the short chain alcohol dehydrogenase-like protein from *H. chejuensis* as outlined in Example 3. The assay was performed with 32 mM acetoacetyl-CoA and incubated for 2 hours.

Figure 3:
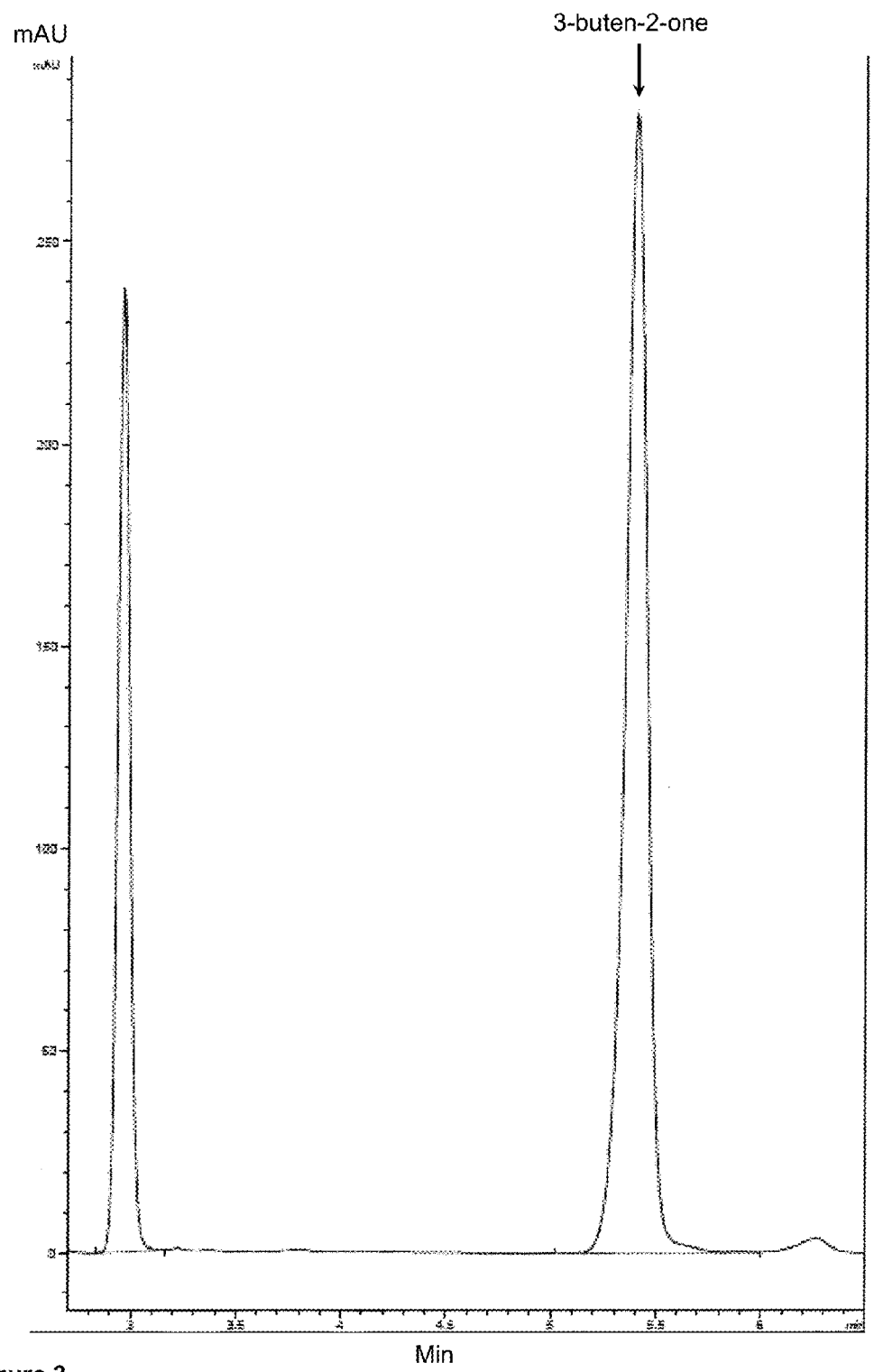

FIG. 3: shows a chromatogram obtained for the enzymatic dehydration of 4-hydroxy-2-butanone with 3-hydroxypropionyl-CoA dehydratase from *S. tokodaii* as outlined in Example 5. The assay was performed with 100 mM 4-hydroxy-2-butanone and incubated for 24 hours.

Figure 4:
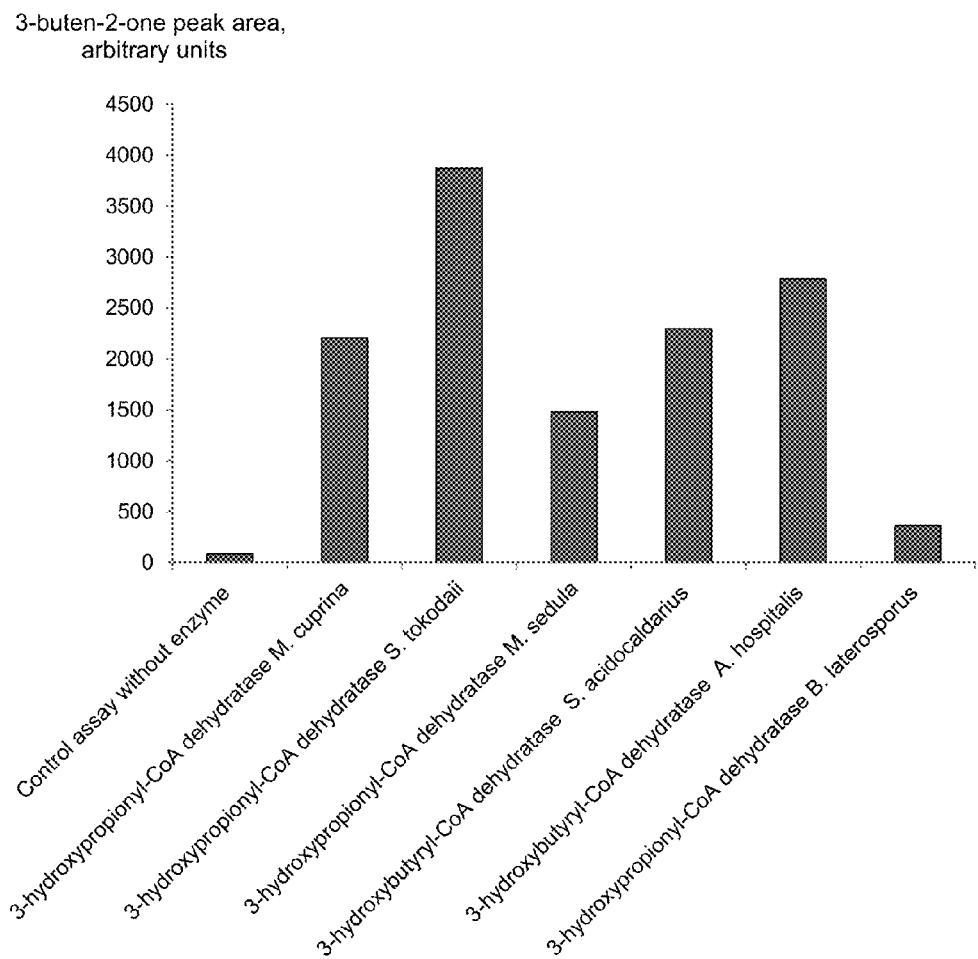

FIG. 4: shows 3-buten-2-one production by enzymatic dehydration of 4-hydroxy-2-butanone. A significant production of 3-buten-2-one was observed for several 3-hydroxyacyl-CoA dehydratases.

Figure 5:
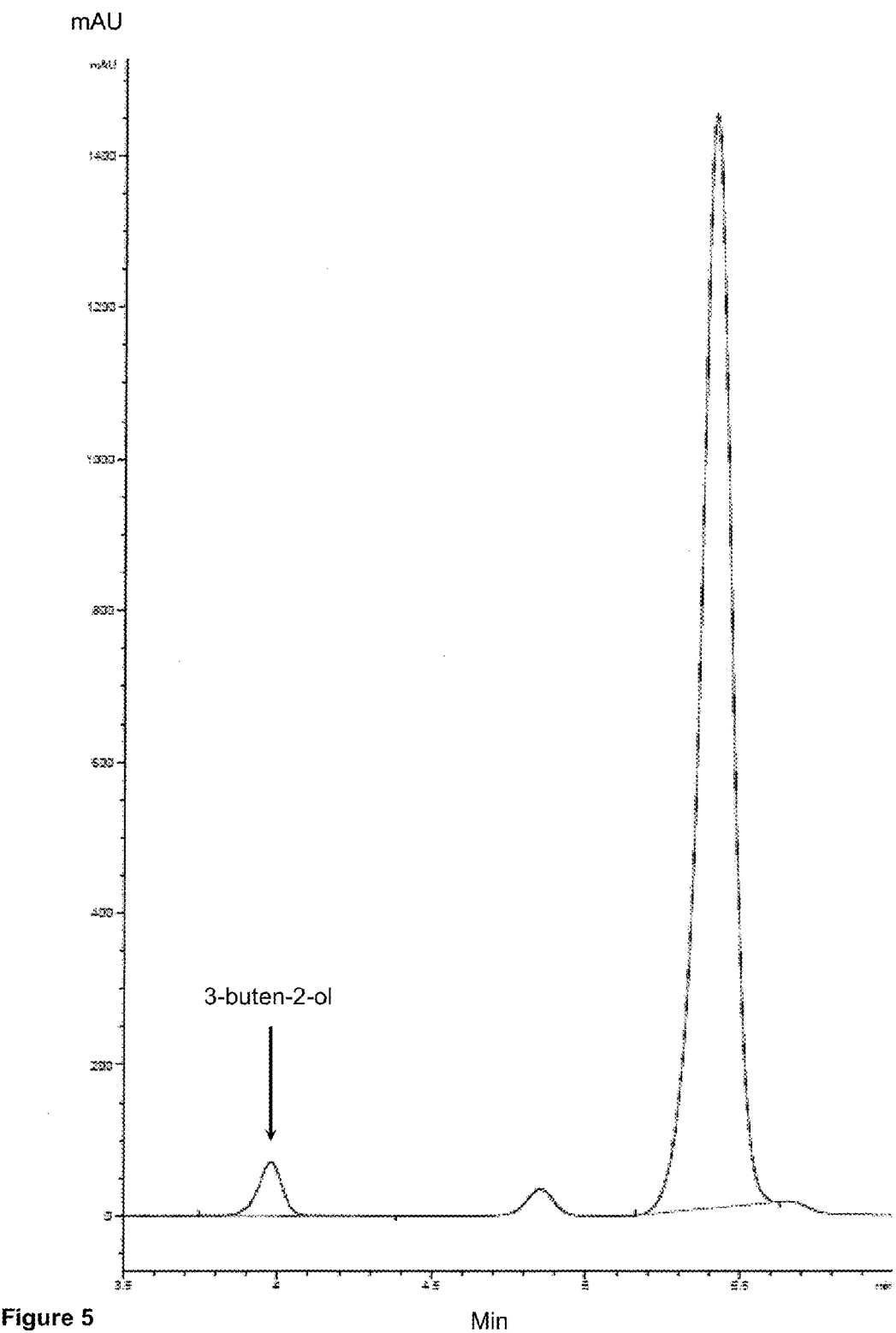

FIG. 5: shows a chromatogram obtained for the enzymatic reduction 3-buten-2-one to 3-buten-2-ol catalyzed by alcohol dehydrogenase from *Thermoanaerobium brockii* as outlined in Example 8. The assay was performed with 20 mM 3-buten-2-one and incubated for 4 hours.

Figure 6:
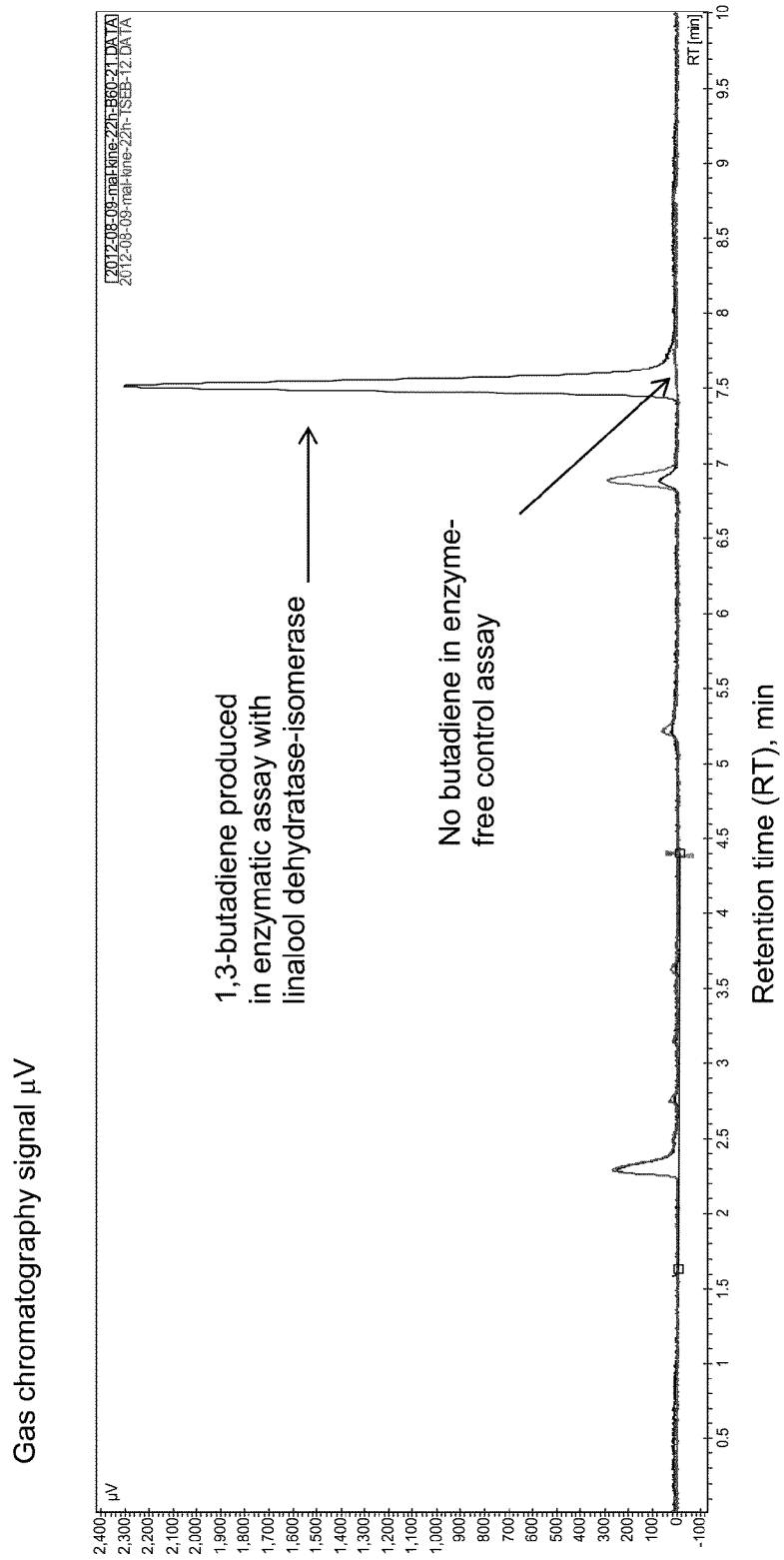

FIG. 6: shows GC/FID chromatograms obtained for enzymatic and enzyme-free assays with 80 mM 3-buten-2-ol and linalool dehydratase-isomerase after 22 hours incubation.

Other aspects and advantages of the invention will be described in the following examples, which are given for purposes of illustration and not by way of limitation.

EXAMPLES

Example 1: Cloning, Expression and Purification of Enzymes

Gene Synthesis, Cloning and Expression of Recombinant Proteins

The sequences of studied enzymes inferred from the genomes of prokaryotic and eukaryotic organisms were generated by oligonucleotide concatenation to fit the codon usage of *E. coli* (genes were commercially synthesized by GeneArt AG). A stretch of 6 histidine codons was inserted after the methionine initiation codon to provide an affinity tag for purification. The genes thus synthesized were cloned in a pET-25b(+) expression vector (vectors were constructed by GeneArt AG).

Competent *E. coli* BL21(DE3) cells (Novagen) were transformed with these vectors according to standard heat shock procedure. The transformed cells were grown with shaking (160 rpm) using ZYM-5052 auto-induction medium (Studier F W, Prot. Exp. Pur. 41, (2005), 207-234) for 6 h at 37° C. and protein expression was continued at 28° C. or 20° C. overnight (approximately 16 h). The cells were collected by centrifugation at 4° C., 10.000 rpm for 20 min and the pellets were stored at −80° C.

Protein Purification and Concentration

The pellets from 200 ml of culture cells were thawed on ice and resuspended in 5 ml of $Na_2HPO_4$ pH 8 containing 300 mM NaCl, 5 mM $MgCl_2$ and 1 mM DTT. Twenty microliters of lysonase (Novagen) were added. Cells were incubated 10 minutes at room temperature and then returned to ice for 20 minutes. Cell lysis was completed by sonication for 3×15 seconds. The bacterial extracts were then clarified by centrifugation at 4° C., 10.000 rpm for 20 min. The clarified bacterial lysates were loaded on PROTINO-1000 Ni-TED column (Macherey-Nagel) allowing adsorption of 6-His tagged proteins. Columns were washed and the enzymes of interest were eluted with 4 ml of 50 mM $Na_2HPO_4$ pH 8 containing 300 mM NaCl, 5 mM $MgCl_2$, 1 mM DTT, 250 mM imidazole. Eluates were then concentrated, desalted on Amicon Ultra-4 10 kDa filter unit (Millipore) and enzymes were resuspended in buffers compatible with downstream enzyme activity assay. Protein concentrations were quantified by direct UV 280 nm measurement on the NanoDrop 1000 spectrophotometer (Thermo Scientific). The purity of proteins thus purified varied from 60% to 90%.

Example 2: Continuous Spectrophotometric Assay of Acetoacetyl-CoA Reductase Activity The genes of short-chain dehydrogenase/fatty acyl-CoA reductases were synthesized and corresponding enzymes were further produced according to the procedure described in Example 1. Purified enzymes were resuspended in 50 mM potassium phosphate buffer pH 7.5.

Standard reaction mixture for assays of acetoacetyl-CoA reductase activity contained 5 mM acetoacetyl-CoA, 100 mM NaCl and 0.1-0.4 mM NADPH in 50 mM potassium phosphate buffer pH 7.5. Each assay was started by adding 1 mg/ml of enzyme. Control assays were performed in which either no enzyme was added, or no substrate was added. Reactions were conducted at 37° C. Each sample was continuously monitored for the decrease of NADPH at 340 nm on a SpectraMax Plus384 UV/Vis Microplate Reader (Molecular Device). Several enzymes demonstrated acetoacetyl-CoA reductase activity with NADPH as cofactor (Table 1).

TABLE 1

| Enzyme | Activity, nmol/min/mg protein |
|---|---|
| Short-chain dehydrogenase/reductase (Fatty alcohol forming acyl-CoA reductase) from *Marinobacter aquaeolei* VT8 | 2.3 |
| Short chain alcohol dehydrogenase-like protein from *Hahella chejuensis* | 0.9 |

TABLE 1-continued

| Enzyme | Activity, nmol/min/mg protein |
| --- | --- |
| Short chain alcohol dehydrogenase-like protein from Marinobacter manganoxydans | 1.7 |

The products of the enzymatic reduction of acetoacetyl-CoA were next analyzed by high-performance liquid chromatography (HPLC).

Example 3: HPLC-Based Analysis of Products of the Enzymatic Reduction of Acetoacetyl-CoA The enzymatic assays were carried out under the following conditions:
50 mM potassium phosphate pH 7.5
100 mM NaCl
60 mM NADPH
0-32 mM acetoacetyl-CoA The assays were initiated with the addition of 150 μg of purified dehydrogenase/reductase to 150 μl of reaction mixture. Incubations were run for 0, 0.5, 1, 2 and 4 hours with shaking at 37° C. The reactions were stopped by heating at 65° C. for 5 minutes, centrifuged and 120 μl of the clarified supernatants were transferred into a clean vial. Commercial 4-hydroxy-2-butanone (Sigma) was used as reference. HPLC analyses were performed using a 1260 Infinity LC System (Agilent), equipped with refractometer detector and column heating module. 10 μl of samples were separated on ZORBAK® SB-Aq column (250×4.6 mm, 5 μm particle size, column temp. 75° C.) with a mobile phase flow rate of 1.5 ml/min. The mobile phase consisted of aqueous sulfuric acid (8.4 mM). Retention time of 4-hydroxy-2-butanone under these conditions was 3.2 min.

The HPLC analysis showed that 4-hydroxy-2-butanone was formed by enzyme-catalyzed reduction of acetoacetyl-CoA. A typical chromatogram obtained with short chain alcohol dehydrogenase-like protein from *H. chejuensis* is shown on FIG. 2.

These data indicate that the short-chain dehydrogenase/reductase catalyzes the four-electron reduction of acetoacetyl-CoA to 4-hydroxy-2-butanone.

Example 4: Kinetic Parameters of Acetoacetyl-CoA Reduction

Enzyme assays were carried out in a total volume of 150 μl potassium phosphate (50 mM, pH 7.5), containing 100 mM NaCl and pure enzyme (150 μg). Kinetic parameters were determined with acetoacetyl-CoA as variable substrate (0-32 mM), and NADPH concentration was kept constant (60 mM). The amount of 4-hydroxy-2-butanone that forms for each assay was measured using HPLC-based procedure as described in Example 3.

Kinetic parameters obtained for purified short-chain dehydrogenase/fatty acyl-CoA reductases are presented in Table 2.

TABLE 2

| Enzyme | $K_m$, mM | $k_{cat}$, $s^{-1}$ |
| --- | --- | --- |
| Short-chain dehydrogenase/reductase (Fatty alcohol forming acyl-CoA reductase) from *Marinobacter aquaeolei* VT8 | 8 | 0.10 |
| Short chain alcohol dehydrogenase-like protein from Hahella chejuensis | 5 | 0.07 |

Example 5: Enzyme-Catalyzed Dehydration of 4-hydroxy-2-butanone to 3-buten-2-one Sequences of 3-hydroxypropionyl-CoA and 3-hydroxybutyryl-CoA dehydratases inferred from the genome of archaea and bacteria were generated according to the procedure described in Example 1. The genes thus synthesized were cloned in a pET25b(+) expression vector (vectors were constructed by GeneArt AG) and the proteins were produced according to the procedure described in Example 1.

The purified dehydratases were evaluated for their ability to dehydrate 4-hydroxy-2-butanone.

The studied enzymatic reaction was carried out under the following conditions at 37° C.:
50 mM Tris-HCl pH 7.5
20 mM $MgCl_2$
100 mM 4-hydroxy-2-butanone
Reaction volume was 0.4 ml Each assay was started with the addition of a specific enzyme at a final concentration of 4 mg/ml. Control assays were performed in which either no enzyme was added, or no substrate was added. Test tubes were incubated for 23 hours with shaking at 37° C. Reaction products were extracted with an equal volume of ethyl acetate and then analyzed by HPLC. Commercial 3-buten-2-one (Sigma) was used as reference. HPLC analysis were performed using a 1260 Infinity LC System (Agilent), equipped with column heating module and refractometer and UV detector. 10 μl of samples were separated on ZORBAX® SB-Aq column (250×4.6 mm, 5 μm particle size, column temp. 30° C.) with a mobile phase flow rate of 1.5 ml/min. The mobile phase consisted of 98:2 (v/v) $H_2O$/Acetonitrile containing 8.4 mM sulfuric acid. Retention time of 3-buten-2-one under these conditions was 5.4 min.

Example of typical chromatogram obtained for 3-hydroxypropionyl-CoA dehydratase from *S. tokodaii* is presented in FIG. 3. Significant production of 3-buten-2-one was observed in enzymatic assay with several 3-hydroxyacyl-CoA dehydratases (FIG. 4).

Example 6: Kinetic Parameters of the Dehydration of 4-hydroxy-2-butanone to 3-buten-2-one Kinetic parameters of the reaction were determined for purified recombinant 3-hydroxypropionyl-CoA dehydratase from *Sulfolobus tokodaii* under the following conditions:
100 mM Tris-HCl pH 7.5
20 mM $MgCl_2$
0-300 mM 4-Hydroxy-2-butanone
4 mg/ml 3-Hydroxypropionyl-CoA dehydratase *S. tokodaii*

Test tubes were incubated for 0, 20, 60, 120 and 180 min with shaking at 37° C. The formation of 3-buten-2-one was quantified using commercial 3-buten-2-one according to the procedure described in Example 4.

Hydroxypropionyl-CoA dehydratase from *S. tokodaii* was found to have a $K_M$ higher than 0.4 M and a $k_{cat}$ of $7.5 \times 10^{-3}$ $s^{-1}$.

Example 7: Screening of a Collection of Reductases Using 3-buten-2-one as Substrate and NADPH as Cofactor A set of 10 genes encoding representatives of the reductase/alcohol dehydrogenase across eukaryotic and prokaryotic organisms was constructed and tested to identify the potential candidates for 3-buten-2-ol production from 3-buten-2-one. The genes were synthesized and corresponding enzymes were then produced according to the procedure described in Example 1.

For the reductase assay, a reaction mixture containing 50 mM Tris-HCl pH 7.5, 0.4 mM NADPH, 50 mM NaCl, 20 mM 3-buten-2-one and 0.001-1 mg/ml enzyme in a total volume of 120 µl was used and the reaction was carried out at 37° C. for 20 min. Assays with alcohol dehydrogenase from *Thermoanaerobium brockii* and short chain alcohol dehydrogenase-like protein from *Hahella chejuensis* were conducted in 50 mM potassium phosphate buffer pH 7.5 instead of Tris-HCl buffer. Enzyme, substrate and cofactor negative control reactions were performed in parallel. Each sample was continuously monitored for the decrease of NADPH at 340 nm on a SpectraMax Plus384 UV/Vis Microplate Reader (Molecular Device). Several enzymes demonstrated reductase activity with 3-buten-2-one as substrate and NADPH as cofactor (Table 3).

TABLE 3

| Enzyme | Activity, µmol/min/mg protein |
|---|---|
| Secondary alcohol dehydrogenase *Rhodococcus ruber* (Uniprot Q8KLT9) | 0.069 |
| Alcohol dehydrogenase *Thermoanaerobacter brockii* (*Thermoanaerobium brockii*) (Uniprot P14941) | 0.098 |
| R-specific alcohol dehydrogenase *Lactobacillus kefiri* (Uniprot Q6WVP7) | 26.0 |
| R-specific alcohol dehydrogenase *Lactobacillus brevis* (Uniprot Q84EX5) | 29.0 |
| S-specific alcohol dehydrogenase *Lactobacillus kefiri* (Uniprot B5AXN9) | 0.03 |
| S-specific alcohol dehydrogenase *Lactobacillus brevis* (Uniprot C2D0H5) | 0.03 |
| Carbonyl reductase from *Rattus norvegicus* (Uniprot B2GV72) | 2.6 |
| Short chain alcohol dehydrogenase-like protein from *Hahella chejuensis* (Uniprot Q2SCE0) | 0.003 |

Example 8: HPLC-Based Analysis of the Enzyme-Catalyzed Reduction of 3-buten-2-one by Alcohol Dehydrogenase from *Thermoanaerobium brockii*

The studied enzymatic reaction was carried out under the following conditions at 37° C.:
50 mM Tris-HCl pH 7.5
50 mM NaCl
1 mM DTT
40 mM NADPH
0.1 mM $ZnCl_2$
0-40 mM 3-buten-2-one
1 mg/ml alcohol dehydrogenase from *Th. brockii*
Reaction volume was 200 µl.
The assays were incubated for various time periods (0, 20, 40, 60 120 and 240 min) with shaking at 37° C. The reactions were stopped by heating at 65° C. for 5 minutes, reaction mixtures were centrifuged and 150 µl of the clarified supernatant were transferred into a clean vial. The reaction products were then extracted with an equal volume of ethyl acetate. 150 µl of the upper ethyl acetate phase was transferred into a clean vial for HPLC analysis. Commercial 3-buten-2-ol (Sigma) was used as reference. HPLC analysis was performed using a 1260 Inifinity LC System (Agilent), equipped with column heating module and refractometer and UV detector. 10 µl of samples were separated on ZORBAK® SB-Aq column (250×4.6 mm, 5 µm particle size, column temp. 30° C.) with a mobile phase flow rate of 1.5 ml/min. The mobile phase consisted of 98:2 (v/v) $H_2O$/acetonitrile containing 8.4 mM sulfuric acid. Retention time of 3-buten-2-ol and 3-buten-2-one under these conditions was 3.9 and 5.4 min, respectively.

Significant and reproducible production of 3-buten-2-ol was observed in enzymatic assay. An example of a typical chromatogram is presented in FIG. 5. These data indicate that the reduction of 3-buten-2-one can be achieved using alcohol dehydrogenase in the presence of NADPH as cofactor, leading to the production of 3-buten-2-ol.

Secondary alcohol dehydrogenase from *Th. brockii* was found to have a $K_M$ of 100 mM and a $k_{cat}$ of at least 0.5 $s^{-1}$.

Example 9: Kinetic Parameters of the Reduction of 3-buten-2-one to 3-buten-2-ol by R-Specific Alcohol Dehydrogenase from *Lactobacillus kefiri*

The studied enzymatic reaction was carried out under the following conditions at 37° C.:
50 mM Tris-HCl pH 7.5
50 mM NaCl
1 mM DTT
40 mM NADPH
0-40 mM 3-buten-2-one
1 mg/ml alcohol dehydrogenase from *L. kefiri*.
Reaction volume was 200 µl.
The assays were incubated for 0, 10, 20, 40, 60 and 120 min with shaking at 37° C. The formation of 3-buten-2-ol was quantified according to the protocol described in Example 8. R-specific alcohol dehydrogenase from *Lactobacillus kefiri* was found to have a $K_M$ of 19 mM and a $k_{cat}$ of 4 $s^{-1}$.

Example 10: Kinetic Parameters of the Reduction of 3-buten-2-one to 3-buten-2-ol by Secondary Alcohol Dehydrogenase from *Rhodococcus ruber*

The studied enzymatic reaction was carried out under the following conditions at 37° C.:
50 mM Tris-HCl pH 7.5
50 mM NaCl
1 mM DTT
40 mM NADPH
0-40 mM 3-buten-2-one
1 mg/ml alcohol dehydrogenase from *R. ruber*.
Reaction volume was 200 µl.
The assays were incubated for 0, 10, 20, 40, 60 and 120 min with shaking at 37° C. The formation of 3-buten-2-ol was quantified according to the protocol described in Example 8. Secondary alcohol dehydrogenase from *Rhodococcus ruber* was found to have a $K_M$ of 180 mM and a $k_{cat}$ of at least 0.03 $s^{-1}$.

Example 11: Cloning and Expression in *E. coli* of the Gene for Linalool Dehydratase-Isomerase Cloning and Bacterial Culture
The sequence of linalool dehydratase-isomerase inferred from the genome of *Castellaniella defragrans* (formerly *Alcaligenes defragrans*) was generated by oligonucleotide concatenation to fit the codon usage of *E. coli*. A stretch of 6 histidine codons was inserted after the methionine initiation codon to provide an affinity tag for purification. The gene thus synthesized was cloned in a pET25b(+) expression vector (the vector was constructed by GeneArt AG). Competent *E. coli* BL21(DE3) cells (Novagen) were transformed with this vector according to the heat shock procedure. As negative control, *E. coli* BL21(DE3) strain was transformed with empty vector. The transformed cells were grown with shaking (160 rpm) on ZYM-5052 auto-induction medium (Studier F W, *Prot. Exp. Pur.* 41 (2005), 207-234) for 6 hours at 37° C. and protein expression was continued at 18° C. overnight (approximately 12 hours). The cells were collected by centrifugation at 4° C., 10,000 rpm for 20 min and the pellets were frozen at −80° C.

Preparation of Cell Lysate

The pellets from 100 ml of culture cells were thawed on ice and resuspended in 4 ml of 50 mM Tris-HCl pH 7.5. 10 µl of lysonase (Novagen) were then added. Cells were incubated for 10 minutes at room temperature and then returned to ice for 20 minutes. Protein concentration was determined using the Bradford method (Biorad).

Example 12: 1,3-butadiene Production from 3-buten-2-ol

The enzymatic assays were carried out under the following conditions:
50 mM Tris HCl pH 7.5
2 mM D,L-Dithiothreitol
0-80 mM 3-buten-2-ol
The pH was adjusted to 7.5

0.25 ml of cell lysate containing recombinant linalool dehydratase-isomerase was added to 0.5 ml of reaction mixture. An enzyme-free control reaction containing lysate of *E. coli* cells transformed with empty vector was carried out in parallel. Assays were incubated at 37° C. for 1-22 hours in a 2 ml sealed glass vial (Interchim) with shaking. 1,3-butadiene production was analyzed by GC/FID procedure. For this purpose one ml of the headspace phase was then collected and injected into a gas chromatograph Varian 450-GC equipped with a flame ionization detector (FID). Nitrogen was used as carrier gas with a flow rate of 1.5 ml/min. Volatile compounds were chromatographically separated on Rt-Alumina Bond/$Na_2SO_4$ column (Restek) using an isothermal mode at 130° C. The enzymatic reaction product was identified by comparison with 1,3-butadiene standard (Sigma). Under these GC conditions, the retention time for butadiene was 7.6 min. A significant production of 1,3-butadiene was observed in enzymatic assay with linalool dehydratase-isomerase. No butadiene signal was observed in enzyme-free control assay (FIG. 6). The turnover number for this conversion amounted to about $10^{-4}$ $s^{-1}$ substrate molecule per enzyme active site.

The invention claimed is:

1. A method for the production of 3-buten-2-one comprising the enzymatic conversion of 4-hydroxy-2-butanone into 3-buten-2-one by an enzyme catalyzing 4-hydroxy-2-butanone dehydration, wherein said enzyme is:
   (a) a 3-hydroxypropionyl-CoA dehydratase (EC 4.2.1.116),
   (b) a 3-hydroxybutyryl-CoA dehydratase (EC 4.2.1.55),
   (c) an enoyl-CoA hydratase (EC 4.2.1.17),
   (d) a long-chain-enoyl-CoA hydratase (EC 4.2.1.74) and
   (e) a 3-methylglutaconyl-CoA hydratase (EC 4.2.1.18).

2. The method of claim 1, wherein the enzyme is
   (a) a 3-hydroxypropionyl-CoA dehydratase of *M. cuprina* (SEQ ID NO:1),
   (b) a 3-hydroxypropionyl-CoA dehydratase of *S. tokodaii* (SEQ ID NO:3),
   (c) a 3-hydroxypropionyl-CoA dehydratase of *M. sedula* (SEQ ID NO:2),
   (d) a 3-hydroxybutyryl-CoA dehydratase of *S. acidocaldarius* (SEQ ID NO:5),
   (e) a 3-hydroxybutyryl-CoA dehydratase of *A. hospitalis* (SEQ ID NO:6), or
   (f) a 3-hydroxypropionyl-CoA dehydratase of *B. laterosporus* (SEQ ID NO:4).

3. The method of claim 1, further comprising the enzymatic conversion of acetoacetyl-CoA into said 4-hydroxy-2-butanone by an acetoacetyl-CoA reductase.

4. The method of claim 3 wherein said acetoacetyl-CoA reductase is
   (i) a hydroxymethylglutaryl-CoA reductase (EC 1.1.1.34); or
   (ii) a short chain dehydrogenase/fatty acyl-CoA reductase.

5. The method of claim 3, further comprising the enzymatic conversion of acetyl-CoA into acetoacetyl-CoA.

6. The method of claim 1, further comprising the enzymatic conversion of 3-buten-2-one into 3-buten-2-ol by a 3-buten-2-one reductase.

7. The method of claim 6, wherein said 3-buten-2-one reductase is
   (i) a carbonyl reductase (EC 1.1.1.184),
   (ii) an alcohol dehydrogenase, or
   (iii) a short chain dehydrogenase/fatty acyl-CoA reductase.

8. The method of claim 6 further comprising enzymatically converting 3-buten-2-ol into 1,3-butadiene by an alkenol dehydratase.

9. The method of claim 1, wherein 3-buten-2-one is recovered.

10. The method of claim 6, wherein 3-buten-2-ol is recovered.

11. The method of claim 8, wherein 1,3-butadiene is recovered.

* * * * *

SEQUENCE LISTING

```
<160> NUMBER OF SEQ ID NOS: 25

<210> SEQ ID NO 1
<211> LENGTH: 259
<212> TYPE: PRT
<213> ORGANISM: Metallosphaera cuprina Ar-4
<220> FEATURE:
<223> OTHER INFORMATION: 3-Hydroxypropionyl-CoA dehydratase

<400> SEQUENCE: 1

Met Glu Tyr Glu Thr Leu Glu Thr Lys Lys Glu Gly Asn Leu Phe Trp
1               5                   10                  15

Ile Thr Leu Asn Arg Pro Asp Lys Leu Asn Ala Leu Asn Ser Lys Leu
            20                  25                  30

Leu Glu Glu Leu Asn Arg Ala Val Ser Glu Gly Glu Ser Asp Pro Glu
        35                  40                  45

Val Arg Val Ile Ile Ile Thr Gly Lys Gly Lys Ala Phe Cys Ala Gly
    50                  55                  60

Ala Asp Ile Thr Gln Phe Asn Gln Leu Ser Pro Thr Asp Ala Trp Arg
65                  70                  75                  80

Phe Ser Lys Arg Gly Arg Glu Val Met Asp Lys Ile Glu Ser Leu Ser
                85                  90                  95

Lys Pro Thr Ile Ala Met Ile Asn Gly Tyr Ala Leu Gly Gly Gly Leu
            100                 105                 110

Glu Leu Ala Leu Ser Cys Asp Ile Arg Ile Ala Ala Glu Glu Ala Gln
        115                 120                 125

Leu Gly Leu Pro Glu Ile Asn Leu Gly Ile Tyr Pro Gly Tyr Gly Gly
    130                 135                 140

Thr Gln Arg Leu Thr Arg Ile Val Gly Lys Gly Arg Ala Leu Glu Ile
145                 150                 155                 160

Met Met Thr Gly Asp Arg Leu Ser Gly Lys Asp Ala Glu Arg Tyr Gly
                165                 170                 175

Leu Val Asn Arg Val Thr Pro Leu Ser Asn Leu Glu Gln Glu Thr Arg
            180                 185                 190
```

```
Lys Leu Ala Glu Lys Ile Ala Arg Lys Ser Pro Val Ser Leu Ala Leu
            195                 200                 205

Ile Lys Glu Val Val Asn Lys Gly Leu Asp Ser Pro Leu Ala Ser Gly
        210                 215                 220

Leu Ser Leu Glu Ser Ile Gly Trp Gly Val Ile Phe Ser Thr Glu Asp
225                 230                 235                 240

Lys Lys Glu Gly Val Asn Ala Phe Leu Glu Lys Arg Glu Pro Asn Phe
                245                 250                 255

Lys Gly Lys

<210> SEQ ID NO 2
<211> LENGTH: 259
<212> TYPE: PRT
<213> ORGANISM: Metallosphaera sedula
<220> FEATURE:
<223> OTHER INFORMATION: 3-hydroxypropionyl-coenzyme A dehydratase

<400> SEQUENCE: 2

Met Glu Phe Glu Thr Ile Glu Thr Lys Lys Glu Gly Asn Leu Phe Trp
1               5                   10                  15

Ile Thr Leu Asn Arg Pro Asp Lys Leu Asn Ala Leu Asn Ala Lys Leu
            20                  25                  30

Leu Glu Glu Leu Asp Arg Ala Val Ser Gln Ala Glu Ser Asp Pro Glu
        35                  40                  45

Ile Arg Val Ile Ile Ile Thr Gly Lys Gly Lys Ala Phe Cys Ala Gly
    50                  55                  60

Ala Asp Ile Thr Gln Phe Asn Gln Leu Thr Pro Ala Glu Ala Trp Lys
65                  70                  75                  80

Phe Ser Lys Lys Gly Arg Glu Ile Met Asp Lys Ile Glu Ala Leu Ser
                85                  90                  95

Lys Pro Thr Ile Ala Met Ile Asn Gly Tyr Ala Leu Gly Gly Gly Leu
            100                 105                 110

Glu Leu Ala Leu Ala Cys Asp Ile Arg Ile Ala Ala Glu Glu Ala Gln
        115                 120                 125

Leu Gly Leu Pro Glu Ile Asn Leu Gly Ile Tyr Pro Gly Tyr Gly Gly
    130                 135                 140

Thr Gln Arg Leu Thr Arg Val Ile Gly Lys Gly Arg Ala Leu Glu Met
145                 150                 155                 160

Met Met Thr Gly Asp Arg Ile Pro Gly Lys Asp Ala Glu Lys Tyr Gly
                165                 170                 175

Leu Val Asn Arg Val Val Pro Leu Ala Asn Leu Glu Gln Glu Thr Arg
            180                 185                 190

Lys Leu Ala Glu Lys Ile Ala Lys Lys Ser Pro Ile Ser Leu Ala Leu
            195                 200                 205

Ile Lys Glu Val Val Asn Arg Gly Leu Asp Ser Pro Leu Leu Ser Gly
        210                 215                 220

Leu Ala Leu Glu Ser Val Gly Trp Gly Val Val Phe Ser Thr Glu Asp
225                 230                 235                 240

Lys Lys Glu Gly Val Ser Ala Phe Leu Glu Lys Arg Glu Pro Thr Phe
                245                 250                 255

Lys Gly Lys

<210> SEQ ID NO 3
<211> LENGTH: 257
<212> TYPE: PRT
<213> ORGANISM: Sulfolobus tokodaii str. 7
```

-continued

```
<220> FEATURE:
<223> OTHER INFORMATION: 3-hydroxypropionyl-CoA dehydratase

<400> SEQUENCE: 3

Met Glu Thr Ile Val Ile Lys Lys Glu Thr Pro Ile Gly Trp Ile Tyr
1               5                   10                  15

Leu Asn Arg Pro Asp Arg Leu Asn Ala Ile Asn Gln Gln Met Ile Lys
            20                  25                  30

Glu Leu Arg Gln Gly Ile Asp Glu Met Val Tyr Asp Ser Asp Ile Lys
        35                  40                  45

Val Ile Ile Ile Thr Gly Asn Gly Lys Ala Phe Ser Ala Gly Ala Asp
    50                  55                  60

Ile Ser Arg Phe Lys Glu Leu Asn Gly Tyr Thr Ala Trp Gln Phe Ala
65                  70                  75                  80

Lys Ser Gly Arg Glu Leu Met Asp Tyr Ile Glu Asn Ile Ser Lys Pro
                85                  90                  95

Thr Ile Ala Met Val Asn Gly Tyr Ala Leu Gly Gly Gly Leu Glu Leu
            100                 105                 110

Ala Met Ala Cys Asp Ile Arg Ile Ala Ala Glu Glu Ala Gln Leu Gly
        115                 120                 125

Leu Pro Glu Ile Asn Leu Gly Ile Tyr Pro Gly Phe Gly Gly Thr Gln
    130                 135                 140

Arg Leu Val Arg Leu Ile Gly Lys Gly Lys Ala Leu Glu Leu Met Leu
145                 150                 155                 160

Thr Gly Asp Arg Ile Ser Ala Lys Glu Ala Glu Lys Ile Gly Leu Val
                165                 170                 175

Asn Lys Val Val Pro Leu Ser Asn Leu Glu Gln Glu Thr Arg Asn Phe
            180                 185                 190

Ala Leu Lys Leu Ala Glu Lys Pro Pro Ile Ser Ile Ala Leu Ile Lys
        195                 200                 205

Leu Leu Val Asn Gln Gly Ile Asp Leu Pro Ile Leu Ala Gly Leu Asn
    210                 215                 220

Met Glu Ser Leu Gly Trp Gly Val Val Phe Ser Thr Glu Asp Glu Lys
225                 230                 235                 240

Glu Gly Val Ser Ala Phe Leu Glu Lys Arg Lys Ala Gln Phe Lys Gly
                245                 250                 255

Lys

<210> SEQ ID NO 4
<211> LENGTH: 258
<212> TYPE: PRT
<213> ORGANISM: Brevibacillus laterosporus LMG 15441
<220> FEATURE:
<223> OTHER INFORMATION: 3-hydroxypropionyl-coenzyme A dehydratase

<400> SEQUENCE: 4

Met Ser Tyr Pro Asn Leu Thr Leu Val Thr Glu Gly Thr Ile Ala Ile
1               5                   10                  15

Val Thr Ile Asn His Pro Pro Ala Asn Ala Leu Asn Gln Ala Thr Leu
            20                  25                  30

Thr Ser Leu Ala Gln Ala Leu Asp Asp Leu Glu Gln Asn Asp Gln Ile
        35                  40                  45

Arg Ala Ile Val Ile Thr Gly Glu Gly Arg Phe Phe Ile Ala Gly Ala
    50                  55                  60

Asp Ile Lys Glu Phe Thr Ala Leu Ala Glu Gln Ser Pro Gln Gln Val
65                  70                  75                  80
```

Ala Glu Arg Gly Gln Gln Leu Phe Leu Arg Met Glu Thr Phe Ser Lys
                85                  90                  95

Pro Ile Ile Ala Ala Ile Asn Gly Ala Cys Leu Gly Gly Gly Leu Glu
            100                 105                 110

Leu Ala Met Ala Cys His Ile Arg Tyr Val Ala Lys Glu Ala Lys Leu
        115                 120                 125

Gly Leu Pro Glu Leu Asn Leu Gly Leu Ile Pro Gly Tyr Gly Gly Thr
    130                 135                 140

Gln Arg Leu Pro Arg Leu Ile Gly Arg Gly Lys Ala Thr Gln Leu Ile
145                 150                 155                 160

Leu Thr Ser Asp Met Ile Asp Gly Glu Glu Ala Leu Ala Ile Gly Leu
                165                 170                 175

Ala Glu Ala Val Tyr Pro Val Glu Gln Leu Leu Glu Glu Ser Lys Lys
            180                 185                 190

Leu Ala Arg Lys Ile Ser Glu Lys Gly Ala Ile Ser Val Lys Tyr Ala
        195                 200                 205

Leu Asp Ala Ile His Ser Gly Val Glu Leu Gly Leu Ser Ala Gly Met
    210                 215                 220

Lys Arg Glu Ala Glu Leu Phe Gly Gln Val Phe Thr Thr Glu Asp Met
225                 230                 235                 240

Lys Glu Gly Val Thr Ala Phe Leu Glu Lys Arg Lys Pro Gln Phe Ser
                245                 250                 255

Asn Arg

<210> SEQ ID NO 5
<211> LENGTH: 257
<212> TYPE: PRT
<213> ORGANISM: Sulfolobus acidocaldarius DSM 639
<220> FEATURE:
<223> OTHER INFORMATION: 3-hydroxybutyryl-CoA dehydratase

<400> SEQUENCE: 5

Met Glu Thr Ile Ile Val Lys Asn Glu Pro Pro Phe Leu Arg Ile Thr
1               5                   10                  15

Leu Asn Arg Pro Asp Arg Leu Asn Ala Ile Asn Lys Lys Met Ile Glu
            20                  25                  30

Glu Ile Arg Thr Val Leu Glu Glu Thr Val Lys Asp Glu Lys Val Arg
        35                  40                  45

Val Ile Ile Phe Thr Gly Asn Gly Arg Ala Phe Ser Ala Gly Ala Asp
    50                  55                  60

Ile Ser Gln Phe Lys Glu Leu Glu Gly Leu Thr Ala Trp Gln Phe Ala
65                  70                  75                  80

Met Lys Gly Arg Glu Leu Met Asp Tyr Ile Glu Asn Tyr Pro Lys Pro
                85                  90                  95

Thr Ile Ala Met Ile Asn Gly Tyr Ala Leu Gly Gly Gly Leu Glu Leu
            100                 105                 110

Ala Leu Ala Cys Asp Ile Arg Ile Ala Ser Asp Glu Ala Gln Leu Gly
        115                 120                 125

Leu Pro Glu Ile Thr Leu Gly Ile Tyr Pro Gly Phe Gly Gly Thr Gln
    130                 135                 140

Arg Leu Leu Lys Leu Val Gly Lys Ser Arg Thr Leu Glu Met Ile Met
145                 150                 155                 160

Leu Gly Glu Arg Ile Ser Ala Lys Asp Ala Glu Arg Ile Gly Leu Val
                165                 170                 175

```
Asn Arg Val Val Pro Ser Asn Asp Leu Glu Lys Glu Thr Leu Asn Leu
            180                 185                 190
Ala Ser Lys Leu Ala Glu Arg Pro Leu Ala Ile Gln Leu Ser Lys
        195                 200                 205
Leu Ile Val Asn Gln Gly Met Asn Ser Pro Ile Thr Val Gly Leu Asn
            210                 215                 220
Met Glu Ser Leu Gly Trp Gly Val Ile Phe Thr Thr Lys Asp Ser Lys
225                 230                 235                 240
Glu Gly Val Asn Ala Phe Leu Glu Lys Arg Lys Pro Asn Phe Lys Gly
            245                 250                 255
Glu

<210> SEQ ID NO 6
<211> LENGTH: 257
<212> TYPE: PRT
<213> ORGANISM: Acidianus hospitalis W1
<220> FEATURE:
<223> OTHER INFORMATION: 3-hydroxybutyryl-CoA dehydratase

<400> SEQUENCE: 6

Met Glu Thr Val Glu Thr Lys Ile Glu Asn Gly Ile Gly Trp Ile Ile
1               5                   10                  15
Leu Asn Arg Pro Asp Lys Leu Asn Ala Ile Asn Leu Lys Met Leu Glu
            20                  25                  30
Glu Leu Glu Glu Val Thr Lys Asn Phe Glu Glu Asn Asn Asp Val Lys
        35                  40                  45
Ile Ile Ile Phe Thr Gly Asn Gly Lys Ala Phe Ser Ala Gly Ala Asp
    50                  55                  60
Ile Ser Gln Phe Lys Glu Leu Asn Ser Ile Ser Ala Trp Asn Phe Ala
65                  70                  75                  80
Lys Lys Gly Arg Arg Val Met Asp Tyr Ile Glu Ser Val Ser Lys Pro
                85                  90                  95
Thr Ile Ala Met Ile Asn Gly Tyr Ala Leu Gly Gly Gly Leu Glu Leu
            100                 105                 110
Ala Leu Ala Cys Asp Phe Arg Ile Ala Ala Glu Ala Ser Leu Gly
        115                 120                 125
Leu Pro Glu Ile Asn Leu Gly Ile Tyr Pro Gly Phe Gly Gly Thr Gln
    130                 135                 140
Arg Leu Val Arg Ala Ile Gly Lys Ala Lys Ala Met Glu Leu Met Met
145                 150                 155                 160
Thr Gly Asp Arg Ile Ser Ala Lys Glu Ala Glu Arg Ile Gly Leu Val
                165                 170                 175
Asn Lys Val Val Ser Leu Ser Ser Leu Lys Glu Glu Thr Ile Lys Phe
            180                 185                 190
Ala Gly Lys Leu Met Glu Lys Ser Pro Ile Ala Leu Ala Ile Leu Lys
        195                 200                 205
His Ile Ile Leu Tyr Gly Asn Asp Ser Pro Leu Leu Asp Gly Leu Asn
    210                 215                 220
Met Glu Ser Leu Gly Trp Gly Val Ala Phe Ser Thr Glu Asp Glu Lys
225                 230                 235                 240
Glu Gly Val Ser Ala Phe Leu Glu Lys Arg Lys Ala Val Phe Lys Gly
                245                 250                 255
Lys
```

<210> SEQ ID NO 7
<211> LENGTH: 661
<212> TYPE: PRT
<213> ORGANISM: Marinobacter aquaeolei VT8
<220> FEATURE:
<223> OTHER INFORMATION: Short chain dehydrogenase

<400> SEQUENCE: 7

Met Asn Tyr Phe Leu Thr Gly Gly Thr Gly Phe Ile Gly Arg Phe Leu
1               5                   10                  15

Val Glu Lys Leu Leu Ala Arg Gly Gly Thr Val Tyr Val Leu Val Arg
            20                  25                  30

Glu Gln Ser Gln Asp Lys Leu Glu Arg Leu Arg Glu Arg Trp Gly Ala
        35                  40                  45

Asp Asp Lys Gln Val Lys Ala Val Ile Gly Asp Leu Thr Ser Lys Asn
    50                  55                  60

Leu Gly Ile Asp Ala Lys Thr Leu Lys Ser Leu Lys Gly Asn Ile Asp
65                  70                  75                  80

His Val Phe His Leu Ala Ala Val Tyr Asp Met Gly Ala Asp Glu Glu
                85                  90                  95

Ala Gln Ala Ala Thr Asn Ile Glu Gly Thr Arg Ala Ala Val Gln Ala
            100                 105                 110

Ala Glu Ala Met Gly Ala Lys His Phe His His Val Ser Ser Ile Ala
        115                 120                 125

Ala Ala Gly Leu Phe Lys Gly Ile Phe Arg Glu Asp Met Phe Glu Glu
    130                 135                 140

Ala Glu Lys Leu Asp His Pro Tyr Leu Arg Thr Lys His Glu Ser Glu
145                 150                 155                 160

Lys Val Val Arg Glu Glu Cys Lys Val Pro Phe Arg Ile Tyr Arg Pro
                165                 170                 175

Gly Met Val Ile Gly His Ser Glu Thr Gly Glu Met Asp Lys Val Asp
            180                 185                 190

Gly Pro Tyr Tyr Phe Phe Lys Met Ile Gln Lys Ile Arg His Ala Leu
        195                 200                 205

Pro Gln Trp Val Pro Thr Ile Gly Ile Glu Gly Gly Arg Leu Asn Ile
    210                 215                 220

Val Pro Val Asp Phe Val Val Asp Ala Leu Asp His Ile Ala His Leu
225                 230                 235                 240

Glu Gly Glu Asp Gly Asn Cys Phe His Leu Val Asp Ser Asp Pro Tyr
                245                 250                 255

Lys Val Gly Glu Ile Leu Asn Ile Phe Cys Glu Ala Gly His Ala Pro
            260                 265                 270

Arg Met Gly Met Arg Ile Asp Ser Arg Met Phe Gly Phe Ile Pro Pro
        275                 280                 285

Phe Ile Arg Gln Ser Ile Lys Asn Leu Pro Pro Val Lys Arg Ile Thr
    290                 295                 300

Gly Ala Leu Leu Asp Asp Met Gly Ile Pro Pro Ser Val Met Ser Phe
305                 310                 315                 320

Ile Asn Tyr Pro Thr Arg Phe Asp Thr Arg Glu Leu Glu Arg Val Leu
                325                 330                 335

Lys Gly Thr Asp Ile Glu Val Pro Arg Leu Pro Ser Tyr Ala Pro Val
            340                 345                 350

Ile Trp Asp Tyr Trp Glu Arg Asn Leu Asp Pro Asp Leu Phe Lys Asp
        355                 360                 365

Arg Thr Leu Lys Gly Thr Val Glu Gly Lys Val Cys Val Val Thr Gly

```
            370                 375                 380
Ala Thr Ser Gly Ile Gly Leu Ala Thr Ala Glu Lys Leu Ala Glu Ala
385                 390                 395                 400

Gly Ala Ile Leu Val Ile Gly Ala Arg Thr Lys Glu Thr Leu Asp Glu
                405                 410                 415

Val Ala Ala Ser Leu Glu Ala Lys Gly Gly Asn Val His Ala Tyr Gln
                420                 425                 430

Cys Asp Phe Ser Asp Met Asp Asp Cys Asp Arg Phe Val Lys Thr Val
            435                 440                 445

Leu Asp Asn His Gly His Val Asp Val Leu Val Asn Asn Ala Gly Arg
        450                 455                 460

Ser Ile Arg Arg Ser Leu Ala Leu Ser Phe Asp Arg Phe His Asp Phe
465                 470                 475                 480

Glu Arg Thr Met Gln Leu Asn Tyr Phe Gly Ser Val Arg Leu Ile Met
                485                 490                 495

Gly Phe Ala Pro Ala Met Leu Glu Arg Arg Gly His Val Val Asn
            500                 505                 510

Ile Ser Ser Ile Gly Val Leu Thr Asn Ala Pro Arg Phe Ser Ala Tyr
        515                 520                 525

Val Ser Ser Lys Ser Ala Leu Asp Ala Phe Ser Arg Cys Ala Ala Ala
530                 535                 540

Glu Trp Ser Asp Arg Asn Val Thr Phe Thr Thr Ile Asn Met Pro Leu
545                 550                 555                 560

Val Lys Thr Pro Met Ile Ala Pro Thr Lys Ile Tyr Asp Ser Val Pro
                565                 570                 575

Thr Leu Thr Pro Asp Glu Ala Ala Gln Met Val Ala Asp Ala Ile Val
            580                 585                 590

Tyr Arg Pro Lys Arg Ile Ala Thr Arg Leu Gly Val Phe Ala Gln Val
        595                 600                 605

Leu His Ala Leu Ala Pro Lys Met Gly Glu Ile Ile Met Asn Thr Gly
    610                 615                 620

Tyr Arg Met Phe Pro Asp Ser Pro Ala Ala Gly Ser Lys Ser Gly
625                 630                 635                 640

Glu Lys Pro Lys Val Ser Thr Glu Gln Val Ala Phe Ala Ala Ile Met
                645                 650                 655

Arg Gly Ile Tyr Trp
            660

<210> SEQ ID NO 8
<211> LENGTH: 661
<212> TYPE: PRT
<213> ORGANISM: Marinobacter manganoxydans
<220> FEATURE:
<223> OTHER INFORMATION: Short chain dehydrogenase

<400> SEQUENCE: 8

Met Asn Tyr Phe Leu Thr Gly Gly Thr Gly Phe Ile Gly Arg Phe Leu
1               5                   10                  15

Val Glu Lys Leu Leu Ala Arg Gly Gly Thr Val His Val Leu Val Arg
                20                  25                  30

Glu Gln Ser Gln Asp Lys Leu Asp Lys Leu Arg Glu Arg Trp Gly Ala
            35                  40                  45

Asp Glu Thr Gln Val Lys Ala Val Ile Gly Asp Leu Thr Ser Lys Asn
        50                  55                  60

Leu Gly Ile Asp Ala Lys Thr Met Lys Ala Leu Lys Gly Lys Ile Asp
```

```
            65                  70                  75                  80
His Phe Phe His Leu Ala Ala Val Tyr Asp Met Gly Ala Asp Glu Glu
                85                  90                  95

Ala Gln Gln Ala Thr Asn Ile Glu Gly Thr Arg Ala Ala Val Asn Ala
            100                 105                 110

Ala Glu Ala Met Gly Ala Lys His Phe His Val Ser Ser Ile Ala
        115                 120                 125

Ala Ala Gly Leu Phe Lys Gly Ile Phe Arg Glu Asp Met Phe Glu Glu
    130                 135                 140

Ala Glu Lys Leu Asp His Pro Tyr Leu Arg Thr Lys His Glu Ser Glu
145                 150                 155                 160

Lys Val Val Arg Glu Glu Cys Lys Val Pro Phe Arg Ile Tyr Arg Pro
                165                 170                 175

Gly Met Val Ile Gly His Thr Ala Thr Gly Glu Met Asp Lys Val Asp
            180                 185                 190

Gly Pro Tyr Tyr Phe Phe Lys Met Ile Gln Lys Ile Arg His Ala Leu
        195                 200                 205

Pro Gln Trp Val Pro Thr Ile Gly Val Glu Gly Arg Leu Asn Ile
    210                 215                 220

Val Pro Val Asp Phe Val Asn Ala Met Asp His Ile Ala His Leu
225                 230                 235                 240

Glu Gly Glu Asp Gly Lys Cys Phe His Leu Val Asp Thr Asp Pro Tyr
                245                 250                 255

Lys Val Gly Glu Ile Leu Asn Ile Phe Ser Glu Ala Gly His Ala Pro
            260                 265                 270

Arg Met Gly Met Arg Ile Asp Ser Arg Met Phe Gly Phe Ile Pro Pro
        275                 280                 285

Phe Ile Arg Gln Ser Leu Lys Asn Leu Pro Pro Val Lys Arg Leu Thr
    290                 295                 300

Ser Ala Ile Leu Asp Asp Met Gly Ile Pro Pro Ser Val Met Ser Phe
305                 310                 315                 320

Ile Asn Tyr Pro Thr Arg Phe Asp Ala Arg Glu Thr Glu Arg Val Leu
                325                 330                 335

Lys Gly Thr Gly Ile Glu Val Pro Arg Leu Pro Asp Tyr Ala Pro Val
            340                 345                 350

Ile Trp Asp Tyr Trp Glu Arg Asn Leu Asp Pro Asp Leu Phe Lys Asp
        355                 360                 365

Arg Thr Leu Lys Gly Thr Val Glu Gly Arg Val Cys Val Thr Gly
    370                 375                 380

Ala Thr Ser Gly Ile Gly Leu Ala Thr Ala Gln Lys Leu Ala Asp Ala
385                 390                 395                 400

Gly Ala Ile Leu Val Ile Gly Ala Arg Lys Leu Glu Arg Leu Lys Glu
                405                 410                 415

Val Ala Ala Glu Leu Glu Ser Arg Gly Ala Ser Val His Ala Tyr Pro
            420                 425                 430

Cys Asp Phe Ser Asp Met Asp Ala Cys Asp Glu Phe Val Lys Thr Val
        435                 440                 445

Leu Asp Asn His Gly Gln Val Asp Val Leu Val Asn Asn Ala Gly Arg
    450                 455                 460

Ser Ile Arg Arg Ser Leu Asp Leu Ser Phe Asp Arg Phe His Asp Phe
465                 470                 475                 480

Glu Arg Thr Met Gln Leu Asn Tyr Phe Gly Ser Val Arg Leu Ile Met
                485                 490                 495
```

```
Gly Phe Ala Pro Lys Met Leu Glu Asn Arg Arg Gly His Val Val Asn
                500                 505                 510

Ile Ser Ser Ile Gly Val Leu Thr Asn Ala Pro Arg Phe Ser Ala Tyr
            515                 520                 525

Val Ala Ser Lys Ser Ala Leu Asp Ala Phe Ser Arg Cys Ala Ala Ser
        530                 535                 540

Glu Trp Ser Asp Arg Asn Val Thr Phe Thr Thr Ile Asn Met Pro Leu
545                 550                 555                 560

Val Lys Thr Pro Met Ile Ala Pro Thr Lys Ile Tyr Asp Ser Val Pro
                565                 570                 575

Thr Leu Thr Pro Asp Glu Ala Ala Thr Met Val Ala Asp Ala Ile Val
            580                 585                 590

Tyr Arg Pro Lys Arg Ile Ala Thr Arg Leu Gly Ile Phe Ala Gln Val
        595                 600                 605

Leu His Ala Leu Ala Pro Lys Met Ala Glu Ile Val Met Asn Thr Gly
    610                 615                 620

Tyr Arg Met Phe Pro Asp Ser Pro Ala Ala Gly Ser Arg Ser Gly
625                 630                 635                 640

Glu Lys Pro Lys Val Ser Ser Glu Gln Val Ala Phe Ala Ala Ile Met
                645                 650                 655

Arg Gly Ile Tyr Trp
            660

<210> SEQ ID NO 9
<211> LENGTH: 661
<212> TYPE: PRT
<213> ORGANISM: Marinobacter sp. ELB17
<220> FEATURE:
<223> OTHER INFORMATION: Short chain dehydrogenase

<400> SEQUENCE: 9

Met Asn Tyr Phe Val Thr Gly Thr Gly Phe Ile Gly Arg Phe Leu
1               5                   10                  15

Ile Ala Arg Leu Leu Ala Arg Gly Ala Ile Val His Val Leu Val Arg
            20                  25                  30

Glu Gln Ser Val Gln Lys Leu Ala Asp Leu Arg Glu Lys Leu Gly Ala
        35                  40                  45

Asp Glu Lys Gln Ile Lys Ala Val Val Gly Asp Leu Thr Ala Pro Gly
    50                  55                  60

Leu Gly Leu Asp Lys Lys Thr Leu Lys Gln Leu Ser Gly Lys Ile Asp
65                  70                  75                  80

His Phe Phe His Leu Ala Ala Ile Tyr Asp Met Ser Ala Ser Glu Glu
                85                  90                  95

Ser Gln Gln Ala Ala Asn Ile Asp Gly Thr Arg Ala Ala Val Ala Ala
            100                 105                 110

Ala Glu Ala Leu Gly Ala Gly Ile Phe His His Val Ser Ser Ile Ala
        115                 120                 125

Val Ala Gly Leu Phe Lys Gly Thr Phe Arg Glu Asp Met Phe Ala Glu
    130                 135                 140

Ala Gly Lys Leu Asp His Pro Tyr Phe Ser Thr Lys His Glu Ser Glu
145                 150                 155                 160

Arg Val Val Arg Asp Glu Cys Lys Leu Pro Phe Arg Ile Tyr Arg Pro
                165                 170                 175

Gly Met Val Ile Gly Asp Ser Ala Thr Gly Glu Met Asp Lys Val Asp
            180                 185                 190
```

```
Gly Pro Tyr Tyr Phe Lys Met Ile Gln Lys Ile Arg Gly Ala Leu
        195                 200                 205

Pro Gln Trp Val Pro Thr Ile Gly Leu Glu Gly Gly Arg Leu Asn Ile
    210                 215                 220

Val Pro Val Asn Phe Val Ala Asp Ala Leu Asp His Ile Ala His Leu
225                 230                 235                 240

Pro Asp Glu Asp Gly Lys Cys Phe His Leu Val Asp Ser Asp Pro Tyr
                245                 250                 255

Lys Val Gly Glu Ile Leu Asn Ile Phe Cys Glu Ala Gly His Ala Pro
                260                 265                 270

Lys Met Gly Met Arg Ile Asp Ser Arg Met Phe Gly Phe Val Pro Pro
                275                 280                 285

Phe Ile Arg Gln Ser Leu Lys Asn Leu Pro Pro Val Lys Arg Met Gly
    290                 295                 300

Arg Ala Leu Leu Asp Asp Leu Gly Ile Pro Ala Ser Val Leu Ser Phe
305                 310                 315                 320

Ile Asn Tyr Pro Thr Arg Phe Asp Ala Arg Glu Thr Glu Arg Val Leu
                325                 330                 335

Gln Gly Thr Gly Ile Glu Val Pro Arg Leu Pro Asp Tyr Ala Pro Val
                340                 345                 350

Ile Trp Asp Tyr Trp Glu Arg Asn Leu Asp Pro Asp Leu Phe Thr Asp
    355                 360                 365

Arg Thr Leu Arg Gly Thr Val Glu Gly Lys Val Cys Val Thr Gly
370                 375                 380

Ala Thr Ser Gly Ile Gly Leu Ala Thr Ala Glu Lys Leu Ala Asp Ala
385                 390                 395                 400

Gly Ala Ile Leu Val Ile Gly Ala Arg Thr Gln Glu Thr Leu Asp Gln
                405                 410                 415

Val Ser Ala Gln Leu Asn Ala Arg Gly Ala Asp Val His Ala Tyr Gln
                420                 425                 430

Cys Asp Phe Ala Asp Met Asp Ala Cys Asp Arg Phe Ile Gln Thr Val
            435                 440                 445

Ser Glu Asn His Gly Ala Val Asp Val Leu Ile Asn Asn Ala Gly Arg
    450                 455                 460

Ser Ile Arg Arg Ser Leu Asp Lys Ser Phe Asp Arg Phe His Asp Phe
465                 470                 475                 480

Glu Arg Thr Met Gln Leu Asn Tyr Phe Gly Ser Leu Arg Leu Ile Met
                485                 490                 495

Gly Phe Ala Pro Ala Met Leu Glu Arg Arg Gly His Ile Ile Asn
                500                 505                 510

Ile Ser Ser Ile Gly Val Leu Thr Asn Ala Pro Arg Phe Ser Ala Tyr
    515                 520                 525

Val Ala Ser Lys Ala Ala Leu Asp Ser Phe Ser Arg Cys Ala Ala Ala
    530                 535                 540

Glu Trp Ser Asp Arg His Val Cys Phe Thr Thr Ile Asn Met Pro Leu
545                 550                 555                 560

Val Lys Thr Pro Met Ile Ala Pro Thr Lys Ile Tyr Asp Ser Val Pro
                565                 570                 575

Thr Leu Ser Pro Glu Glu Ala Ala Asp Met Val Val Asn Ala Ile Val
                580                 585                 590

Tyr Arg Pro Lys Arg Ile Ala Thr Arg Met Gly Val Phe Ala Gln Val
                595                 600                 605
```

-continued

Leu Asn Ala Val Ala Pro Lys Ala Ser Glu Ile Leu Met Asn Thr Gly
        610                 615                 620

Tyr Lys Met Phe Pro Asp Ser Met Pro Lys Lys Gly Lys Glu Val Ser
625                 630                 635                 640

Ala Glu Lys Gly Ala Ser Thr Asp Gln Val Ala Phe Ala Ala Ile Met
                645                 650                 655

Arg Gly Ile His Trp
            660

<210> SEQ ID NO 10
<211> LENGTH: 661
<212> TYPE: PRT
<213> ORGANISM: Marinobacter algicola DG893
<220> FEATURE:
<223> OTHER INFORMATION: Short chain dehydrogenase

<400> SEQUENCE: 10

Met Asn Tyr Phe Leu Thr Gly Gly Thr Gly Phe Ile Gly Arg Phe Leu
1               5                   10                  15

Val Glu Lys Leu Leu Ala Arg Gly Gly Thr Val His Val Leu Val Arg
                20                  25                  30

Glu Gln Ser Gln Glu Lys Leu Asp Lys Leu Arg Glu Arg Trp Gly Ala
            35                  40                  45

Asp Glu Ser Arg Val Lys Ala Val Ile Gly Asp Leu Thr Ser Pro Asn
        50                  55                  60

Leu Gly Ile Asp Ala Lys Thr Met Lys Ser Leu Lys Gly Asn Ile Asp
65                  70                  75                  80

His Phe Phe His Leu Ala Ala Val Tyr Asp Met Gly Ala Asp Glu Lys
                85                  90                  95

Ser Gln Gln Ala Thr Asn Ile Glu Gly Thr His Ser Ala Val Asn Ala
            100                 105                 110

Ala Ala Ala Met Glu Ala Gly Cys Phe His His Val Ser Ser Ile Ala
        115                 120                 125

Ala Ala Gly Leu Phe Lys Gly Thr Phe Arg Glu Asp Met Phe Glu Glu
130                 135                 140

Ala Glu Lys Leu Asp His Pro Tyr Leu Leu Thr Lys His Glu Ser Glu
145                 150                 155                 160

Lys Val Val Arg Glu Ser Cys Lys Val Pro Phe Arg Ile Tyr Arg Pro
                165                 170                 175

Gly Met Val Val Gly His Ser Lys Thr Gly Glu Met Asp Lys Val Asp
            180                 185                 190

Gly Pro Tyr Tyr Phe Phe Lys Met Ile Gln Lys Ile Arg His Ala Leu
        195                 200                 205

Pro Gln Trp Val Pro Thr Ile Gly Ile Glu Gly Arg Leu Asn Ile
210                 215                 220

Val Pro Val Asp Phe Val Val Asn Ala Met Asp His Ile Ala His Leu
225                 230                 235                 240

Lys Gly Glu Asp Gly Asn Cys Phe His Leu Val Asp Ser Asp Pro Tyr
                245                 250                 255

Lys Val Gly Glu Ile Leu Asn Ile Phe Ser Glu Ala Gly His Ala Pro
            260                 265                 270

Arg Met Ala Met Arg Ile Asp Ser Arg Met Phe Gly Phe Val Pro Pro
        275                 280                 285

Phe Ile Arg Gln Ser Leu Lys Asn Leu Pro Pro Val Lys Arg Leu Thr
290                 295                 300

```
Thr Ala Leu Leu Asp Asp Met Gly Ile Pro Ser Val Leu Ser Phe
305                 310                 315                 320

Ile Asn Tyr Pro Thr Arg Phe Asp Ala Arg Glu Thr Glu Arg Val Leu
            325                 330                 335

Lys Asp Thr Gly Ile Val Val Pro Arg Leu Glu Ser Tyr Ala Ala Val
            340                 345                 350

Leu Trp Asp Phe Trp Glu Arg Asn Leu Asp Pro Asp Leu Phe Lys Asp
        355                 360                 365

Arg Thr Leu Arg Gly Thr Val Glu Gly Lys Val Cys Val Ile Thr Gly
370                 375                 380

Gly Thr Ser Gly Ile Gly Leu Ala Thr Ala Gln Lys Leu Ala Asp Ala
385                 390                 395                 400

Gly Ala Ile Leu Val Ile Gly Ala Arg Lys Lys Glu Arg Leu Met Glu
                405                 410                 415

Val Ala Ala Glu Leu Glu Ala Arg Gly Gly Asn Val His Ala Tyr Gln
                420                 425                 430

Cys Asp Phe Ala Asp Met Asp Asp Cys Asp Arg Phe Val Lys Thr Val
            435                 440                 445

Leu Asp Asn His Gly His Val Asp Val Leu Val Asn Asn Ala Gly Arg
450                 455                 460

Ser Ile Arg Arg Ser Leu Ala Leu Ser Phe Asp Arg Phe His Asp Phe
465                 470                 475                 480

Glu Arg Thr Met Gln Leu Asn Tyr Phe Gly Ser Val Arg Leu Ile Met
                485                 490                 495

Gly Phe Ala Pro Ala Met Leu Glu Arg Arg Gly His Val Val Asn
            500                 505                 510

Ile Ser Ser Ile Gly Val Leu Thr Asn Ala Pro Arg Phe Ser Ala Tyr
            515                 520                 525

Val Ala Ser Lys Ser Ala Leu Asp Thr Phe Ser Arg Cys Ala Ala Ala
530                 535                 540

Glu Trp Ser Asp Arg Asn Val Thr Phe Thr Thr Ile Asn Met Pro Leu
545                 550                 555                 560

Val Lys Thr Pro Met Ile Ala Pro Thr Lys Ile Tyr Asp Ser Val Pro
                565                 570                 575

Thr Leu Thr Pro Asp Glu Ala Ala Glu Met Val Ala Asp Ala Ile Val
            580                 585                 590

Tyr Arg Pro Lys Arg Ile Ala Thr Arg Leu Gly Ile Phe Ala Gln Val
        595                 600                 605

Met Gln Ala Leu Ala Pro Lys Met Gly Glu Ile Val Met Asn Thr Gly
610                 615                 620

Tyr Arg Met Phe Pro Asp Ser Pro Ala Ala Gly Ser Arg Ser Gly
625                 630                 635                 640

Ala Lys Pro Lys Val Ser Ser Glu Gln Val Ala Phe Ala Ala Ile Met
                645                 650                 655

Arg Gly Ile Tyr Trp
            660

<210> SEQ ID NO 11
<211> LENGTH: 661
<212> TYPE: PRT
<213> ORGANISM: Hahella chejuensis KCTC 2396
<220> FEATURE:
<223> OTHER INFORMATION: Short-chain alcohol dehydrogenase-like protein

<400> SEQUENCE: 11
```

-continued

```
Met Asn Tyr Phe Val Thr Gly Gly Thr Gly Phe Ile Gly Arg Phe Leu
1               5                   10                  15

Val Pro Lys Leu Leu Lys Arg Gly Gly Thr Val Tyr Leu Leu Val Arg
            20                  25                  30

Glu Ala Ser Leu Pro Lys Leu Asp Glu Leu Arg Glu Arg Trp Asn Ala
        35                  40                  45

Ser Asp Glu Gln Val Val Gly Val Gly Asp Leu Ala Gln Pro Met
    50                  55                  60

Leu Gly Val Ser Glu Lys Asp Ala Ala Met Leu Arg Gly Lys Val Gly
65                  70                  75                  80

His Phe Phe His Leu Ala Ala Ile Tyr Asp Met Gln Ala Ser Ala Glu
                85                  90                  95

Ser Gln Glu Gln Ala Asn Ile Glu Gly Thr Arg Asn Ala Val Lys Leu
            100                 105                 110

Ala Asp Ser Leu Lys Ala Ala Cys Phe His His Val Ser Ile Ala
            115                 120                 125

Ala Ala Gly Leu Tyr Arg Gly Ile Phe Arg Glu Asp Met Phe Glu Glu
        130                 135                 140

Ala Glu Lys Leu Asp Asn Pro Tyr Leu Arg Thr Lys His Glu Ser Glu
145                 150                 155                 160

Lys Val Val Arg Glu Glu Cys Gln Thr Pro Trp Arg Val Tyr Arg Pro
                165                 170                 175

Gly Met Val Val Gly His Ser Lys Thr Gly Glu Ile Asp Lys Ile Asp
            180                 185                 190

Gly Pro Tyr Tyr Phe Phe Lys Leu Ile Gln Lys Leu Arg Ser Ala Leu
        195                 200                 205

Pro Gln Trp Met Pro Thr Val Gly Leu Glu Gly Gly Arg Ile Asn Ile
    210                 215                 220

Val Pro Val Asp Phe Val Asp Ala Met Asp His Ile Ala His Ala
225                 230                 235                 240

Glu Gly Glu Asp Gly Lys Cys Phe His Leu Thr Asp Pro Asp Pro Tyr
                245                 250                 255

Lys Val Gly Glu Ile Leu Asn Ile Phe Ala Glu Ala Gly His Ala Pro
            260                 265                 270

Lys Met Ala Met Arg Ile Asp Ala Arg Met Phe Gly Phe Ile Pro Pro
        275                 280                 285

Met Ile Arg Gln Gly Ile Ala Arg Leu Pro Pro Val Gln Arg Met Lys
    290                 295                 300

Asn Ala Val Leu Asn Asp Leu Gly Ile Pro Asp Glu Val Met Ser Phe
305                 310                 315                 320

Ile Asn Tyr Pro Thr Arg Phe Asp Asn Arg Glu Thr Glu Arg Leu Leu
                325                 330                 335

Lys Gly Thr Ala Ile Ala Val Pro Arg Leu Gln Asp Tyr Ser Pro Ala
            340                 345                 350

Ile Trp Asp Tyr Trp Glu Arg His Leu Asp Pro Asp Leu His Lys Asp
        355                 360                 365

Arg Thr Leu Arg Gly Ala Val Glu Gly Arg Val Cys Val Ile Thr Gly
    370                 375                 380

Ala Thr Ser Gly Ile Gly Leu Ser Ala Ala Arg Lys Leu Ala Glu Ala
385                 390                 395                 400

Gly Ala Lys Val Val Ile Ala Ala Arg Thr Leu Glu Lys Leu Gln Glu
                405                 410                 415

Val Lys Lys Glu Leu Glu Glu Leu Gly Gly Glu Val Tyr Glu Tyr Ser
```

```
            420                 425                 430
Val Asp Leu Ser Asp Leu Glu Asp Cys Asp Arg Phe Val Ala Asn Val
            435                 440                 445
Leu Lys Asp Leu Gly His Val Asp Val Leu Val Asn Asn Ala Gly Arg
            450                 455                 460
Ser Ile Arg Arg Ser Ile Gln His Ala Phe Asp Arg Phe His Asp Phe
465                 470                 475                 480
Glu Arg Thr Met Gln Leu Asn Tyr Phe Gly Ser Leu Arg Leu Ile Met
                485                 490                 495
Gly Phe Ala Pro Ser Met Leu Glu Arg Arg Gly His Ile Val Asn
                    500                 505                 510
Ile Ser Ser Ile Gly Val Leu Thr Asn Ala Pro Arg Phe Ser Ala Tyr
                515                 520                 525
Val Ala Ser Lys Ala Ala Leu Asp Ala Phe Ser Arg Cys Ala Ala Ala
                530                 535                 540
Glu Phe Ser Asp Lys Asn Val Thr Phe Thr Thr Ile Asn Met Pro Leu
545                 550                 555                 560
Val Arg Thr Pro Met Ile Ser Pro Thr Lys Ile Tyr Asp Ser Val Pro
                565                 570                 575
Thr Leu Thr Pro Glu Ala Ala Asp Leu Val Ala Glu Ala Ile Ile
                    580                 585                 590
His Arg Pro Lys Arg Ile Ala Thr Arg Leu Gly Val Phe Ala Gln Val
                595                 600                 605
Leu His Ser Met Ala Pro Lys Phe Ser Glu Ile Ile Met Asn Thr Gly
                610                 615                 620
Phe Lys Met Phe Pro Asp Ser Ser Ala Ala Thr Gly Gly Lys Asp Gly
625                 630                 635                 640
Glu Lys Pro Lys Val Ser Thr Glu Gln Val Ala Phe Ala Ala Ile Met
                645                 650                 655
Arg Gly Ile His Trp
            660

<210> SEQ ID NO 12
<211> LENGTH: 346
<212> TYPE: PRT
<213> ORGANISM: Rhodococcus ruber
<220> FEATURE:
<223> OTHER INFORMATION: Secondary alcohol dehydrogenase

<400> SEQUENCE: 12

Met Lys Ala Leu Gln Tyr Thr Glu Ile Gly Ser Glu Pro Val Val Val
1               5                   10                  15
Asp Val Pro Thr Pro Ala Pro Gly Pro Gly Glu Ile Leu Leu Lys Val
                20                  25                  30
Thr Ala Ala Gly Leu Cys His Ser Asp Ile Phe Val Met Asp Met Pro
            35                  40                  45
Ala Glu Gln Tyr Ile Tyr Gly Leu Pro Leu Thr Leu Gly His Glu Gly
        50                  55                  60
Val Gly Thr Val Ala Glu Leu Gly Ala Gly Val Thr Gly Phe Glu Thr
65                  70                  75                  80
Gly Asp Ala Val Ala Val Tyr Gly Pro Trp Gly Cys Gly Ala Cys His
                85                  90                  95
Ala Cys Ala Arg Gly Arg Glu Asn Tyr Cys Thr Arg Ala Ala Glu Leu
            100                 105                 110
Gly Ile Thr Pro Pro Gly Leu Gly Ser Pro Gly Ser Met Ala Glu Tyr
```

```
                115                 120                 125
Met Ile Val Asp Ser Ala Arg His Leu Val Pro Ile Gly Asp Leu Asp
        130                 135                 140

Pro Val Ala Ala Val Pro Leu Thr Asp Ala Gly Leu Thr Pro Tyr His
145                 150                 155                 160

Ala Ile Ser Arg Val Leu Pro Leu Leu Gly Pro Gly Ser Thr Ala Val
                165                 170                 175

Val Ile Gly Val Gly Gly Leu Gly His Val Gly Ile Gln Ile Leu Arg
            180                 185                 190

Ala Val Ser Ala Ala Arg Val Ile Ala Val Asp Leu Asp Asp Asp Arg
        195                 200                 205

Leu Ala Leu Ala Arg Glu Val Gly Ala Asp Ala Ala Val Lys Ser Gly
210                 215                 220

Ala Gly Ala Ala Asp Ala Ile Arg Glu Leu Thr Gly Gly Glu Gly Ala
225                 230                 235                 240

Thr Ala Val Phe Asp Phe Val Gly Ala Gln Ser Thr Ile Asp Thr Ala
                245                 250                 255

Gln Gln Val Val Ala Ile Asp Gly His Ile Ser Val Val Gly Ile His
            260                 265                 270

Ala Gly Ala His Ala Lys Val Gly Phe Phe Met Ile Pro Phe Gly Ala
        275                 280                 285

Ser Val Val Thr Pro Tyr Trp Gly Thr Arg Ser Glu Leu Met Asp Val
290                 295                 300

Val Asp Leu Ala Arg Ala Gly Arg Leu Asp Ile His Thr Glu Thr Phe
305                 310                 315                 320

Thr Leu Asp Glu Gly Pro Thr Ala Tyr Arg Arg Leu Arg Glu Gly Ser
                325                 330                 335

Ile Arg Gly Arg Gly Val Val Pro Gly
            340                 345

<210> SEQ ID NO 13
<211> LENGTH: 352
<212> TYPE: PRT
<213> ORGANISM: Thermoanaerobacter brockii
<220> FEATURE:
<223> OTHER INFORMATION: NADP-dependent alcohol dehydrogenase

<400> SEQUENCE: 13

Met Lys Gly Phe Ala Met Leu Ser Ile Gly Lys Val Gly Trp Ile Glu
1               5                   10                  15

Lys Glu Lys Pro Ala Pro Gly Pro Phe Asp Ala Ile Val Arg Pro Leu
            20                  25                  30

Ala Val Ala Pro Cys Thr Ser Asp Ile His Thr Val Phe Glu Gly Ala
        35                  40                  45

Ile Gly Glu Arg His Asn Met Ile Leu Gly His Glu Ala Val Gly Glu
    50                  55                  60

Val Val Glu Val Gly Ser Glu Val Lys Asp Phe Lys Pro Gly Asp Arg
65                  70                  75                  80

Val Val Val Pro Ala Ile Thr Pro Asp Trp Arg Thr Ser Glu Val Gln
                85                  90                  95

Arg Gly Tyr His Gln His Ser Gly Gly Met Leu Ala Gly Trp Lys Phe
            100                 105                 110

Ser Asn Val Lys Asp Gly Val Phe Gly Glu Phe Phe His Val Asn Asp
        115                 120                 125

Ala Asp Met Asn Leu Ala His Leu Pro Lys Glu Ile Pro Leu Glu Ala
```

```
                    130                 135                 140
Ala Val Met Ile Pro Asp Met Met Thr Thr Gly Phe His Gly Ala Glu
145                 150                 155                 160

Leu Ala Asp Ile Glu Leu Gly Ala Thr Val Ala Val Leu Gly Ile Gly
                165                 170                 175

Pro Val Gly Leu Met Ala Val Ala Gly Ala Lys Leu Arg Gly Ala Gly
                180                 185                 190

Arg Ile Ile Ala Val Gly Ser Arg Pro Val Cys Val Asp Ala Ala Lys
                195                 200                 205

Tyr Tyr Gly Ala Thr Asp Ile Val Asn Tyr Lys Asp Gly Pro Ile Glu
                210                 215                 220

Ser Gln Ile Met Asn Leu Thr Glu Gly Lys Gly Val Asp Ala Ala Ile
225                 230                 235                 240

Ile Ala Gly Gly Asn Ala Asp Ile Met Ala Thr Ala Val Lys Ile Val
                245                 250                 255

Lys Pro Gly Gly Thr Ile Ala Asn Val Asn Tyr Phe Gly Glu Gly Glu
                260                 265                 270

Val Leu Pro Val Pro Arg Leu Glu Trp Gly Cys Gly Met Ala His Lys
                275                 280                 285

Thr Ile Lys Gly Gly Leu Cys Pro Gly Gly Arg Leu Arg Met Glu Arg
                290                 295                 300

Leu Ile Asp Leu Val Phe Tyr Lys Arg Val Asp Pro Ser Lys Leu Val
305                 310                 315                 320

Thr His Val Phe Arg Gly Phe Asp Asn Ile Glu Lys Ala Phe Met Leu
                325                 330                 335

Met Lys Asp Lys Pro Lys Asp Leu Ile Lys Pro Val Val Ile Leu Ala
                340                 345                 350

<210> SEQ ID NO 14
<211> LENGTH: 252
<212> TYPE: PRT
<213> ORGANISM: Lactobacillus brevis
<220> FEATURE:
<223> OTHER INFORMATION: R-specific alcohol dehydrogenase

<400> SEQUENCE: 14

Met Ser Asn Arg Leu Asp Gly Lys Val Ala Ile Ile Thr Gly Gly Thr
1               5                   10                  15

Leu Gly Ile Gly Leu Ala Ile Ala Thr Lys Phe Val Glu Glu Gly Ala
                20                  25                  30

Lys Val Met Ile Thr Gly Arg His Ser Asp Val Gly Glu Lys Ala Ala
                35                  40                  45

Lys Ser Val Gly Thr Pro Asp Gln Ile Gln Phe Phe Gln His Asp Ser
                50                  55                  60

Ser Asp Glu Asp Gly Trp Thr Lys Leu Phe Asp Ala Thr Glu Lys Ala
65                  70                  75                  80

Phe Gly Pro Val Ser Thr Leu Val Asn Asn Ala Gly Ile Ala Val Asn
                85                  90                  95

Lys Ser Val Glu Glu Thr Thr Thr Ala Glu Trp Arg Lys Leu Leu Ala
                100                 105                 110

Val Asn Leu Asp Gly Val Phe Phe Gly Thr Arg Leu Gly Ile Gln Arg
                115                 120                 125

Met Lys Asn Lys Gly Leu Gly Ala Ser Ile Ile Asn Met Ser Ser Ile
                130                 135                 140

Glu Gly Phe Val Gly Asp Pro Ser Leu Gly Ala Tyr Asn Ala Ser Lys
```

```
                145                 150                 155                 160
Gly Ala Val Arg Ile Met Ser Lys Ser Ala Leu Asp Cys Ala Leu
                    165                 170                 175
Lys Asp Tyr Asp Val Arg Val Asn Thr Val His Pro Gly Tyr Ile Lys
                    180                 185                 190
Thr Pro Leu Val Asp Asp Leu Pro Gly Ala Glu Glu Ala Met Ser Gln
                    195                 200                 205
Arg Thr Lys Thr Pro Met Gly His Ile Gly Glu Pro Asn Asp Ile Ala
                    210                 215                 220
Tyr Ile Cys Val Tyr Leu Ala Ser Asn Glu Ser Lys Phe Ala Thr Gly
225                 230                 235                 240
Ser Glu Phe Val Val Asp Gly Gly Tyr Thr Ala Gln
                    245                 250
```

<210> SEQ ID NO 15
<211> LENGTH: 347
<212> TYPE: PRT
<213> ORGANISM: Lactobacillus kefiri
<220> FEATURE:
<223> OTHER INFORMATION: NADH-dependent (S)-specific alcohol
      dehydrogenase

<400> SEQUENCE: 15

```
Met Lys Ser Thr Ile Phe Val Lys Pro Gly Lys Val Glu Ile Gln Asn
1               5                   10                  15
Ile Asp Lys Pro Thr Ile Gln Ala Asp Asp Ala Ile Leu His Ile
                20                  25                  30
Val Arg Ala Cys Val Cys Gly Ser Asp Leu Trp Ala Tyr Arg Asp Leu
                35                  40                  45
Glu Asp Lys Glu Pro Asn Ser Glu Asn Thr Gly His Glu Ala Ile Ala
50                  55                  60
Ile Val Asp Gln Val Gly Lys Asn Ile Thr Thr Val Lys Pro Gly Asp
65                  70                  75                  80
Phe Val Ile Ala Pro Phe Thr His Gly Cys Gly His Cys Ala Ala Cys
                85                  90                  95
Arg Ala Gly Tyr Glu Gly Ser Cys Gln Ser His Ser Asp Asn Phe Ser
                100                 105                 110
Ala Gly Tyr Gln Ala Glu Tyr Val Arg Tyr Gln His Ala Glu Trp Ser
                115                 120                 125
Leu Val Lys Ile Pro Gly Lys Pro Glu Asp Tyr Ser Asp Gly Met Leu
130                 135                 140
Asn Ser Leu Leu Thr Leu Ala Asp Val Met Ala Thr Gly Tyr His Ala
145                 150                 155                 160
Ala Arg Val Ala Asn Val Lys Pro Gly Asp Thr Val Val Val Gly
                    165                 170                 175
Asp Gly Ala Val Gly Leu Cys Gly Val Ile Ala Ser Gln Met Arg Gly
                180                 185                 190
Ala Ser Arg Ile Ile Ala Met Ser Arg His Glu Asp Arg Gln Lys Leu
                    195                 200                 205
Ala Thr Glu Phe Gly Ala Thr Asp Ile Val Pro Glu Arg Gly Asp Glu
                210                 215                 220
Ala Val Ala Lys Val Met Ala Leu Thr Asn Gly Ala Gly Ala Asp Ala
225                 230                 235                 240
Val Leu Glu Cys Val Gly Ser Glu Leu Ser Thr Asp Thr Ala Met Lys
                    245                 250                 255
```

```
Val Ala Arg Pro Gly Ala Thr Val Arg Val Gly Leu Pro His Thr
            260                 265                 270

Lys Lys Thr Asp Leu Thr Asn Ser Phe Tyr Ser Asn Leu Ala Ile Ala
        275                 280                 285

Gly Gly Pro Ala Ser Val Thr Thr Tyr Asp Lys Ser Val Leu Leu Lys
    290                 295                 300

Ala Val Leu Asp Gly Asp Ile His Pro Gly Lys Val Phe Thr Lys Arg
305                 310                 315                 320

Phe Thr Leu Asp Glu Ile Asp Asp Ala Tyr Gln Ala Met Ala Lys Arg
                325                 330                 335

Glu Ala Ile Lys Ser Leu Val Val Ala Gln Lys
            340                 345
```

<210> SEQ ID NO 16
<211> LENGTH: 346
<212> TYPE: PRT
<213> ORGANISM: Lactobacillus brevis subsp. gravesensis ATCC 27305
<220> FEATURE:
<223> OTHER INFORMATION: NADH-dependent (S)-specific alcohol
      dehydrogenase

<400> SEQUENCE: 16

```
Met Lys Thr Thr Leu Phe Val Lys Pro Gly Lys Val Thr Val Lys Asn
1               5                   10                  15

Val Asp Lys Pro Val Ile Glu Lys Pro Asp Asp Val Ile Leu His Val
            20                  25                  30

Val Arg Ala Cys Val Cys Gly Ser Asp Leu Trp Ser Tyr Arg Gly Leu
        35                  40                  45

Asp Glu Lys Ala Ala Asn Ser Glu Asn Asn Gly His Glu Ala Ile Gly
    50                  55                  60

Ile Val Glu Glu Val Gly Lys Ala Ile Thr Thr Val Arg Pro Gly Asp
65                  70                  75                  80

Phe Val Ile Ala Pro Phe Thr His Gly Cys Gly His Cys Ala Ala Cys
                85                  90                  95

Arg Ala Gly Tyr Glu Gly Ser Cys Gln Ser His Ser Asp Asn Phe Ser
            100                 105                 110

Ser Gly Tyr Gln Ala Glu Tyr Val Arg Tyr Gln His Ala Glu Trp Ser
        115                 120                 125

Leu Val Lys Ile Pro Gly Ser Pro Val Asp Tyr Ser Asp Gly Met Leu
    130                 135                 140

Asn Ser Leu Leu Ser Leu Ala Asp Val Met Ala Thr Gly Tyr His Ala
145                 150                 155                 160

Ala Arg Val Ala Asn Val Lys Pro Gly Asp Thr Val Ala Val Val Gly
                165                 170                 175

Asp Gly Ala Val Gly Leu Cys Gly Val Ile Ala Ala Gln Leu Arg Gly
            180                 185                 190

Ala Lys Arg Ile Ile Ala Met Ser Arg His Glu Asp Arg Gln Lys Leu
        195                 200                 205

Ala Thr Glu Phe Gly Ala Thr Asp Ile Val Pro Glu Arg Gly Asp Asp
    210                 215                 220

Ala Val Lys Lys Val Met Ala Leu Thr Asn Gly Asp Gly Ala Asp Ala
225                 230                 235                 240

Val Leu Glu Cys Val Gly Thr Glu Leu Ser Thr Asp Thr Ala Leu Lys
                245                 250                 255

Ile Ala Arg Pro Gly Ala Ile Ile Gly Arg Val Gly Leu Pro His Thr
            260                 265                 270
```

```
Ala Lys Thr Asp Leu Ala Ala Pro Phe Tyr Gln Asn Thr Ala Phe Ala
            275                 280                 285

Gly Gly Pro Ala Ser Val Thr Thr Tyr Asp Lys Ser Val Leu Leu Lys
        290                 295                 300

Ala Val Leu Asp Gly Asp Ile His Pro Gly Lys Val Phe Thr Glu Arg
305                 310                 315                 320

Phe Gly Leu Asp Lys Ile Asp Asp Ala Tyr Gln Ala Met Val Lys Arg
                325                 330                 335

Glu Ala Ile Lys Ser Leu Val Val Ile Asp
                340                 345

<210> SEQ ID NO 17
<211> LENGTH: 252
<212> TYPE: PRT
<213> ORGANISM: Lactobacillus kefiri
<220> FEATURE:
<223> OTHER INFORMATION: NADPH dependent R-specific alcohol
      dehydrogenase

<400> SEQUENCE: 17

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Ser
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Phe Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Tyr Ile Lys
            180                 185                 190

Thr Pro Leu Val Asp Asp Leu Glu Gly Ala Glu Glu Met Met Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250

<210> SEQ ID NO 18
<211> LENGTH: 277
<212> TYPE: PRT
```

<213> ORGANISM: Rattus norvegicus
<220> FEATURE:
<223> OTHER INFORMATION: Carbonyl reductase

<400> SEQUENCE: 18

```
Met Ser Ser Cys Ser Arg Val Ala Leu Val Thr Gly Ala Asn Lys Gly
1               5                   10                  15

Ile Gly Phe Ala Ile Thr Arg Asp Leu Cys Arg Lys Phe Ser Gly Asp
            20                  25                  30

Val Val Leu Thr Ala Arg Asp Glu Ala Arg Gly Arg Ala Ala Val Lys
        35                  40                  45

Gln Leu Gln Ala Glu Gly Leu Ser Pro Arg Phe His Gln Leu Asp Ile
    50                  55                  60

Asp Asn Pro Gln Ser Ile Arg Ala Leu Arg Asp Phe Leu Arg Lys Glu
65                  70                  75                  80

Tyr Gly Gly Leu Asn Val Leu Val Asn Asn Ala Gly Ile Ala Phe Arg
                85                  90                  95

Met Asp Asp Pro Thr Pro Phe Asp Val Gln Ala Glu Val Thr Leu Lys
            100                 105                 110

Thr Asn Phe Phe Ala Thr Arg Asn Val Cys Thr Glu Leu Leu Pro Ile
        115                 120                 125

Met Lys Pro His Gly Arg Val Val Asn Val Ser Ser Leu Gln Gly Leu
    130                 135                 140

Lys Ala Leu Glu Asn Cys Ser Glu Asp Leu Gln Glu Arg Phe Arg Cys
145                 150                 155                 160

Asp Thr Leu Thr Glu Gly Asp Leu Val Asp Leu Met Lys Lys Phe Val
                165                 170                 175

Glu Asp Thr Lys Asn Glu Val His Glu Arg Glu Gly Trp Pro Asp Ser
            180                 185                 190

Ala Tyr Gly Val Ser Lys Leu Gly Val Thr Val Leu Thr Arg Ile Leu
        195                 200                 205

Ala Arg Gln Leu Asp Glu Lys Arg Lys Ala Asp Arg Ile Leu Leu Asn
    210                 215                 220

Ala Cys Cys Pro Gly Trp Val Lys Thr Asp Met Ala Arg Asp Gln Gly
225                 230                 235                 240

Ser Arg Thr Val Glu Glu Gly Ala Glu Thr Pro Val Tyr Leu Ala Leu
                245                 250                 255

Leu Pro Pro Asp Ala Thr Glu Pro His Gly Gln Leu Val Arg Asp Lys
            260                 265                 270

Val Val Gln Thr Trp
        275
```

<210> SEQ ID NO 19
<211> LENGTH: 397
<212> TYPE: PRT
<213> ORGANISM: Castellaniella defragrans
<220> FEATURE:
<223> OTHER INFORMATION: linalool dehydratase-isomerase

<400> SEQUENCE: 19

```
Met Arg Phe Thr Leu Lys Thr Thr Ala Ile Val Ser Ala Ala Ala Leu
1               5                   10                  15

Leu Ala Gly Phe Gly Pro Pro Arg Ala Ala Glu Leu Pro Pro Gly
            20                  25                  30

Arg Leu Ala Thr Thr Glu Asp Tyr Phe Ala Gln Gln Ala Lys Gln Ala
        35                  40                  45
```

Val Thr Pro Asp Val Met Ala Gln Leu Ala Tyr Met Asn Tyr Ile Asp
 50                  55                  60

Phe Ile Ser Pro Phe Tyr Ser Arg Gly Cys Ser Phe Glu Ala Trp Glu
 65                  70                  75                  80

Leu Lys His Thr Pro Gln Arg Val Ile Lys Tyr Ser Ile Ala Phe Tyr
                 85                  90                  95

Ala Tyr Gly Leu Ala Ser Val Ala Leu Ile Asp Pro Lys Leu Arg Ala
            100                 105                 110

Leu Ala Gly His Asp Leu Asp Ile Ala Val Ser Lys Met Lys Cys Lys
            115                 120                 125

Arg Val Trp Gly Asp Trp Glu Glu Asp Gly Phe Gly Thr Asp Pro Ile
130                 135                 140

Glu Lys Glu Asn Ile Met Tyr Lys Gly His Leu Asn Leu Met Tyr Gly
145                 150                 155                 160

Leu Tyr Gln Leu Val Thr Gly Ser Arg Arg Tyr Glu Ala Glu His Ala
                165                 170                 175

His Leu Thr Arg Ile Ile His Asp Glu Ile Ala Ala Asn Pro Phe Ala
            180                 185                 190

Gly Ile Val Cys Glu Pro Asp Asn Tyr Phe Val Gln Cys Asn Ser Val
            195                 200                 205

Ala Tyr Leu Ser Leu Trp Val Tyr Asp Arg Leu His Gly Thr Asp Tyr
210                 215                 220

Arg Ala Ala Thr Arg Ala Trp Leu Asp Phe Ile Gln Lys Asp Leu Ile
225                 230                 235                 240

Asp Pro Glu Arg Gly Ala Phe Tyr Leu Ser Tyr His Pro Glu Ser Gly
                245                 250                 255

Ala Val Lys Pro Trp Ile Ser Ala Tyr Thr Thr Ala Trp Thr Leu Ala
            260                 265                 270

Met Val His Gly Met Asp Pro Ala Phe Ser Glu Arg Tyr Tyr Pro Arg
275                 280                 285

Phe Lys Gln Thr Phe Val Glu Val Tyr Asp Glu Gly Arg Lys Ala Arg
290                 295                 300

Val Arg Glu Thr Ala Gly Thr Asp Asp Ala Asp Gly Val Gly Leu
305                 310                 315                 320

Ala Ser Ala Phe Thr Leu Leu Leu Ala Arg Glu Met Gly Asp Gln Gln
                325                 330                 335

Leu Phe Asp Gln Leu Leu Asn His Leu Glu Pro Ala Lys Pro Ser
            340                 345                 350

Ile Val Ser Ala Ser Leu Arg Tyr Glu His Pro Gly Ser Leu Leu Phe
            355                 360                 365

Asp Glu Leu Leu Phe Leu Ala Lys Val His Ala Gly Phe Gly Ala Leu
370                 375                 380

Leu Arg Met Pro Pro Pro Ala Ala Lys Leu Ala Gly Lys
385                 390                 395

<210> SEQ ID NO 20
<211> LENGTH: 661
<212> TYPE: PRT
<213> ORGANISM: Marinobacter sp.
<220> FEATURE:
<223> OTHER INFORMATION: Fatty acyl-CoA reductase

<400> SEQUENCE: 20

Met Asn Tyr Phe Val Thr Gly Gly Thr Gly Phe Ile Gly Arg Phe Leu
 1               5                  10                  15

```
Ile Ala Lys Leu Leu Ala Arg Gly Ala Ile Val His Val Leu Val Arg
            20                  25                  30
Glu Gln Ser Val Gln Lys Leu Ala Asp Leu Arg Glu Lys Leu Gly Ala
        35                  40                  45
Asp Glu Lys Gln Ile Lys Ala Val Val Gly Asp Leu Thr Ala Pro Ser
50                  55                  60
Leu Gly Leu Asp Lys Lys Thr Leu Lys Gln Leu Ser Gly Lys Ile Asp
65                  70                  75                  80
His Phe Phe His Leu Ala Ala Ile Tyr Asp Met Ser Ala Ser Glu Glu
                85                  90                  95
Ser Gln Gln Ala Ala Asn Ile Asp Gly Thr Arg Ala Ala Val Ala Ala
            100                 105                 110
Ala Glu Ala Leu Glu Ala Gly Ile Phe His His Val Ser Ser Ile Ala
        115                 120                 125
Val Ala Gly Leu Phe Lys Gly Thr Phe Arg Glu Asp Met Phe Ala Glu
    130                 135                 140
Ala Gly Lys Leu Asp His Pro Tyr Phe Arg Thr Lys His Glu Ser Glu
145                 150                 155                 160
Arg Val Val Arg Asp Asp Cys Lys Val Pro Phe Arg Ile Tyr Arg Pro
                165                 170                 175
Gly Leu Val Ile Gly Asp Ser Ala Thr Gly Asp Met Asp Lys Val Asp
            180                 185                 190
Gly Pro Tyr Tyr Phe Phe Lys Met Ile Gln Lys Ile Arg Gly Ala Leu
        195                 200                 205
Pro Gln Trp Val Pro Thr Ile Gly Ile Glu Gly Gly Arg Leu Asn Ile
    210                 215                 220
Val Pro Val Asn Phe Val Ala Asp Ala Leu Asp His Ile Ala His Leu
225                 230                 235                 240
Pro Asn Glu Asp Gly Lys Cys Phe His Leu Val Asp Ser Asp Pro Tyr
                245                 250                 255
Lys Val Gly Glu Ile Leu Asn Ile Phe Cys Glu Ala Gly His Ala Pro
            260                 265                 270
Lys Met Gly Met Arg Ile Asp Ser Arg Met Phe Gly Phe Val Pro Pro
        275                 280                 285
Phe Ile Arg Gln Ser Leu Lys Asn Leu Pro Pro Val Lys Arg Met Gly
    290                 295                 300
Arg Ala Leu Leu Asp Asp Leu Gly Ile Pro Ala Ser Val Leu Ser Phe
305                 310                 315                 320
Ile Asn Tyr Pro Thr Arg Phe Asp Ala Arg Glu Thr Glu Arg Val Leu
                325                 330                 335
Gln Gly Thr Gly Ile Glu Val Pro Arg Leu Pro Asp Tyr Ala Pro Val
            340                 345                 350
Ile Trp Asp Tyr Trp Glu Arg Asn Leu Asp Pro Asp Leu Phe Lys Asp
        355                 360                 365
Arg Thr Leu Arg Gly Thr Val Glu Gly Lys Val Cys Val Val Thr Gly
    370                 375                 380
Ala Thr Ser Gly Ile Gly Leu Ala Thr Ala Glu Lys Leu Ala Asp Ala
385                 390                 395                 400
Gly Ala Ile Leu Val Ile Gly Ala Arg Thr Gln Glu Thr Leu Asp Gln
                405                 410                 415
Val Ser Ala Gln Leu Asn Ala Arg Gly Ala Asp Val His Ala Tyr Gln
            420                 425                 430
Cys Asp Phe Ala Asp Met Asp Ala Cys Asp Arg Phe Ile Gln Thr Val
```

```
                    435                 440                 445
Ser Glu Asn His Gly Ala Val Asp Val Leu Ile Asn Asn Ala Gly Arg
    450                 455                 460

Ser Ile Arg Arg Ser Leu Asp Lys Ser Phe Asp Arg Phe His Asp Phe
465                 470                 475                 480

Glu Arg Thr Met Gln Leu Asn Tyr Phe Gly Ser Leu Arg Leu Ile Met
                    485                 490                 495

Gly Phe Ala Pro Ala Met Leu Glu Arg Arg Gly His Ile Ile Asn
                500                 505                 510

Ile Ser Ser Ile Gly Val Leu Thr Asn Ser Pro Arg Phe Ser Ala Tyr
            515                 520                 525

Val Ala Ser Lys Ser Ala Leu Asp Ser Phe Ser Arg Cys Ala Ala Ala
        530                 535                 540

Glu Trp Ser Asp Arg Arg Val Cys Phe Thr Thr Ile Asn Met Pro Leu
545                 550                 555                 560

Val Lys Thr Pro Met Ile Ala Pro Thr Lys Ile Tyr Asp Ser Val Pro
                    565                 570                 575

Thr Leu Ser Pro Glu Glu Ala Ala Asp Met Val Val Asn Ala Ile Val
                580                 585                 590

Tyr Arg Pro Lys Arg Ile Ala Thr Arg Met Gly Val Phe Ala Gln Val
            595                 600                 605

Leu Asn Ala Val Ala Pro Lys Ala Ser Glu Ile Leu Met Asn Thr Gly
        610                 615                 620

Tyr Lys Met Phe Pro Asp Ser Met Pro Lys Lys Gly Lys Glu Val Ser
625                 630                 635                 640

Ala Glu Lys Gly Ala Ser Thr Asp Gln Val Ala Phe Ala Ala Ile Met
                    645                 650                 655

Arg Gly Ile His Trp
            660

<210> SEQ ID NO 21
<211> LENGTH: 679
<212> TYPE: PRT
<213> ORGANISM: Marinobacter adhaerens
<220> FEATURE:
<223> OTHER INFORMATION: Short chain dehydrogenase

<400> SEQUENCE: 21

Met Gly Ala Gly Met Asp Arg Gln Gln Gln Ser Asn Arg Gln Gly Gly
1               5                   10                  15

Arg Leu Met Asn Tyr Phe Leu Thr Gly Thr Gly Phe Ile Gly Arg
            20                  25                  30

Phe Leu Val Glu Lys Leu Leu Ala Arg Gly Gly Thr Val His Val Leu
        35                  40                  45

Val Arg Glu Gln Ser Gln Asp Lys Leu Asp Lys Leu Arg Glu Arg Trp
    50                  55                  60

Gly Ala Asp Glu Thr Gln Val Lys Ala Val Ile Gly Asp Leu Thr Ser
65                  70                  75                  80

Lys Asn Leu Gly Ile Asp Ala Lys Thr Met Lys Ala Leu Lys Gly Lys
                    85                  90                  95

Ile Asp His Phe Phe His Leu Ala Ala Val Tyr Asp Met Gly Ala Asp
                100                 105                 110

Glu Glu Ala Gln Gln Ala Thr Asn Ile Glu Gly Thr Arg Ala Ala Val
            115                 120                 125

Asn Ala Ala Glu Ala Met Gly Ala Lys His Phe His His Val Ser Ser
```

-continued

```
            130                 135                 140
Ile Ala Ala Ala Gly Leu Phe Lys Gly Ile Phe Arg Glu Asp Met Phe
145                 150                 155                 160

Glu Glu Ala Glu Lys Leu Asp His Pro Tyr Leu Arg Thr Lys His Glu
                165                 170                 175

Ser Glu Lys Val Val Arg Glu Cys Lys Val Pro Phe Arg Ile Tyr
                180                 185                 190

Arg Pro Gly Met Val Ile Gly His Thr Ser Thr Gly Glu Met Asp Lys
                195                 200                 205

Val Asp Gly Pro Tyr Tyr Phe Phe Lys Met Ile Gln Lys Ile Arg His
        210                 215                 220

Ala Leu Pro Gln Trp Val Pro Thr Ile Gly Val Glu Gly Gly Arg Leu
225                 230                 235                 240

Asn Ile Val Pro Val Asp Phe Val Val Asn Ala Met Asp His Ile Ala
                245                 250                 255

His Leu Glu Gly Glu Asp Gly Lys Cys Phe His Leu Val Asp Thr Asp
                260                 265                 270

Pro Tyr Lys Val Gly Glu Ile Leu Asn Ile Phe Ser Glu Ala Gly His
                275                 280                 285

Ala Pro Arg Met Gly Met Arg Ile Asp Ser Arg Met Phe Gly Phe Ile
290                 295                 300

Pro Pro Phe Ile Arg Gln Ser Leu Lys Asn Leu Pro Pro Val Lys Arg
305                 310                 315                 320

Leu Thr Ser Ala Ile Leu Asp Asp Met Gly Ile Pro Pro Ser Val Met
                325                 330                 335

Ser Phe Ile Asn Tyr Pro Thr Arg Phe Asp Ala Arg Glu Thr Glu Arg
                340                 345                 350

Val Leu Lys Gly Thr Gly Ile Glu Val Pro Arg Leu Pro Asp Tyr Ala
                355                 360                 365

Pro Val Ile Trp Asp Tyr Trp Glu Arg Asn Leu Asp Pro Asp Leu Phe
        370                 375                 380

Lys Asp Arg Thr Leu Lys Gly Thr Val Glu Gly Arg Val Cys Val Val
385                 390                 395                 400

Thr Gly Ala Thr Ser Gly Ile Gly Leu Ala Thr Ala Gln Lys Leu Ala
                405                 410                 415

Asp Ala Gly Ala Ile Leu Val Ile Gly Ala Arg Lys Leu Glu Arg Leu
                420                 425                 430

Lys Glu Val Ala Ala Glu Leu Glu Ser Arg Gly Ala Ser Val His Ala
                435                 440                 445

Tyr Pro Cys Asp Phe Ser Asp Met Asp Ala Cys Asp Glu Phe Val Lys
        450                 455                 460

Thr Val Leu Asp Asn His Gly Gln Val Asp Leu Val Asn Asn Ala
465                 470                 475                 480

Gly Arg Ser Ile Arg Arg Ser Leu Asp Leu Ser Phe Asp Arg Phe His
                485                 490                 495

Asp Phe Glu Arg Thr Met Gln Leu Asn Tyr Phe Gly Ser Val Arg Leu
                500                 505                 510

Ile Met Gly Phe Ala Pro Lys Met Leu Glu Asn Arg Arg Gly His Val
                515                 520                 525

Val Asn Ile Ser Ser Ile Gly Val Leu Thr Asn Ala Pro Arg Phe Ser
        530                 535                 540

Ala Tyr Val Ala Ser Lys Ser Ala Leu Asp Ala Phe Ser Arg Cys Ala
545                 550                 555                 560
```

Ala Ser Glu Trp Ser Asp Arg Asn Val Thr Phe Thr Thr Ile Asn Met
            565                 570                 575

Pro Leu Val Lys Thr Pro Met Ile Ala Pro Thr Lys Ile Tyr Asp Ser
            580                 585                 590

Val Pro Thr Leu Thr Pro Asp Glu Ala Thr Met Val Ala Asp Ala
            595                 600                 605

Ile Val Tyr Arg Pro Lys Arg Ile Ala Thr Arg Leu Gly Ile Phe Ala
            610                 615                 620

Gln Val Leu His Ala Leu Ala Pro Lys Met Ala Glu Ile Val Met Asn
625                 630                 635                 640

Thr Gly Tyr Arg Met Phe Pro Asp Ser Pro Ala Ala Gly Ser Arg
            645                 650                 655

Ser Gly Glu Lys Pro Lys Val Ser Ser Glu Gln Val Ala Phe Ala Ala
            660                 665                 670

Ile Met Arg Gly Ile Tyr Trp
            675

<210> SEQ ID NO 22
<211> LENGTH: 661
<212> TYPE: PRT
<213> ORGANISM: Marinobacter santoriniensis NKSG1
<220> FEATURE:
<223> OTHER INFORMATION: Short chain dehydrogenase

<400> SEQUENCE: 22

Met Asn Tyr Phe Leu Thr Gly Gly Thr Gly Phe Ile Gly Arg Phe Leu
1               5                   10                  15

Val Glu Lys Leu Leu Ala Arg Gly Gly Thr Ile His Val Leu Val Arg
            20                  25                  30

Glu Gln Ser Gln Asp Lys Leu Gln Met Leu Arg Glu Arg Trp Gly Ala
        35                  40                  45

Asp Asp Ser Gln Val Lys Ala Val Ile Gly Asp Leu Thr Ser Pro Asn
    50                  55                  60

Leu Gly Ile Asp Ser Ser Thr Leu Glu Ser Leu Lys Gly Glu Ile Asp
65                  70                  75                  80

His Phe Phe His Leu Ala Ala Val Tyr Asp Met Gly Ala Asp Glu Glu
                85                  90                  95

Ser Gln Gln Ile Ala Asn Ile Glu Gly Thr Arg Ala Ala Val Gln Ala
            100                 105                 110

Ala Glu Ala Met Gly Ala Lys His Phe His His Val Ser Ser Ile Ala
        115                 120                 125

Ala Ala Gly Leu Phe Lys Gly Ile Phe Arg Glu Asp Met Phe Glu Glu
    130                 135                 140

Ala Glu Lys Leu Asp His Pro Tyr Leu Arg Thr Lys His Glu Ser Glu
145                 150                 155                 160

Lys Val Val Arg Glu Glu Cys Lys Val Pro Phe Arg Val Tyr Arg Pro
                165                 170                 175

Gly Met Val Ile Gly His Ser Lys Thr Gly Glu Met Asp Lys Val Asp
            180                 185                 190

Gly Pro Tyr Tyr Phe Phe Lys Met Ile Gln Lys Ile Arg His Ala Leu
        195                 200                 205

Pro Gln Trp Val Pro Thr Ile Gly Ile Glu Gly Gly Arg Leu Asn Ile
    210                 215                 220

Val Pro Val Asp Phe Val Val Asp Ala Leu Asp His Ile Ala His Leu
225                 230                 235                 240

```
Glu Gly Glu Asp Gly Asn Cys Phe His Leu Val Asp Ser Asp Pro Tyr
                245                 250                 255
Lys Val Gly Glu Ile Leu Asn Ile Phe Ser Glu Ala Gly His Ala Pro
            260                 265                 270
Lys Met Gly Met Arg Ile Asp Ser Arg Met Phe Gly Phe Ile Pro Pro
        275                 280                 285
Phe Ile Arg Gln Ser Leu Lys Asn Leu Pro Pro Val Lys Arg Leu Thr
290                 295                 300
Ser Ala Val Leu Asp Asp Met Gly Ile Pro Ser Val Met Ser Phe
305                 310                 315                 320
Ile Asn Tyr Pro Thr Arg Phe Asp Ala Arg Glu Thr Glu Arg Val Leu
                325                 330                 335
Lys Asp Ser Gly Ile Glu Val Pro Arg Leu Pro Asp Tyr Ala Pro Val
            340                 345                 350
Ile Trp Asp Tyr Trp Glu Arg Asn Leu Asp Pro Asp Leu Phe Lys Asp
        355                 360                 365
Arg Thr Leu Arg Gly Thr Val Glu Gly Arg Val Cys Val Val Thr Gly
370                 375                 380
Ala Thr Ser Gly Ile Gly Leu Ala Thr Ala Gln Lys Leu Ala Asp Ala
385                 390                 395                 400
Gly Ala Ile Leu Val Ile Gly Ala Arg Lys Leu Glu Arg Leu Lys Glu
                405                 410                 415
Val Ala Ala Glu Leu Glu Ser Arg Gly Ala Ser Val His Ala Tyr Pro
            420                 425                 430
Cys Asp Phe Ser Asp Met Glu Ala Cys Asp Glu Phe Val Lys Thr Val
        435                 440                 445
Leu Asp Asn His Gly His Val Asp Val Leu Val Asn Asn Ala Gly Arg
450                 455                 460
Ser Ile Arg Arg Ser Leu Asp Leu Ser Phe Asp Arg Phe His Asp Phe
465                 470                 475                 480
Glu Arg Thr Met Gln Leu Asn Tyr Phe Gly Ser Val Arg Leu Ile Met
                485                 490                 495
Gly Phe Ala Gln Thr Met Leu Asp Arg Arg Gly His Val Val Asn
            500                 505                 510
Ile Ser Ser Ile Gly Val Leu Thr Asn Ala Pro Arg Phe Ser Ala Tyr
        515                 520                 525
Val Ala Ser Lys Ser Ala Leu Asp Ala Phe Ser Arg Cys Ala Ala Ala
530                 535                 540
Glu Trp Ser Asp Arg Asn Val Thr Phe Thr Thr Ile Asn Met Pro Leu
545                 550                 555                 560
Val Lys Thr Pro Met Ile Ala Pro Thr Lys Ile Tyr Asp Ser Val Pro
                565                 570                 575
Thr Leu Thr Pro Asp Glu Ala Ala Gly Met Val Ala Asp Ala Ile Val
            580                 585                 590
Tyr Arg Pro Lys Arg Ile Ala Thr Arg Leu Gly Ile Phe Ala Gln Val
        595                 600                 605
Leu His Ala Leu Ala Pro Lys Met Gly Glu Ile Val Met Asn Thr Gly
610                 615                 620
Tyr Arg Met Phe Pro Asp Ser Pro Ala Ala Gly Ser Lys Ser Gly
625                 630                 635                 640
Glu Lys Pro Lys Val Ser Thr Glu Gln Val Ala Phe Ala Ala Ile Met
                645                 650                 655
```

-continued

Arg Gly Ile Tyr Trp
            660

<210> SEQ ID NO 23
<211> LENGTH: 661
<212> TYPE: PRT
<213> ORGANISM: Marinobacter lipolyticus SM19
<220> FEATURE:
<223> OTHER INFORMATION: Short chain dehydrogenase

<400> SEQUENCE: 23

Met Asn Tyr Phe Leu Thr Gly Gly Thr Gly Phe Ile Gly Arg Phe Leu
1               5                   10                  15

Val Glu Lys Leu Leu Ala Arg Gly Gly Thr Val His Val Leu Val Arg
            20                  25                  30

Glu Gln Ser Leu Gly Lys Leu Asp Ile Leu Arg Glu Arg Trp Gly Ala
        35                  40                  45

Asp Glu Asn Gln Val Lys Ala Val Ile Gly Asp Leu Thr Ser Pro Asn
    50                  55                  60

Leu Gly Ile Asp Asp Lys Thr Met Asp Ala Leu Lys Gly Gln Val Asp
65                  70                  75                  80

His Phe Phe His Leu Ala Ala Val Tyr Asp Met Gly Ala Asp Glu Glu
                85                  90                  95

Ala Gln Gln Ala Thr Asn Ile Glu Gly Thr Arg Ser Ala Val Asn Ala
            100                 105                 110

Ala Gln Ala Met Gly Ala Gly Cys Phe His His Val Ser Ser Ile Ala
        115                 120                 125

Ala Ala Gly Leu Phe Lys Gly Thr Phe Arg Glu Asp Met Phe Glu Glu
    130                 135                 140

Ala Glu Lys Leu Asp His Pro Tyr Leu Leu Thr Lys His Glu Ser Glu
145                 150                 155                 160

Lys Val Val Arg Glu Ser Cys Lys Val Pro Phe Arg Ile Tyr Arg Pro
                165                 170                 175

Gly Met Val Ile Gly His Ser Glu Thr Gly Glu Met Asp Lys Val Asp
            180                 185                 190

Gly Pro Tyr Tyr Phe Phe Lys Met Ile Gln Lys Ile Arg His Ala Leu
        195                 200                 205

Pro Gln Trp Val Pro Thr Ile Gly Ile Glu Gly Gly Arg Leu Asn Val
    210                 215                 220

Val Pro Val Asp Phe Val Val Asn Ala Leu Asp His Ile Ala His Leu
225                 230                 235                 240

Glu Gly Glu Asp Gly Asn Cys Phe His Leu Val Asp Ser Asp Pro His
                245                 250                 255

Lys Val Gly Glu Ile Leu Asn Ile Phe Cys Glu Ala Gly His Ala Pro
            260                 265                 270

Arg Met Gly Met Arg Ile Asp Ser Arg Met Phe Gly Phe Val Pro Pro
        275                 280                 285

Phe Ile Arg Gln Ser Leu Lys Asn Leu Pro Pro Val Lys Arg Leu Thr
    290                 295                 300

Ser Ala Val Leu Asp Asp Met Gly Ile Pro Pro Ser Val Leu Ser Phe
305                 310                 315                 320

Ile Asn Tyr Pro Thr Arg Phe Asp Ala Arg Glu Thr Glu Arg Val Leu
                325                 330                 335

Lys Gly Thr Asp Ile Ala Val Pro Arg Leu Gln Asp Tyr Ala Pro Val
            340                 345                 350

Ile Trp Asp Tyr Trp Glu Arg His Leu Asp Pro Asp Leu Phe Lys Asp
            355                 360                 365

Arg Thr Leu Arg Gly Thr Val Glu Gly Lys Val Cys Val Val Thr Gly
        370                 375                 380

Gly Thr Ser Gly Ile Gly Leu Ala Thr Ala Gln Lys Leu Ala Asp Ala
385                 390                 395                 400

Gly Ala Ile Leu Val Ile Gly Ala Arg Lys Lys Glu Arg Leu Ala Glu
                405                 410                 415

Ile Thr Ala Asp Leu Glu Ala Arg Gly Gly Asn Val His Ala Tyr Gln
            420                 425                 430

Cys Asp Phe Ala Glu Met Glu Asp Cys Asp Arg Phe Val Gln Thr Val
        435                 440                 445

Leu Glu Asn His Gly His Val Asp Val Leu Val Asn Asn Ala Gly Arg
    450                 455                 460

Ser Ile Arg Arg Ser Leu Ala Leu Ser Phe Asp Arg Phe His Asp Phe
465                 470                 475                 480

Glu Arg Thr Met Gln Leu Asn Tyr Phe Gly Ser Val Arg Leu Ile Met
                485                 490                 495

Gly Phe Ala Pro Ala Met Leu Glu Arg Arg Gly His Val Val Asn
            500                 505                 510

Ile Ser Ser Ile Gly Val Leu Thr Asn Ala Pro Arg Phe Ser Ala Tyr
        515                 520                 525

Val Ala Ser Lys Ser Ala Leu Asp Ala Phe Ser Arg Cys Ala Ala Ala
    530                 535                 540

Glu Trp Ser Asp Arg Asn Val Thr Phe Thr Thr Ile Asn Met Pro Leu
545                 550                 555                 560

Val Lys Thr Pro Met Ile Ala Pro Thr Lys Ile Tyr Asp Ser Val Pro
                565                 570                 575

Thr Leu Thr Pro Asp Glu Ala Ala Glu Met Val Ala Asp Ala Ile Val
            580                 585                 590

Tyr Arg Pro Lys Arg Ile Ala Thr Arg Leu Gly Ile Phe Ala Gln Val
        595                 600                 605

Leu His Ala Ile Ala Pro Lys Met Gly Glu Ile Val Met Asn Thr Gly
    610                 615                 620

Tyr Arg Met Phe Pro Asp Ser Pro Ala Ala Gly Ser Lys Ser Gly
625                 630                 635                 640

Glu Lys Pro Lys Val Ser Ser Glu Gln Val Ala Phe Ala Ala Ile Met
                645                 650                 655

Arg Gly Ile Tyr Trp
            660

<210> SEQ ID NO 24
<211> LENGTH: 661
<212> TYPE: PRT
<213> ORGANISM: Marinobacter hydrocarbonoclasticus ATCC 49840
<220> FEATURE:
<223> OTHER INFORMATION: Uncharacterized protein

<400> SEQUENCE: 24

Met Asn Tyr Phe Leu Thr Gly Gly Thr Gly Phe Ile Gly Arg Phe Leu
1               5                   10                  15

Val Glu Lys Leu Leu Ala Arg Gly Gly Thr Val Tyr Val Leu Val Arg
                20                  25                  30

Glu Gln Ser Gln Asp Lys Leu Glu Arg Leu Arg Glu Arg Trp Gly Ala
            35                  40                  45

```
Asp Asp Lys Gln Val Lys Ala Val Ile Gly Asp Leu Thr Ser Lys Asn
 50                  55                  60
Leu Gly Ile Asp Ala Lys Thr Leu Lys Ser Leu Lys Gly Asn Ile Asp
 65                  70                  75                  80
His Val Phe His Leu Ala Ala Val Tyr Asp Met Gly Ala Asp Glu Glu
                 85                  90                  95
Ala Gln Ala Ala Thr Asn Ile Glu Gly Thr Arg Ala Ala Val Gln Ala
            100                 105                 110
Ala Glu Ala Met Gly Ala Lys His Phe His Val Ser Ser Ile Ala
            115                 120                 125
Ala Ala Gly Leu Phe Lys Gly Ile Phe Arg Glu Asp Met Phe Glu Glu
        130                 135                 140
Ala Glu Lys Leu Asp His Pro Tyr Leu Arg Thr Lys His Glu Ser Glu
145                 150                 155                 160
Lys Val Val Arg Glu Glu Cys Lys Val Pro Phe Arg Ile Tyr Arg Pro
                165                 170                 175
Gly Met Val Ile Gly His Ser Glu Thr Gly Glu Met Asp Lys Val Asp
            180                 185                 190
Gly Pro Tyr Tyr Phe Phe Lys Met Ile Gln Lys Ile Arg His Ala Leu
        195                 200                 205
Pro Gln Trp Val Pro Thr Ile Gly Ile Glu Gly Arg Leu Asn Ile
210                 215                 220
Val Pro Val Asp Phe Val Val Asp Ala Leu Asp His Ile Ala His Leu
225                 230                 235                 240
Glu Gly Glu Asp Gly Asn Cys Phe His Leu Val Asp Ser Asp Pro Tyr
                245                 250                 255
Lys Val Gly Glu Ile Leu Asn Ile Phe Cys Glu Ala Gly His Ala Pro
            260                 265                 270
Arg Met Gly Met Arg Ile Asp Ser Arg Met Phe Gly Phe Ile Pro Pro
        275                 280                 285
Phe Ile Arg Gln Ser Ile Lys Asn Leu Pro Pro Val Lys Arg Ile Thr
290                 295                 300
Gly Ala Leu Leu Asp Asp Met Gly Ile Pro Pro Ser Val Met Ser Phe
305                 310                 315                 320
Ile Asn Tyr Pro Thr Arg Phe Asp Thr Arg Glu Leu Glu Arg Val Leu
                325                 330                 335
Lys Gly Thr Asp Ile Glu Val Pro Arg Leu Pro Ser Tyr Ala Pro Val
            340                 345                 350
Ile Trp Asp Tyr Trp Glu Arg Asn Leu Asp Pro Asp Leu Phe Lys Asp
        355                 360                 365
Arg Thr Leu Lys Gly Thr Val Glu Gly Lys Val Cys Val Thr Gly
370                 375                 380
Ala Thr Ser Gly Ile Gly Leu Ala Thr Ala Glu Lys Leu Ala Glu Ala
385                 390                 395                 400
Gly Ala Ile Leu Val Ile Gly Ala Arg Thr Lys Glu Thr Leu Asp Glu
                405                 410                 415
Val Ala Ala Ser Leu Glu Ala Lys Gly Gly Asn Val His Ala Tyr Gln
            420                 425                 430
Cys Asp Phe Ser Asp Met Asp Asp Cys Asp Arg Phe Val Lys Thr Val
        435                 440                 445
Leu Asp Asn His Gly His Val Asp Val Leu Val Asn Asn Ala Gly Arg
450                 455                 460
```

```
Ser Ile Arg Arg Ser Leu Ala Leu Ser Phe Asp Arg Phe His Asp Phe
465                 470                 475                 480

Glu Arg Thr Met Gln Leu Asn Tyr Phe Gly Ser Val Arg Leu Ile Met
                485                 490                 495

Gly Phe Ala Pro Ala Met Leu Glu Arg Arg Gly His Val Val Asn
            500                 505                 510

Ile Ser Ser Ile Gly Val Leu Thr Asn Ala Pro Arg Phe Ser Ala Tyr
            515                 520                 525

Val Ala Ser Lys Ser Ala Leu Asp Ala Phe Ser Arg Cys Ala Ala Ala
            530                 535                 540

Glu Trp Ser Asp Arg Asn Val Thr Phe Thr Thr Ile Asn Met Pro Leu
545                 550                 555                 560

Val Lys Thr Pro Met Ile Ala Pro Thr Lys Ile Tyr Asp Ser Val Pro
                565                 570                 575

Thr Leu Thr Pro Asp Glu Ala Ala Gln Met Val Ala Asp Ala Ile Val
                580                 585                 590

Tyr Arg Pro Lys Arg Ile Ala Thr Arg Leu Gly Val Phe Ala Gln Val
            595                 600                 605

Leu His Ala Leu Ala Pro Lys Met Gly Glu Ile Ile Met Asn Thr Gly
610                 615                 620

Tyr Arg Met Phe Pro Asp Ser Pro Ala Ala Gly Ser Lys Ser Gly
625                 630                 635                 640

Glu Lys Pro Lys Val Ser Thr Glu Gln Val Ala Phe Ala Ile Met
                645                 650                 655

Arg Gly Ile Tyr Trp
            660

<210> SEQ ID NO 25
<211> LENGTH: 258
<212> TYPE: PRT
<213> ORGANISM: Myxococcus xanthus (strain DK 1622)
<220> FEATURE:
<223> OTHER INFORMATION: 3-hydroxybutyryl-CoA dehydratase

<400> SEQUENCE: 25

Met Pro Glu Phe Lys Val Asp Ala Arg Gly Pro Ile Glu Ile Trp Thr
1               5                   10                  15

Ile Asp Gly Glu Ser Arg Arg Asn Ala Ile Ser Arg Ala Met Leu Lys
            20                  25                  30

Glu Leu Gly Glu Leu Val Thr Arg Val Ser Ser Ser Arg Asp Val Arg
        35                  40                  45

Ala Val Val Ile Thr Gly Ala Gly Asp Lys Ala Phe Cys Ala Gly Ala
    50                  55                  60

Asp Leu Lys Glu Arg Ala Thr Met Ala Glu Asp Val Arg Ala Phe
65                  70                  75                  80

Leu Asp Gly Leu Arg Arg Thr Phe Arg Ala Ile Glu Lys Ser Asp Cys
                85                  90                  95

Val Phe Ile Ala Ala Ile Asn Gly Ala Ala Leu Gly Gly Gly Thr Glu
            100                 105                 110

Leu Ala Leu Ala Cys Asp Leu Arg Val Ala Ala Pro Ala Ala Glu Leu
        115                 120                 125

Gly Leu Thr Glu Val Lys Leu Gly Ile Ile Pro Gly Gly Gly Thr
    130                 135                 140

Gln Arg Leu Ala Arg Leu Val Gly Pro Gly Arg Ala Lys Asp Leu Ile
145                 150                 155                 160
```

```
Leu Thr Ala Arg Arg Ile Asn Ala Ala Glu Ala Phe Ser Val Gly Leu
            165                 170                 175

Ala Asn Arg Leu Ala Pro Glu Gly His Leu Leu Ala Val Ala Tyr Gly
            180                 185                 190

Leu Ala Glu Ser Val Val Glu Asn Ala Pro Ile Ala Val Ala Thr Ala
            195                 200                 205

Lys His Ala Ile Asp Glu Gly Thr Gly Leu Glu Leu Asp Asp Ala Leu
            210                 215                 220

Ala Leu Glu Leu Arg Lys Tyr Glu Glu Ile Leu Lys Thr Glu Asp Arg
225                 230                 235                 240

Leu Glu Gly Leu Arg Ala Phe Ala Glu Lys Arg Ala Pro Val Tyr Lys
            245                 250                 255

Gly Arg
```